(12) United States Patent
Korinek et al.

(10) Patent No.: US 11,839,615 B2
(45) Date of Patent: Dec. 12, 2023

(54) COMPOUNDS AND METHODS FOR TREATING ADDICTION AND RELATED DISORDERS

(71) Applicants: Astrocyte Pharmaceuticals, Inc., Cambridge, MA (US); The Board of Regents of the University of Texas System, Austin, TX (US)

(72) Inventors: William S. Korinek, Mystic, CT (US); Theodore E Liston, Stonington, CT (US); James D. Lechleiter, San Antonio, TX (US); Michael Beckstead, Oklahoma City, OK (US)

(73) Assignees: Astrocyte Pharmaceuticals, Inc., Cambridge, MA (US); The Board of Regents of the University of Texas System, San Antonio, TX (US)

( * ) Notice: Subject to any disclaimer, the term of this patent is extended or adjusted under 35 U.S.C. 154(b) by 390 days.

(21) Appl. No.: 16/968,287

(22) PCT Filed: Feb. 8, 2019

(86) PCT No.: PCT/US2019/017265
§ 371 (c)(1),
(2) Date: Aug. 7, 2020

(87) PCT Pub. No.: WO2019/157317
PCT Pub. Date: Aug. 15, 2019

(65) Prior Publication Data
US 2021/0030760 A1    Feb. 4, 2021

Related U.S. Application Data

(60) Provisional application No. 62/628,658, filed on Feb. 9, 2018.

(51) Int. Cl.
*A61K 31/52* (2006.01)
*A61P 25/36* (2006.01)
*A61K 31/7076* (2006.01)

(52) U.S. Cl.
CPC .......... *A61K 31/52* (2013.01); *A61K 31/7076* (2013.01); *A61P 25/36* (2018.01)

(58) Field of Classification Search
CPC .............................. A61K 31/52; C07D 473/40
USPC .............................................. 514/46; 544/264
See application file for complete search history.

(56) References Cited

U.S. PATENT DOCUMENTS

| | | | |
|---|---|---|---|
| 5,773,423 A | 6/1998 | Jacobson et al. | |
| 6,586,413 B2 | 7/2003 | Liang et al. | |
| 7,064,112 B1 | 6/2006 | Fishman | |
| 7,087,589 B2 | 8/2006 | Jacobson et al. | |
| 7,348,315 B2 | 3/2008 | Liang et al. | |
| 7,414,036 B2 | 8/2008 | Sevillano et al. | |
| 7,589,075 B2 | 9/2009 | Fishman et al. | |
| 7,790,735 B2 | 9/2010 | Jacobson et al. | |
| 7,825,126 B2 | 11/2010 | Jacobson et al. | |
| 7,867,983 B2 | 1/2011 | Liang et al. | |
| 8,399,018 B2 | 3/2013 | Lichter et al. | |
| 8,410,078 B2 | 4/2013 | Liang et al. | |
| 8,518,957 B2 | 8/2013 | Jacobson et al. | |
| 8,685,372 B2 | 4/2014 | Tsien et al. | |
| 8,691,775 B2 | 4/2014 | Wurtman | |

(Continued)

FOREIGN PATENT DOCUMENTS

EP        1624753 A2    2/2006
WO    WO-2006031505 A1    3/2006

(Continued)

OTHER PUBLICATIONS

Ando et al., "A comparative analysis of the activity of ligands acting at P2X and P2Y receptor subtypes in models of neuropathic, acute and inflammatory pain," British Journal of Pharmacology. 2010; 159(5): 1106-1117.

(Continued)

*Primary Examiner* — Jeffrey H Murray
(74) *Attorney, Agent, or Firm* — Dechert LLP; Joseph W. Arico; Hannah Peters

(57) ABSTRACT

The present invention relates to adenosine receptor agonist compounds and methods of use thereof for treatment of certain disorders and conditions, for example an addiction or compulsive disorder. Exemplary compounds for use in disclosed methods include:

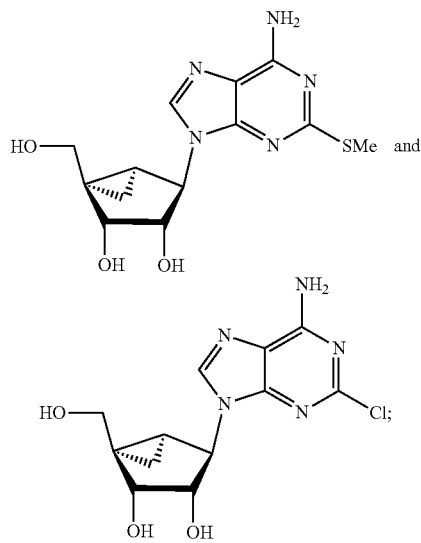

and pharmaceutically acceptable salts thereof.

18 Claims, 9 Drawing Sheets

(56) References Cited

U.S. PATENT DOCUMENTS

| | | |
|---|---|---|
| 8,735,407 B2 | 5/2014 | Jacobson et al. |
| 8,796,291 B2 | 8/2014 | Jacobson et al. |
| 8,822,434 B2 | 9/2014 | Liang et al. |
| 8,916,570 B2 | 12/2014 | Jacobson et al. |
| 9,132,131 B2 | 9/2015 | Salvemini |
| 9,181,253 B2 | 11/2015 | Jacobson et al. |
| 9,387,220 B2 | 7/2016 | Fishman et al. |
| 9,526,739 B2 | 12/2016 | Liang et al. |
| 9,789,131 B1 | 10/2017 | Korinek et al. |
| 9,963,450 B2 | 5/2018 | Jacobson et al. |
| 10,265,338 B2 | 4/2019 | Korinek et al. |
| 10,765,693 B2 | 9/2020 | Poe et al. |
| 10,953,031 B2 | 3/2021 | Poe et al. |
| 2003/0216412 A1 | 11/2003 | Jacobson et al. |
| 2009/0088403 A1 | 4/2009 | Blakely et al. |
| 2009/0306225 A1 | 12/2009 | Lichter et al. |
| 2010/0256086 A1 | 10/2010 | Fischer |
| 2011/0046166 A1 | 2/2011 | Jacobson et al. |
| 2014/0241990 A1 | 8/2014 | Haydon et al. |
| 2015/0087613 A1 | 3/2015 | Salvemini |
| 2017/0002007 A1 | 1/2017 | Jacobson et al. |
| 2018/0021363 A1 | 1/2018 | Korinek et al. |
| 2020/0046751 A1 | 2/2020 | Korinek et al. |

FOREIGN PATENT DOCUMENTS

| | | | |
|---|---|---|---|
| WO | WO-2006091905 A1 | 8/2006 | |
| WO | WO-2007020018 A1 | 2/2007 | |
| WO | WO-2008021552 A2 | 2/2008 | |
| WO | WO-2009010871 A2 | 1/2009 | |
| WO | WO-2010014921 A2 | 2/2010 | |
| WO | WO-2011077435 A1 | 6/2011 | |
| WO | WO-2014160502 A1 | 10/2014 | |
| WO | 2015080940 A1 | 6/2015 | |
| WO | WO-2016123672 A1 | 8/2016 | |

OTHER PUBLICATIONS

Armstrong et al., "Adenosine receptor specificity in preconditioning of isolated rabbit cardiomyocytes: evidence of A3 receptor involvement," Cardiovascular Research. 1994; 28(7): 1049-1056.

Auchampach et al., "Selective Activation of A3 Adenosine Receptors with N6-(3-Iodobenzyl)Adenosine-5'-N-Methyluronamide Protects Against Myocardial Stunning and Infarction without Hemodynamic Changes in Conscious Rabbits," Circulation Research. 1997; 80: 800-809.

Baltos et al., "Structure-Activity Analysis of Biased Agonism at the Human Adenosine A3 Receptor," Molecular Pharmacology. 2016; 90(1): 12-22.

Barragán-Iglesias et al., "Participation of Peripheral P2Y1, P2Y6 and P2Y11 receptors in formalin- induced inflammatory pain in rats," Pharmacology, Biochemistry and Behavior. 2015; 128: 23-32.

Ben et al., "Different efficacy of adenosine and NECA derivatives at the human A3 adenosine receptor: insight into the receptor activation switch," Biochemical Pharmacology. 2014; 87(2): 321-331.

Beukers et al., "New, non-adenosine, high-potency agonists for the human adenosine A2B receptor with an improved selectivity profile compared to the reference agonist N-ethylcarboxamidoadenosine," Journal of Medicinal Chemistry. 2004; 47(15): 3707-3709.

Björklund et al., "Adenosine A1 and A3 receptors protect astrocytes from hypoxic damage," European Journal of Pharmacology. 2008; 596: 6-13.

Borea et al., "The A3 Adenosine Receptor: History and Perspectives," Pharmacological Reviews. 2015; 67: 74-102.

Bourdon et al., "(N)-methanocarba-2MeSADP (MRS2365) is a subtype-specific agonist that induces rapid desensitization of the P2Y1, receptor of human platelets," Journal of Thrombosis and Haemostasis. 2006; 4(4): 861-868.

Camaioni et al., "Adenosine receptor agonists: synthesis and biological evaluation of the disatereoisomers of 2-(3-hydroxy-3-phenyl-1-propyn-1-yl)NECA," Bioorganic & Medicinal Chemistry. 1997; 5(12): 2267-2275.

Chen et al., "Activation of Adenosine A3 Receptors Reduces Ischemic Brain Injury in Rodents," Journal of Neuroscience Research. 2006; 84: 1848-1855.

Choi et al., "Preparative and Stereoselective Synthesis of the Versatile Intermediate for Carbocyclic Nucleosides: Effects of the Bulky Protecting Groups to Enforce Facial Selectivity," J. Org. Chem. 2004; 69(7): 2634-2636.

Choi et al., "A3 Adenosine Receptor Agonist Reduces Brain Ischemic Injury and Inhibits Inflammatory Cell Migration in Rats," The America Journal of Pathology. 2011; 179(4): 2042-2052.

Ciancetta et al., "Structural Probing and Molecular Modeling of the A3 Adenosine Receptor: A Focus on Agonist Binding," Molecules. 2017; 22(3): 17 pages.

Cosyn et al., "2-Triazole-Substituted Adenosines: A New Class of Selective A3 Adenosine Receptor Agonists, Partial Agonists, and Antagonists," The Journal of Medicinal Chemistry. 2006; 49(25):7373-7383.

Cosyn et al., "Synthesis of hypermodified adenosine derivatives as selective adenosine A3 receptor ligands," Bioorganic & Medicinal Chemistry. 2006; 14: 1403-1412.

Cristalli et al., "2-Aralkynyl and 2-Heteroalkynyl derivatives of adenosine-5'-N-ethyluronamide as selective A2a adenosine receptor agonists," Journal of Medicinal Chemistry. 1995; 38(9): 1462-1472.

D'Alimonte et al., "Potentiation of temozolomide antitumor effect by purine receptor ligands able to restrain the in vitro growth of human glioblastoma stem cells," Purinergic Signalling. 2015; 11(3): 331-346.

Devine et al., "Synthesis and evaluation of new N6-substituted adenosine-5'-N- methylcarboxamides as A3 adenosine receptor agonists," Bioorganic & Medicinal Chemistry. 2010; 18(8): 3078-3087.

Doyle et al., "Adenosine A3 Receptor Expression and Function in Mitochondria," The FASEB Journal. 2016; 30(1): Supplement 1266.6 (2 pages).

Fedorova et al., "Behavioral Characterization of Mice Lacking the A3 Adenosine Receptor: Sensitivity to Hypoxic Neurodegeneration," Cell Molecular Neurobiology. 2003; 23(3): 431-447.

Gao et al., "Allosteric modulation and functional selectivity of G protein-coupled receptors," Drug Discovery Today Technologies. 2013; 10(2): e237-e243.

Gao et al., "Functionally biased modulation of A3 adenosine receptor agonist efficacy and potency by imidazoquinolinamine allosteric enhancers," Biochemical Pharmacology. 2011; 82(6): 658-668.

Gao et al., "Partial Agonists for A3 Adenosine Receptors," Current Topics in Medicinal Chemistry. 2004; 4(8): 855-862.

Gao et al., "Structural Determinants of A3 Adenosine Receptor Activation: Nucleoside Ligands at the Agonist/Antagonist boundary," Journal of Medicinal Chemistry. 2002; 45(20): 4471-4484.

Gillerman et al. "Investigations into the Origin of the Molecular Recognition of Several Adenosine Deaminase Inhibitors," J. Med. Chem. 2011; 54(1):107-121.

Goadsby et al., "Adenosine A1 receptor agonists inhibit trigeminovascular nociceptive transmission," Guarantors of Brain. 2002; 1392-1401.

Gundry et al., "A Practical Guide to Approaching Biased Agonism at G Protein Coupled Receptors," Frontiers in Neuroscience. 2017; 11(17): 6 pages.

International Search Report and Written Opinion issued in PCT/US2017/028996 dated Aug. 2, 2017 (10 pages).

International Search Report and Written Opinion issued in PCT/US2019/017265 dated May 7, 2019 (9 pages).

International Search Report and Written Opinion issued in PCT/US2019/053076 dated Dec. 13, 2019 (8pages).

Jacobson et al., "Medicinal Chemistry of the A3 Adenosine Receptor: Agonists, Antagonists, and Receptor Engineering," Handbook Experimental Pharmacology, 2009; 193: 123-159.

Jacobson et al., "P2Y nucleotide receptors: Promise of therapeutic applications," Drug Discovery Today. 2010; 15(13-14): 570-578.

Jacobson et al., "John Daly Lecture: Structure-guided Drug Design for Adenosine and P2Y Receptors," Computational and Structural Biotechnology Journal. 2014; 13: 286-298.

(56) References Cited

OTHER PUBLICATIONS

Kenakin et al., "A simple method for quantifying functional selectivity and agonist bias," ACS Chem Neurosci. 2012; 3:193-203.
Kim et al., "Three-dimensional quantitative structure-activity relationship of nucleosides acting at the A3 adenosine receptor: analysis of binding and relative efficacy," Journal of Chemical Information and Modeling. 2007; 47(3): 1225-1233.
Klotz et al., "2-substituted N-ethylcarboxamidoadenosine derivatives as high-affinity agonists as human A3 adenosine receptors," Naunyn-Schmiedeberg's Archives of Pharmacology. 1999; 360(2): 103-108.
Klotz, "Adenosine receptors and their ligands," Naunyn Schmiedebergs Arch Pharmacol. 2000; 362(4-5): 382-391.
Koch et al., "Impaired Cognition after Stimulation of P2Y1 Receptors in the Rat Medial Prefrontal Cortex," Neuropsychopharmacology. 2015; 40(2): 305-314.
Kumar et al., "5'-Phosphate and 5'-Phosphonate Ester Derivatives of (N)-Methanocarba Adenosine with in Vivo Cardioprotective Activity," Journal of Medicinal Chemistry. 2013; 56(3): 902-914.
Kwon et al., "Blockade of Peripheral P2Y1 Receptors Prevents the Induction of Thermal Hyperalgesia via Modulation of TRPV1 Expression in Carrageenan-Induced Inflammatory Pain Rats: Involvement of p38 MAPK Phosphorylation in DRGs," Neuropharmacology. 2013; 79: 368-379.
Lee et al., "Ring-Constrained (N)-Methanocarba Nucleosides as Adenosine Receptor Agonists: Independent 5'-Uronamide and 2'-Deoxy Modifications," Bioorganic & Medicinal Chemistry Letters. 2001; 11: 1333-1337.
Lewerenz et al., "A3 Receptors in Cortical Neurons: Pharmacological Aspects and Neuroprotection during Hypoxia," Drug Development Research. 2003; 58: 420-427.
Liang et al., "A physiological role of the adenosine A3 receptor: Sustained cardioprotection," The Proceedings of the National Academy of Science, U.S.A. 1998; 95(12): 6995-6999.
Lin et al., "Ca2+ signaling, mitochondria and sensitivity to oxidative stress in aging astrocytes," Neurobiol Aging. 2007; 28(1): 99-111.
Little et al., "Endogenous adenosine A3 receptor activation selectively alleviates persisent pain states," Brain Advance Access. 2015; 1-8.
Lubitz et al., "Adenosine A3 receptor stimulation and cerebral ischemia," European Journal of Pharmacology. 1994; 263: 59-67.
Lubitz et al., "Chronic administration of adenosine A3 receptor agonist and cerebral ischemia: neuronal and glial effects," European Journal of Pharmacology. 1999; 367: 157-163.
Lubitz et al., "Right Thing at a Wrong Time? Adenosine A3 Receptors and Cerebroprotection in Stroke," Annals New York Academy of Sciences, Neuroprotective Agents: Fifth International Conference. 2001; 939: 85-96.
Mañé et al., "Differential functional role of purinergic and nitrergic inhibitory co-transmitters in human colonic relaxation," Acta Physiologica. 2014; 212(4): 293-305.
May et al., "Structure-function studies of allosteric agonism at M2 muscarinic acetylcholine receptors," Mol Pharmacol. 2007; 72:463-476.
Mayo Clinic Staff, "Compulsive Gambling—Symptoms", Mayo Foundation for Medical Education and Research (MFMER), (Oct. 22, 2016), p. 1, URL: https://www.mayoclinic.org/diseases-conditions/compulsive-gambling/symptoms-causes/syc-20355178.
Mayo Clinic Staff, "Compulsive Gambling—Diagnosis", Mayo Foundation for Medical Education and Research (MFMER), (Oct. 22, 2016), p. 1, URL: https://www.mayoclinic.org/diseases-conditions/compulsive-gambling/diagnosis-treatment/drc-20355184.
McCall et al., "Selective Ablation of GIRK Channels in Dopamine Neurons Alters Behavioral Effects of Cocaine in Mice," Neuropsychopharmacology. 2017; 42(3): 707-715.
McCarthy et al., "Preparation of separate astroglial and oligodendroglial cell cultures from rat cerebral tissue," J Cell Biol. 1980; 85(3): 890-902.

Michel et al., "Total syntheses of a conformationally locked North-type methanocarba puromycin analogue and a dinucleotide derivative," Chemistry. 2009; 15(25):6244-57.
Müller et al., "Recent developments in adenosine receptor ligands and their potential as novel drugs," Biochimica et Biophysica Acta. 2011; 1808(5): 1290-1308.
Nayak et al., "Synthesis and Anti-Renal Fibrosis Activity of Conformationally Locked Truncated 2-Hexynyl-N6-Substituted-(N)-Methanocarba-nucleosides as A3 Adenosine Receptor Antagonists and Partial Agonists," Journal of Medicinal Chemistry. 2014; 57(4): 1344-1354.
Paoletta et al., "Rational Design of Sulfonated A3 Adenosine Receptor-Selective Nucleosides as Pharmacological Tools to Study Chronic Neuropathic Pain," Journal of Medicinal Chemistry. 2013; 56(14): 5949-5963.
Perreira et al., "'Reversine' and its 2-Substituted Adenine Derivates as Potent and Selective A3 Adenosine Receptor Antagonists," The Journal of Medicinal Chemistry. 2005; 48(15): 4910-4918.
Pubchem, "Compound Summary for CID 69572716, SCHEMBL5803724," retrieved from <<https://pubchem.ncbi.nlm.nih.gov/compound/69572716#section=Top>> accessed on Mar. 17, 2017 (10 pages).
Pugliese et al., "Role of adenosine A3 receptors on CA1 hippocampal neurotransmission during oxygen-glucose deprivation episodes of different duration," Biochemical Pharmacology. 2007; 74(5): 768-779.
Ravi et al., "Adenine Nucleotide Analogues Locked in a Northern Methanocarba Conformation: Enhanced Stability and Potency as P2Y1 Receptor Agonists," Journal of Medicinal Chemistry. 2002; 45(10): 2090-2100.
Sharpe et al., "Methamphetamine self-administration in mice decreases GIRK channel-mediated currents in midbrain dopamine neurons," Int J Neuropsychopharmacol. 2014; 18(5):pyu073.
Stewart et al. "Determination of adenosine A1 receptor agonist and antagonist pharmacology using *Saccharomyces cerevisiae*: implications for li- gand screening and functional selectivity," J Pharmacol Exp Ther. 2009; 331:277-286.
Tamada et al., "Calcium responses in subserosal interstitial cells of the guinea pig proximal colon," Neurogastroenterology and motility: the official journal of the European Gastrointestinal Motility Society. 2014; 26(1): 115-123.
Tosh et al., "Structure-guided design of A3 adenosine receptor—selective nucleosides: combination of 2-arylethynyl and bicyclo[3. 1.0]hexane substitutions," J Med Chem. 2012; 55:4847-4860.
Tosh et al., "Truncated nucleosides as A3 adenosine receptor ligands: Combined 2-arylethynyl and bicyclohex- ane substitutions," ACS Med Chem Lett. 2012; 3:596-601.
Tosh et al., "Click Modification in the N6 Region of A3 Adenosine Receptor-Selective Carbocyclic Nucleosides for Dendrimeric Tethering that Preserves Pharmacophore Recognition," Bioconjugate Chemistry. 2012; 23(2): 232-247.
Tosh et al., "Structural Sweet Spot for A1 Adenosine Receptor Activation by Truncated (N)-Methanocarba Nucleosides: Receptor Docking and Potent Anticonvulsant Activity," Journal of Medicinal Chemistry. 2012; 55(18): 8075-8090.
Tosh et al., "Methanocarba ring as a ribose modification in ligands of G protein-coupled purine and pyrimidine receptors: synthetic approaches," MedChemComm. 2013; 2013(4): 619-630.
Tosh et al., "Efficient, large-scale synthesis and preclinical studies of MRS5698, a highly selective A3 adenosine receptor agonist that protects against chronic neuropathic pain," Purinergic Signalling. 2015; 11(3): 371-387.
Toti et al., "Synthesis and Evaluation of N6-Substituted Apioadenosines as Potential Adenosine A3 Receptor modulators," Bioorganic & Medicinal Chemistry Journal. 2014; 22(15): 4257-4268.
Tracey et al., "Novel N6-substituted adenosine 5'-N-methyluronamindes with high selectivity for human adenosine A3 receptors reduce ischemic myocardial injury," American Journal of Physiology Heart and Circulatory Physiology. 2003; 285(6): H2780-H2787.
Van der Westhuizen et al., "Quantification of ligand bias for clinically relevant b2-adrenergic receptor ligands: implications for drug taxonomy," Mol Pharmacol. 2014; 85:492-509.

(56) References Cited

OTHER PUBLICATIONS

Verzijl et al., "Functional selectivity of adenosine receptor ligands," Purinergic Signalling. 2011; 7: 171-192.

Volpini et al. "HEMADO as Potent and Selective Agonists of hA3R," Eur J Pharmacol. 2007; 556(1-3): 14-8.

Volpini et al., "Synthesis and biological evaluation of 2-alkynyl-N6-methyl-5'-N- methylcarboxamidoadenosine derivatives as potent and highly selective agonists for the human adenosine A3 receptor," Journal of Medicinal Chemistry. 2009; 52(23): 7897-7900.

Wan et al., "The A3 adenosine receptor agonist CP-532,903 [N6-(2,5-dichlorobenzyl)-3'- aminoadenosine-5'-N-methylcarboxamide] protects against myocardial ischemia/reperfusion injury via the sarcolemmal ATP-sensitive potassium channel," Journal of Pharmacology and Experimental Therapeutics. 2008; 324(1): 234-243.

Warden et al., "Guidelines for the pharmacologic treatment of neurobehavioral sequelae of traumatic brain injury," Journal of Neurotrauma. 2006; 23(10): 1468-1501.

Wei et al., "Activation of the P2Y1 receptor induces apoptosis and inhibits proliferation of prostate cancer cells," Biochemical Pharmacology. 2011; 82(4): 418-425.

Wootten et al., "Differential activation and modulation of the glucagon-like peptide-1 receptor by small molecule ligands," Mol Pharmacol. 2013; 83:822-834.

Wong et al., "Post exposure administration of A1 adenosine receptor agonists attenuates noise-induced hearing loss", Hearing Research. 2010; 260: 81-88.

Wu et al., "Purinergic receptor-stimulated IP3-mediated Ca2+ release enhances neuroprotection by increasing astrocyte mitochondrial metabolism during aging," J Neurosci. 2007; 27(24): 6510-20.

Zheng et al., "P2Y1R-initiated, IP3R-dependent stimulation of astrocyte mitochondrial metabolism reduces and partially reverses ischemic neuronal damage in mouse," J Cereb Blood Flow Metab. 2013; 33(4):600-11.

Zheng et al. "Purinergic receptor stimulation reduces cytotoxic edema and brain infarcts in mouse induced by photothrombosis by energizing glial mitochondria," PLoS One. 2010; 5(12): e14401.

Ziganshin et al., "Characteristics of ecto-ATPase of Xenopus oocytes and the inhibitory actions of suramin on ATP breakdown," Pflugers Archiv: European journal of physiology. 1995; 429(3): 412-418.

COMPOUNDS AND METHODS FOR TREATING ADDICTION AND RELATED DISORDERS

CROSS-REFERENCE TO RELATED APPLICATIONS

This application claims the benefit of U.S. Provisional Patent Application No. U.S. 62/628,658, filed on Feb. 9, 2018; the entirety of which is hereby incorporated by reference.

TECHNICAL FIELD

The present invention relates to compounds and methods of use thereof for treating, ameliorating, or promoting recovery from certain diseases and disorders such as addictions and compulsive disorders.

BACKGROUND OF THE INVENTION

Addictions and compulsive disorders are increasingly recognized as diseases in their own right and not merely as behaviors. As the neurological underpinnings of these disorders become better understood, there is the potential to treat them with pharmaceutical intervention. However, effective treatments for these disorders remain elusive and underexplored.

The nucleus accumbens and the ventral tegmental area (VTA) are believed to be the principal sites where addictive drugs act. Addictive drugs include heroin, cocaine, alcohol, opiates, nicotine, amphetamine, and their synthetic analogues. Such drugs cause changes in the neuromodulatory influence of dopamine on the processing of reinforcement signals whereby the action of dopamine in the nucleus accumbens is prolonged. Such drugs may also stimulate neurons in the nucleus accumbens and/or in the VTA. Common drugs of abuse stimulate the release of dopamine, creating both their rewarding and the psychomotor effects. The permanent functional changes in the mesolimbic dopamine system arising from repetitive dopamine stimulation result in compulsive drug-taking behaviors. Molecular and cellular adaptations are responsible for a sensitized dopamine activity in the VTA and along the mesolimbic dopamine projection in response to drug abuse. The activity of the dopamine-synthesizing enzyme tyrosine hydroxylase increases in addicted individuals, as does the ability of these neurons to respond to excitatory inputs. The latter effect is secondary to increases in the activity of the transcription factor CREB and the up regulation of GluR1, an important subunit of AMPA receptors for glutamate. These alterations in neural processing could account for the waning influence of adaptive emotional signals in the operation of decision making faculties as drug-seeking and drug-taking behaviors become habitual and compulsive.

Withdrawal generally takes place because the deficit in reward functioning initiates a distress cycle whenever the drug is not present. Thus, the drug is necessary to restore the normal homeostatic state. Research has shown that even after passing through the final stages of withdrawal, drug-seeking behavior can be reinstated if the formerly addicted individual is exposed to the drug or drug-related stimuli. It follows that breaking free of addiction is very difficult without some means of restoring normal brain function in the absence of the addictive drug.

There is therefore an urgent and unmet need for more effective treatments for addictions, brain reward system disorders, compulsive disorders, and related conditions.

DETAILED DESCRIPTION OF CERTAIN EMBODIMENTS OF THE INVENTION

Figure 1:
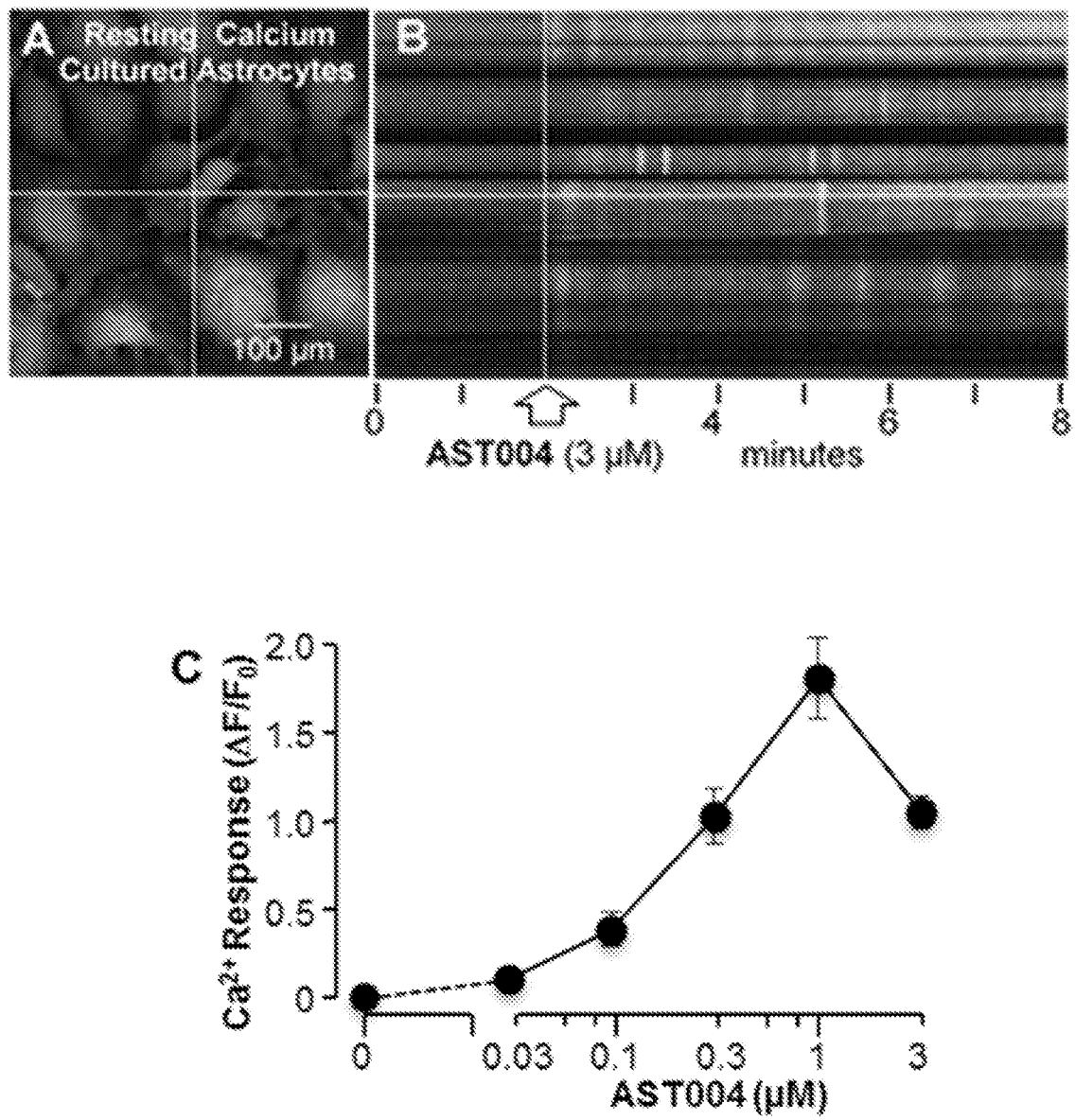
FIG. 1: AST-004 increases intracellular $Ca^{2+}$ in cultured astrocytes. A) Image of resting $Ca^{2+}$ levels in dye-loaded (Cal520) astrocytes. B) Spatio-temporal plot of $Ca^{2+}$ fluorescence for the vertical line in panel A. AST-004 was added at 2 min. Note the oscillatory $Ca^{2+}$ responses for over 6 minutes. C) Plot of integrated $Ca^{2+}$ fluorescence intensities ($DF/F_0$) at the indicated A3R agonist concentrations. Values are mean+/−SEM (data pooled from 3 experiments at each concentration). Images were acquired on the Nikon Swept-field confocal microscope.

1. Addictions, Addictive Behaviors, Behavioral Additions, Compulsive Disorders and Behaviors, and Related Conditions Cocaine self-administering mice exhibit significantly higher glutamate levels in the VTA (ventral tegmental area) of the brain. The VTA, in particular the VTA dopamine neurons, serve several functions in the reward system, motivation, cognition, and drug addiction, and may be the focus of several psychiatric disorders. The elevated glutamate levels appear to be due, at least in part, to loss of glutamate uptake into astrocytes. Without wishing to be bound by theory, it is believed that reduced availability of glutamate has negative effects on astrocyte function and this loss of function affects neuronal activity and drug-seeking behavior. It has now been found that the compounds disclosed herein treat or prevent relapse in addicted individuals, for example by reversing such loss of astrocyte function. Such loss of astrocyte function may be partly due to reduced expression of the glutamate transporter (GLT-1) in astrocytes. Since astrocytes metabolize glutamate to produce ATP, this likely impairs glutamate uptake, weakens astrocyte oxidative metabolism and downstream ATP-dependent processes and thereby weakens their ability to maintain an optimal environment for VTA neuronal activity.

Accordingly, in one aspect, the present invention provides a method of preventing, ameliorating, treating, or promoting recovery from an addiction, addictive behavior, behavioral addiction, brain reward system disorder, compulsive disorder, or related condition, comprising administering to a subject in need thereof an effective amount of a disclosed compound or pharmaceutically acceptable salt thereof.

In some embodiments, the addiction is to a substance or drug having abuse potential. In some embodiments, the substance or drug having abuse potential is a prescription or recreational drug.

In some embodiments, the substance or drug having abuse potential is selected from alcohol, nicotine, a stimulant, a cannabinoid agonist, or an opioid agonist. In some embodiments, the substance or drug having abuse potential is selected from heroin, cocaine, alcohol, an inhalant, an opioid, nicotine, an amphetamine, or a synthetic analog, salt, composition, or combination thereof.

In some embodiments, the amphetamine is selected from bupropion, cathinone, MDMA, or methamphetamine.

In some embodiments, the prescription or recreational drug is selected from a cannabinoid agonist or opioid agonist.

In some embodiments, the addiction is an alcohol or nicotine addiction.

In some embodiments, the subject is a polydrug abuser.

In some embodiments, the prescription or recreational drug is selected from cocaine, heroin, bupropion, cathinone, MDMA, or methamphetamine morphine, oxycodone, hydromorphone, fentanyl, or a combination thereof.

In some embodiments, a disclosed compound increases energy metabolism mediated by astrocytes, such as astrocyte mitochondria. In some embodiments, the compound reverses loss of glutamate uptake into astrocytes caused by a substance with abuse potential. In some embodiments, the compound at least partially reverses the remodeling of the brain reward system caused by the addiction. In some embodiments, such effects are mediated by brain or CNS adenosine $A_3$ receptors, such as astrocyte $A_3R$ in the VTA; or microglia $A_3R$.

In another aspect, the present invention provides a method of preventing, ameliorating, treating, or promoting recovery from an addiction, addictive behavior, behavioral addiction, brain reward system disorder, compulsive disorder, or related condition by increasing energy metabolism mediated by astrocytes, glia, microglia, neurons, endothelium cells, or other cells of the brain and/or CNS, comprising administering to a subject in need thereof an effective amount of a disclosed compound or pharmaceutically acceptable salt thereof.

In some embodiments, the method treats or prevents a relapse of an addiction or addictive behavior in the subject. In some embodiments, the subject is addicted to one or more addictive substances such as addictive drugs (drugs having abuse potential). As described below, such drugs include prescription drugs and recreational drugs such as heroin, cocaine, nicotine, or an opioid agonist.

In another aspect, the present invention provides a method of treating or preventing withdrawal caused by addiction to one or more addictive substances or drugs, comprising administering to a subject in need thereof an effective amount of a disclosed compound or pharmaceutically acceptable salt thereof. In some embodiments, the compound decreases withdrawal symptoms in an addicted individual in withdrawal. In some embodiments, the compound treats withdrawal in an addicted individual in withdrawal. In some embodiments, the method further comprises co-administering another drug for treating withdrawal and, optionally, counseling such as psychotherapy.

In some embodiments, the present invention provides a method of treating or preventing a relapse of a compulsive disorder or compulsive behavior, comprising administering to a subject in need thereof an effective amount of a disclosed compound.

In some embodiments, the compulsive disorder is obsessive-compulsive disorder (OCD), Tourette syndrome, trichotillomania, anorexia, bulimia, anxiety disorder, psychosis, or post-traumatic stress disorder.

According to another aspect, the present invention provides a method for treating one or more behavioral addictions and addictive behaviors or disorders comprising administering to a subject in need thereof a disclosed compound or pharmaceutically acceptable salt thereof. Behavioral addictions and addictive disorders result from the intoxication one senses from the release of brain chemicals (e.g., serotonin, adrenaline, epinephrine, etc.) during certain activities. Such disorders are known in the art and include gambling, sex addiction, pornography addiction, eating disorders, spending addiction, rage/anger, workaholism, exercise addiction, risk taking addictions (e.g. kleptomania and pyromania), perfectionism, internet or video game addiction, and compulsive use of electronic devices such as texting and checking social media, to name a few.

In some embodiments, activation of astrocytes is achieved through contacting with a disclosed compound one or more purinergic receptors such as adenosine receptors (ARs), for example those associated with or expressed by astrocytes or microglia, thus modulating the activity of the one or more receptors. In some embodiments, through effects on adenosine receptors such as $A_1$, $A_{2A}$, $A_{2B}$ and $A_3$ on astrocytes, the compound activates astrocytes to treat one or more disclosed diseases or conditions. In some embodiments, after administration to a subject in need thereof, a disclosed compound influences one or more functions such as glutamate uptake having an impact on energy metabolism of astrocytes or neuronal function, thus treating one or more diseases or conditions. In some embodiments, the compound is an AR agonist. In some embodiments, the purinergic receptor is an adenosine $A_3$ receptor ($A_3R$). In some embodiments, the compound is an $A_3R$ agonist. In some embodiments, the compound is a partial agonist or biased agonist or biased partial agonist, at an $A_3$ receptor ($A_3R$), such as a human $A_3$ receptor ($hA_3R$). In some embodiments, the compound is a biased antagonist at an $A_3$ receptor. In some embodiments, the compound is AST-004 or MRS1873 (AST-008) or a pharmaceutically acceptable salt thereof.

P2Y receptors are G-protein-coupled receptors and different subtypes of these receptors have important roles in processes such as synaptic communication, cellular differentiation, ion flux, vasodilation, blood brain barrier permeability, platelet aggregation and neuromodulation. Characterized members of the purinergic P2Y receptor family include the mammalian $P2Y_1$, $P2Y_{11}$, $P2Y_{12}$ and $P2Y_{13}$ receptors, which bind to adenine nucleotides; the $P2Y_4$, $P2Y_6$, and $P2Y_{14}$ receptors, that bind to uracil nucleotides; and the $P2Y_2$ and rodent $P2Y_4$ receptors, which have mixed selectivity. In some embodiments, activation of astrocytes is achieved through contacting with a disclosed compound one or more purinergic receptors such as P2Y receptors, for example those associated with or expressed by astrocytes, thus modulating the activity of the one or more receptors. In some embodiments, through effects on P2Y receptors such as $P2Y_1$, $P2Y_1$, $P2Y_{12}$ and $P2Y_{13}$ receptors associated with or expressed by astrocytes, the compound activates astrocytes to treat one or more disclosed diseases or conditions. In some embodiments, the P2Y receptor is a $P2Y_1$ receptor. In some embodiments, the $P2Y_1$ receptor is located on intracellular mitochondrial membranes. In some embodiments, the compound is a P2Y agonist. In some embodiments, the compound is a $P2Y_1$ agonist, e.g. at a human $P2Y_1$ receptor. In some embodiments, the compound is a biased agonist, partial agonist, or biased partial agonist at a $P2Y_1$ receptor, such as a human $P2Y_1$ receptor. In some embodiments, the compound is a biased antagonist at a $P2Y_1$ receptor. In some embodiments, the compound is 2MeSADP, MRS2365, the 5'-diphosphate of MRS1873 (MRS1873 is also known as AST-008), or AST-004; or a pharmaceutically acceptable salt thereof.

In one aspect, the present invention provides a method of treating or promoting recovery from an addiction, addictive behavior, behavioral addiction, brain reward system disorder, compulsive disorder, or related condition, comprising administering to a subject in need thereof an effective amount of a compound selected from:

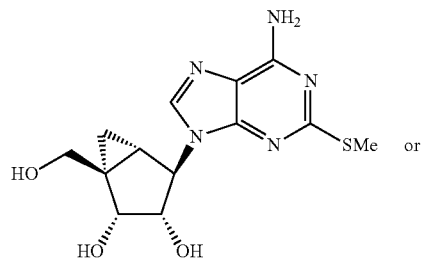

or

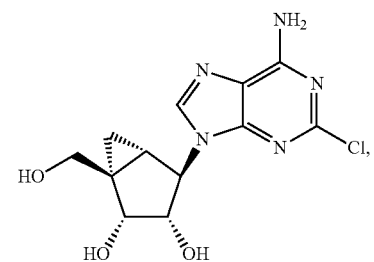

or a pharmaceutically acceptable salt thereof.

In another aspect, the present invention provides a method of treating or promoting recovery from withdrawal caused by addiction to a substance or drug having abuse potential, comprising administering to a subject in need thereof an effective amount of a compound selected from:

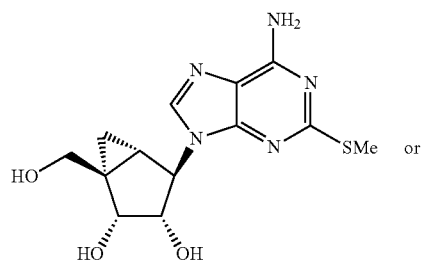

or

-continued

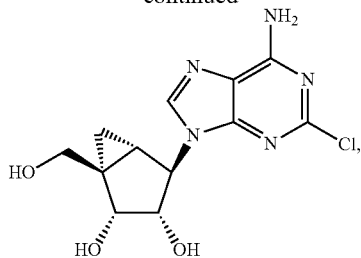

or a pharmaceutically acceptable salt thereof.

In some embodiments, the compound is

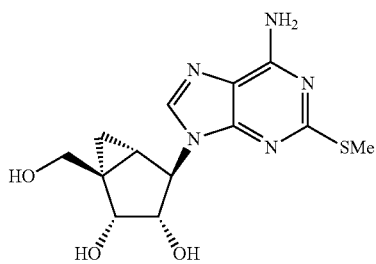 [SMILES: CSc1nc(N)c2ncn([C@H]3[C@H](O)[C@H](O)[C@]4(CO)C[C@H]34)c2n1]

or a pharmaceutically acceptable salt thereof.

In some embodiments, the compound is

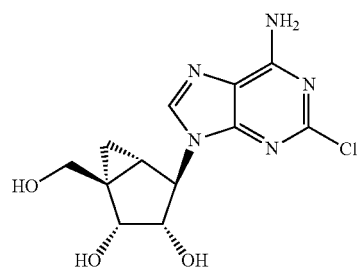 [SMILES: Nc1nc(Cl)nc2c1ncn2[C@H]1[C@H](O)[C@H](O)[C@]2(CO)C[C@H]12]

or a pharmaceutically acceptable salt thereof.

In some embodiments, the addiction is to a substance or drug having abuse potential selected from alcohol, nicotine, a narcotic, a prescription drug, or a recreational drug.

In some embodiments, the substance or drug having abuse potential is selected from a stimulant, a depressant, a cannabinoid agonist, or an opioid agonist.

In some embodiments, the substance or drug having abuse potential is selected from heroin, cocaine, alcohol, nicotine, an inhalant (e.g., bronchodilator such as a beta-agonist, or a corticosteroid or steroid), a barbiturate, a benzodiazepine, a prescription opioid agonist analgesic, nicotine, an amphetamine, or an analogue, salt, composition, or a combination thereof.

In some embodiments, the substance or drug having abuse potential is selected from alcohol, nicotine, heroin, cocaine, tetrahydrocannabinol (THC), amobarbital, allobarbital, aprobarbital, alphenal, barbital, brallobarbital, pentobarbital, phenobarbital, secobarbital, mephobarbital, butabarbital, tuinal, diazepam (Valium), alprazolam, lorazepam, clonazepam, zolpidem, bupropion, cathinone, MDMA, amphetamine, methamphetamine, dextroamphetamine, methylphenidate, opium, morphine, oxycodone, codeine, methadone, meperidine, oxymorphone, hydrocodone, tramadol, carfentanil, hydromorphone, or fentanyl, or a pharmaceutically acceptable salt or analogue thereof, or a combination thereof.

In some embodiments, the subject has an alcohol or nicotine addiction.

In some embodiments, the subject is a polydrug abuser, e.g. nicotine and alcohol addict or opioid and cannabinoid addict.

In some embodiments, the method at least partially reverses loss of glutamate uptake into astrocytes caused by the addiction.

In some embodiments, the method increases energy metabolism mediated by astrocytes, glia, microglia, neurons, endothelium cells, or other cells of the brain and/or central nervous system (CNS).

In some embodiments, the method treats or prevents a relapse of an addiction or addictive behavior in the subject.

In some embodiments, the compound decreases withdrawal symptoms in an addicted individual in withdrawal.

In one aspect, the present invention provides a method of preventing, ameliorating, treating, or promoting recovery from an addictive behavior, behavioral addiction, brain reward system disorder, compulsive disorder, or related condition, comprising administering to a subject in need thereof an effective amount of a compound selected from:

or or a pharmaceutically acceptable salt thereof.

In some embodiments, the compound is or a pharmaceutically acceptable salt thereof.

In some embodiments, the compound is

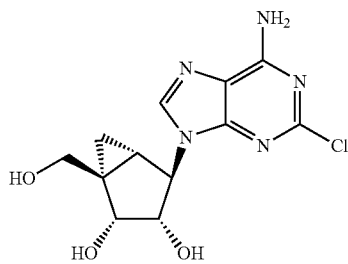 [SMILES: Nc1nc(Cl)nc2c1ncn2[C@H]1[C@H](O)[C@H](O)[C@]2(CO)C[C@H]12]

or a pharmaceutically acceptable salt thereof.

In some embodiments, the method further comprises co-administering a second drug for treating withdrawal.

In some embodiments, the addictive behavior, behavioral addiction, brain reward system disorder, compulsive disorder, or related condition is obsessive-compulsive disorder (OCD), Tourette syndrome, trichotillomania, anorexia, bulimia, anxiety disorder, psychosis, or post-traumatic stress disorder.

In some embodiments, the addictive behavior, behavioral addiction, brain reward system disorder, compulsive disorder, or related condition is selected from gambling addiction, sex addiction, pornography addiction, an eating disorder, spending addiction, rage/anger, workaholism, exercise addiction, risk-taking addictions (e.g. kleptomania and pyromania), perfectionism, internet or video game addiction, or compulsive use of an electronic device.

In some embodiments, the method at least partially reverses loss of glutamate uptake into astrocytes caused by the addiction.

In some embodiments, the method increases energy metabolism mediated by astrocytes, glia, microglia, neurons, endothelium cells, or other cells of the brain and/or central nervous system (CNS).

In some embodiments, the method treats or prevents a relapse of an addictive behavior, behavioral addiction, brain reward system disorder, compulsive disorder, or related condition in the subject.

In some embodiments, the compound is administered orally, intravenously, or parenterally. In some embodiments, the subject is a mammal, such as a human. In some embodiments, the human is an adult human.

2. Definitions

As used herein, the term "addiction" includes, unless otherwise specified, physical or psychological dependence on a substance. Addiction may involve withdrawal symptoms or mental or physical distress if the substance is withdrawn. In some embodiments, addiction includes one or more of drug liking, drug dependence, habit-formation, neurological and/or synaptic changes, development of brain reward system disorders, behavioral changes, or other signs or symptoms of addiction in a subject.

As used herein, the term "addictive drug" or "drug having abuse potential" includes drugs and other substances such as nicotine, whether approved by a regulatory body for treatment of a disease or not, that are known to result in clinical, behavioral, or neurological manifestations of addiction or compulsive behavior. In some embodiments, the addictive drug includes nicotine, a cannabinoid agonist, a stimulant, a depressant, or an opioid agonist. "Addictive substance" refers to addictive drugs as well as other substances of abuse such as alcohol. Examples of addictive substances thus include heroin, cocaine, alcohol, opiates, nicotine, inhalants, barbiturates, amphetamines, and their synthetic analogues.

3. Description of Certain Compounds of the Present Invention

In one aspect, the present invention provides compounds useful for preventing, treating, ameliorating, or promoting recovery from a disclosed disease, disorder, or condition such as an addiction. In some embodiments, the compound increases neuroprotection and neuroregeneration mediated by astrocytes. In some embodiments, the compound is selective for an $A_3$ receptor, for example selective for an $A_3$ receptor by at least 10-fold relative to other adenosine receptors; or for example more than 25-fold, 50-fold, 100-fold, 500-fold, or 1000-fold relative to other adenosine receptors. In some embodiments, the compound selectively modulates an $A_3$ receptor. In some embodiments, the compound is a selective agonist at an $A_3$ receptor. In some embodiments, the compound is a selective partial agonist at an $A_3$ receptor. In some embodiments, the compound is a dual partial agonist at both the $A_1$ and $A_3$ receptors. In some embodiments, the compound is a biased full or partial agonist. In some embodiments, the compound is a biased full or partial antagonist.

In further embodiments, the compound is selective for a $P2Y_1$ receptor, for example selective for $P2Y_1$ receptors by at least 10-fold relative to other P2Y receptors; or for example more than 25-fold, 50-fold, 100-fold, 500-fold, or 1000-fold relative to other P2Y receptors. In some embodiments, the compound selectively modulates a $P2Y_1$ receptor. In some embodiments, the compound is a selective agonist at a $P2Y_1$ receptor. In some embodiments, the compound is a selective partial agonist at a $P2Y_1$ receptor. In some embodiments, the compound is a biased full or partial agonist. In some embodiments, the compound is a biased full or partial antagonist.

The term "biased" refers to compounds that preferentially modulate, activate, agonize, or antagonize one or more, but not all, of the pathways associated with a receptor.

Without wishing to be bound by theory, it is believed that biased full or partial agonism or antagonism allows for selective modulation of one or more pathways linked to an $A_3$ or $P2Y_1$ receptor, which may lead to improved treatment of a disease or condition and avoidance of undesired pathway modulation (which would lead to side effects). In some embodiments, selective modulation preferentially activates astrocytes as disclosed herein. Accordingly, in some embodiments, a disclosed compound is a biased full or partial agonist or antagonist of one or more G-coupled or G-independent pathways linked to the adenosine $A_3$ receptor or $P2Y_1$ receptor. In some embodiments, the compound selectively modulates a pathway mediated by $A_3$ or a $P2Y_1$ receptor, such as beta-arrestin activation, intracellular calcium mobilization, cAMP modulation, ATP-dependent potassium channel activation, or ERK1/2 phosphorylation, or other downstream cellular activities associated with such pathways. In some embodiments, the pathway increases or is related to neuroprotection or neurorestoration. In some embodiments, the compound is selected from a (N)-methanocarba nucleoside such as AST-004; or a pharmaceutically acceptable salt thereof.

The term "methanocarba nucleoside" as used herein refers to a nucleoside analog in which the oxygen present in the tetrahydrofuran ring of the ribose sugar is replaced with a methylene unit and the resulting carbocyclic ring is fused to a cyclopropyl ring to form a bicyclo[3.1.0]hexane, such as the structures

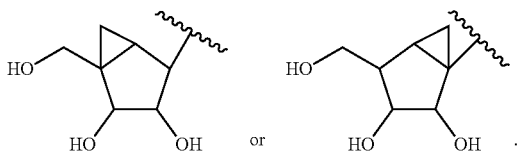 [SMILES: *C1C(O)C(O)C2(CO)CC12 ; *C12CC1C(CO)C(O)C2O]

Without being bound by theory, it is believed that methanocarba nucleosides mimic a sugar conformation or pseudo-conformation believed to be favored by certain receptor subtypes. In some embodiments, North methanocarba nucleosides are those that mimic or prefer a C3'-endo/C2'-exo sugar conformation and South methanocarba nucleosides are those that mimic or prefer a C3'-exo/C2'-endo conformation. In some embodiments, a (N)-methanocarba ("North" methanocarba) sugar has the following structure:

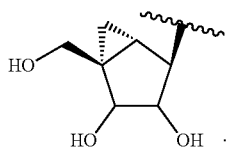

In some embodiments, a (N)-methanocarba sugar has the following structure:

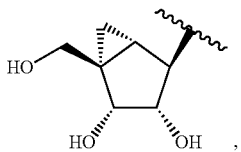

referred to herein as a "D-(N)-methanocarba sugar." In other embodiments, a methanocarba sugar is in the South, or (S)-methanocarba, configuration. In some embodiments, such methanocarba sugars are represented by the structure:

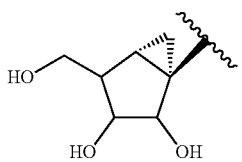

In some embodiments, a (S)-methanocarba sugar has the following structure:

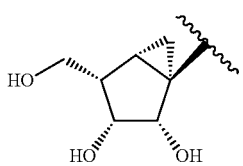

referred to herein as a "D-(S)-methanocarba sugar."

In some embodiments, the compound is functionally selective at the $A_3$ or $P2Y_1$ receptor, i.e., selectively discriminates among pathways mediated by $A_3$ or a $P2Y_1$ receptor, for example by modulating one or more pathways but not others, or by activating one or more pathways and deactivating one or more other pathways. In some embodiments, the compound is an antagonist as measured by cAMP signaling, but a partial agonist for β-arrestin recruitment. In other embodiments, the compound is an agonist of Gq/11-mediated $Ca^{2+}$ mobilization and a partial agonist or antagonist of arrestin recruitment. In some embodiments, the present invention provides a method of treating or promoting recovery from an addiction, addictive behavior, behavioral addiction, brain reward system disorder, compulsive disorder, or related condition, via biased or functionally selective $A_3$ receptor modulation (e.g., by selective agonism or antagonism among pathways such as those mentioned above, for example glutamate uptake), comprising administering an effective amount of a disclosed compound to a patient in need thereof. In some embodiments, the compound is selected from DMPA, CCPA, MRS1760, or MRS542 (see Verzijl D, et al., "Functional selectivity of adenosine receptor ligands," Purinergic Signaling 7: 171-192 (2011)). In some embodiments, the compound is DBXRM. In some embodiments, the compound is selected from a (N)-methanocarba nucleoside such as AST-004 or MRS1873 (AST-008); or a pharmaceutically acceptable salt thereof.

It has been surprisingly found that certain purine nucleoside mono-, di-, and tri-phosphates, such as those described in detail herein, are rapidly dephosphorylated in vivo, possibly by ectonucleotidases, enzymes responsible for the dephosphorylation of nucleotides that are present both on the surface of cell membranes and circulating in blood and plasma (See Ziganshin et al. Pflugers Arch. (1995) 429:412-418). It is often extremely difficult to predict which nucleotide analogues will be substrates for ectonucleotidases and will thus be expected to be dephosphorylated in vivo. In some embodiments, the dephosphorylated compound is responsible for the therapeutic efficacy. Thus, in some embodiments the corresponding, phosphorylated mono-, di-, or triphosphate, or a phosphate ester such as an alkyl or phenyl ester thereof, is a prodrug or precursor to the agent responsible for the therapeutic effect.

In some embodiments, compounds of the present invention are able to cross the blood-brain barrier (BBB). The term "blood-brain barrier" or "BBB," as used herein, refers to the BBB proper as well as to the blood-spinal barrier. The blood-brain barrier, which consists of the endothelium of the brain vessels, the basal membrane and neuroglial cells, acts to limit penetration of substances into the brain. In some embodiments, the brain/plasma ratio of total drug is at least approximately 0.01 after administration (e.g. oral or intravenous administration) to a patient. In some embodiments, the brain/plasma ratio of total drug is at least approximately 0.03. In some embodiments, the brain/plasma ratio of total drug is at least approximately 0.06. In some embodiments, the brain/plasma ratio of total drug is at least approximately 0.1. In some embodiments, the brain/plasma ratio of total drug is at least approximately 0.2.

Prototypical adenosine $A_3$ receptor agonists such as Cl-IB-MECA and MRS5698 are low-solubility, lipophilic compounds with c Log P values typically >2. This lipophilicity is a major factor contributing to these compounds' high plasma protein binding, high brain binding and resulting low free fraction of drug available to interact with the $A_3$ receptor in the brain. In some embodiments, a disclosed compound such as AST-004 or MRS1873 (AST-008) is selected that has physicochemical properties that are substantially different; these and related compounds are hydrophilic compounds with c Log P<0, resulting in high solubility, low plasma and brain binding and high unbound drug concentrations available to interact with the $A_3$ receptor.

Accordingly, in some embodiments the compound has a c Log P less than about 0.8, about 0.7, about 0.6, about 0.5, about 0.4, about 0.3, about 0.2, about 0.1, about 0.05, about 0.01, or about 0.005. In some embodiments, the compound has a c Log P less than about 0, such as less than about −0.1, −0.2, −0.3, −0.4, −0.5, −0.6, −0.7, −0.8, or −0.9 or less. In some embodiments, the compound has an unbound fraction in plasma of about 0.5 to 0.9. In some embodiments, the compound has an unbound fraction in plasma of about 0.6 to 0.85, 0.7 to 0.8, or about 0.75. In some embodiments, the compound has an unbound fraction in brain of at least about 0.02, or at least about 0.03, 0.04, 0.05, 0.06, 0.07, 0.08, 0.09, 0.1, 0.12, 0.15, or 0.17 or greater. In some embodiments, the compound has an unbound fraction in plasma of about 0.6 to 0.85, 0.7 to 0.8, or about 0.75 and/or at least 0.08 unbound fraction in brain.

Compounds of the invention may be prepared using methods known in the art, using no more than routine experimentation. For example, certain compounds of the invention may be prepared following the procedures provided in U.S. Pat. No. 7,087,589 (and references cited therein), which is hereby incorporated by reference.

In some embodiments, the compound is selected from adenosine, ADP, 2-methylthio-ADP trisodium salt, ATP, ATP disodium salt, α,β-methylene ATP, α,β-methyleneadenosine 5'-triphosphate trisodium salt, 2-methylthioadenosine triphosphate tetrasodium salt, 2-MeSATP, BzATP triethylammonium salt, inosine, cytidine, acylated cytidines, cytidine-monophosphate (CMP), cytidine diphosphate (CDP), cytidine triphosphate (CTP), CDP-choline, CMP-choline, denufosol, denufosol tetrasodium, GTP, ITP, MRS 541, MRS 542, MRS 1760, MRS 2179, MRS 2279, MRS 2341, MRS 2365, MRS 2500, MRS 2690, MRS 2698, MRS 3558, MRS 4322, MRS 5151, MRS 5676, MRS 5678, MRS 5697, MRS 5698, MRS 5923, MRS 5930, Benzyl-NECA, IB-MECA, Cl-IB-MECA, LJ529, DPMA, CCPA, DBXRM, HEMADO, PEMADO, HENECA, PENECA, CP608,039, CP532,903, CGS21680, AR132, VT72, VT158, VT160, VT163, PSB 0474, uridine 5'-diphosphate (UDP), UDP-glucose, uridine β-thiodiphosphate (UDPRS), uridine 5'-triphosphate (UTP), uridine γ-thiophosphate (UTPγS), 2-thio-UTP tetrasodium salt, UTPγS trisodium salt, uridine-5'-diphosphoglucose, diuridine triphosphate, 2-(hexylthio) (HT)-AMP, diadenosine pentaphosphate, 2'-deoxy-2'-amino-UTP, 2-thio-UTP, triacetyluridine, diacetyl/acyl uridine, uridine, suramin, dipyridamole analogues, diadenosine tetraphosphate Ap$_4$U, Ap$_4$A, INS365, INS37217, or INS48823; wherein each sugar may be replaced with a methanocarba sugar in the North or South conformation or each sugar may be replaced with a D-ribosugar; or a pharmaceutically acceptable salt thereof.

In some embodiments, 2-methylthio-ADP or a pharmaceutically acceptable salt thereof is useful in the methods of the present invention. Without wishing to be bound by theory, it is believed that 2-MeS ADP is rapidly hydrolyzed to 2-methylthioadenosine in vivo, where it is a biased agonist, partial agonist, or biased partial agonist of $A_3R$. 2-methylthioadenosine is believed to have receptor binding very similar to that of AST-004.

In some embodiments, the compound is an $A_3R$ agonist such as $N^6$-benzyladenosine-5'-N-methyluronamides such as $N^6$-(3-iodobenzyl)-adenosine-5'-N-methyluronamide, also known as IB-MECA or Can-Fite CF-101, or 2-Chloro-$N^6$-(3-iodobenzyl)-adenosine-5'-N-methyluronamide (also known as 2-Cl-IB-MECA or Can-Fite CF-102; (N)-methanocarba nucleosides such as (1R,2R,3S,4R)-4-(2-chloro-6-((3-chlorobenzyl)amino)-9H-purin-9-yl)-2,3-di-hydroxy-N-methylbicyclo[3.1.0]hexane-1-carboxamide (also known as CF502, Can-Fite Biopharma, MA); (2S,3S,4R,5R)-3-amino-5-[6-(2,5-dichlorobenzylamino)purin-9-yl]-4-hydroxy-tetrahydrofuran-2-carboxylic acid methylamide (also known as CP532,903); (1'S,2'R,3'S,4'R,5'S)-4-(2-chloro-6-(3-chlorobenzylamino)-9H-purin-9-yl)-2,3-dihydroxy-N-methylbicyclo[3.1.0]hexane-1-carboxamide (also known as MRS3558), 2-(1-hexynyl)-N-methyladenosine; (1S,2R,3S,4R)-2,3-dihydroxy-4-(6-((3-iodobenzyl)amino)-4H-purin-9(5H)-yl)-N-methylcyclopentanecarboxamide (also known as CF101, Can-Fite); (1S,2R,3S,4R)-4-(2-chloro-6-((3-iodobenzyl)amino)-4H-purin-9(5H)-yl)-2,3-dihydroxy-N-methylcyclopentanecarboxamide (also known as CF102, Can-Fite); (1'R,2'R,3'S,4'R,5'S)-4-{2-chloro-6-[(3-iodophenylmethyl)amino]purin-9-yl-}-1-(methylaminocarbonyl)-bicyclo[3.1.0]hexane-2,3-diol (also known as MRS1898); or 2-dialkynyl derivatives of (N)-methanocarba nucleosides; or a pharmaceutically acceptable salt thereof. In some embodiments, the compound is selected from IB-MECA (also known as CF101), or Cl-IB-MECA (also known as CF102); or a pharmaceutically acceptable salt thereof. In some embodiments, the compound is selected from a (N)-methanocarba nucleoside such as those disclosed above; or a pharmaceutically acceptable salt thereof.

Also included are $A_3R$ allosteric modulators which enhance the receptor activity in the presence of the native ligand, such as 2-cyclohexyl-N-(3,4-dichlorophenyl)-1H-imidazo[4,5-c]quinolin-4-amine (also known as CF602, Can-Fite). However, the above-listed $A_3R$ agonists are by no means exclusive and other such agonists may also be used. The administration of $A_3R$ agonists covalently bound to polymers is also contemplated. For example, $A_3R$ agonists may be administered in the form of conjugates where an agonist is bound to a polyamidoamine (PAMAM) dendrimer.

Without wishing to be bound by theory, it is believed that full or partial agonism, including biased agonism, by certain uridine analogues will allow for selective modulation of one or more pathways which may lead to improved treatment of a disclosed disease or condition and avoidance of undesired pathway modulation (which would lead to side effects). In some embodiments, selective modulation preferentially activates astrocytes or other glial cells such as microglia and oligodendrocytes. Certain uridine analog compounds suitable for use in the present invention are disclosed in WO 2014/160502, which is hereby incorporated by reference in its entirety. In some embodiments, the compound is an $A_3R$ agonist. In some embodiments, the compound is a $P2Y_1$ receptor agonist. In some embodiments, the compound is a biased agonist at an adenosine receptor, such as an $A_1$, A2A, A2B or $A_3$ receptor. In some embodiments, the compound is a biased agonist, partial agonist, or biased partial agonist at an $A_3$ receptor. In some embodiments, the compound is a biased agonist, partial agonist, or biased partial agonist at a $P2Y_1$ receptor. In some embodiments, the compound is selected from the group consisting of:

1
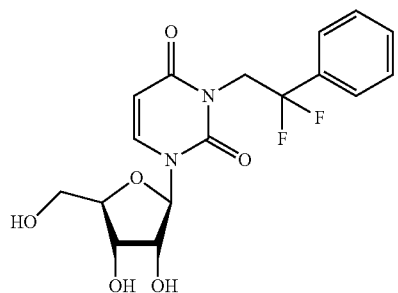
2
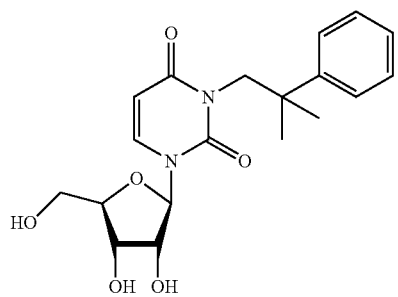
3
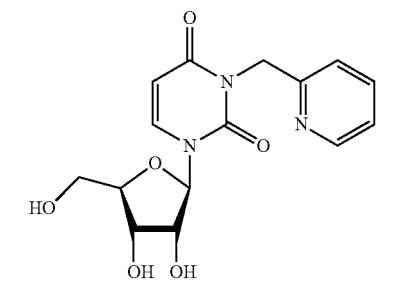
4
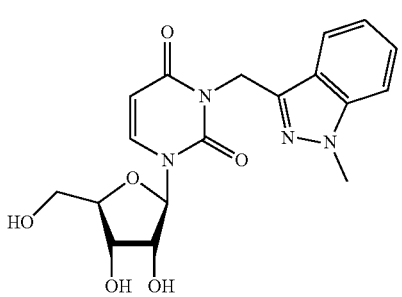
5
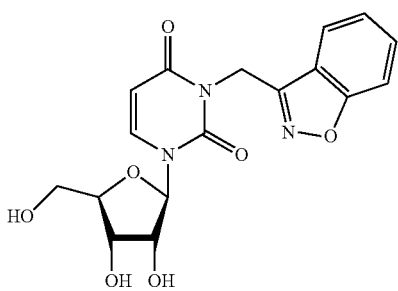
6
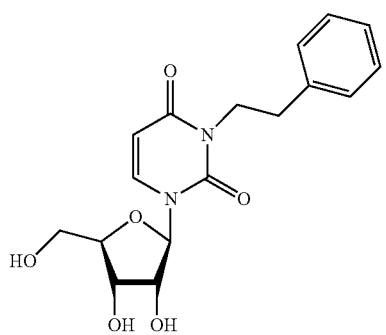
7
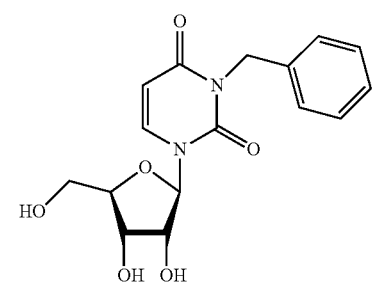
8
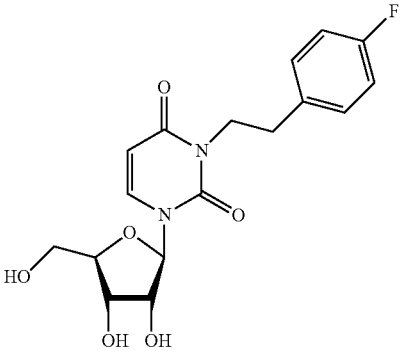
9
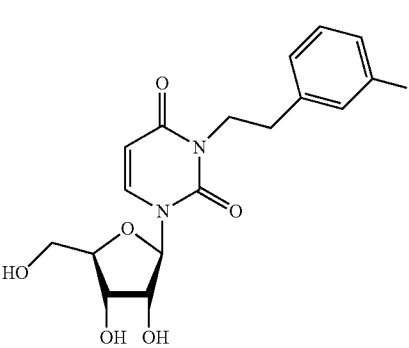
10
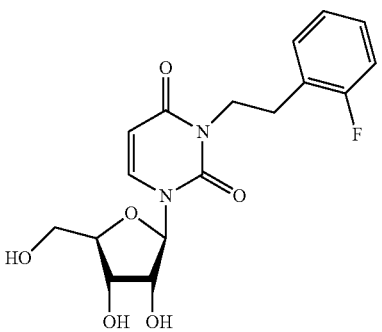

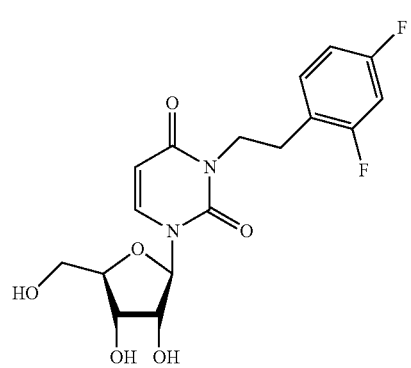
11
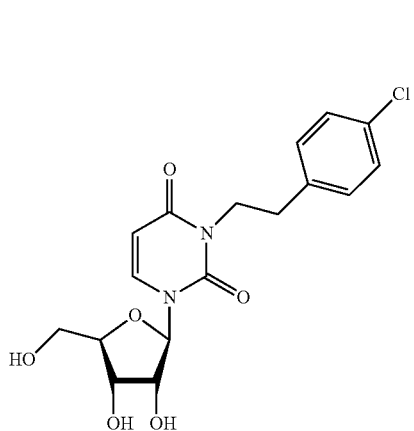
12
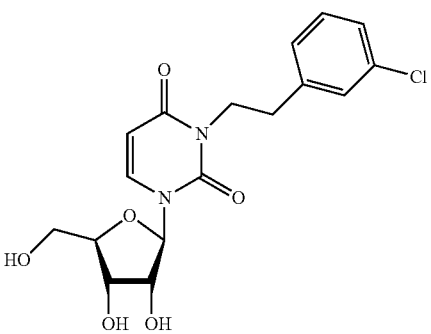
13
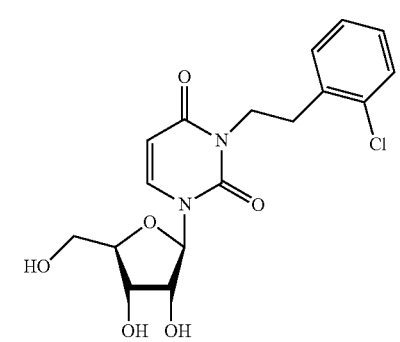
14
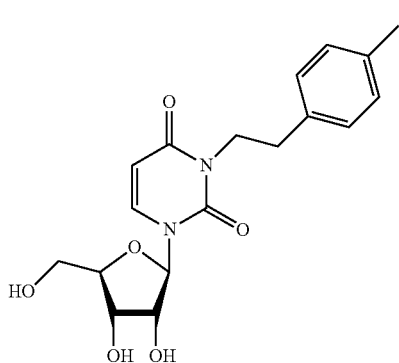
15
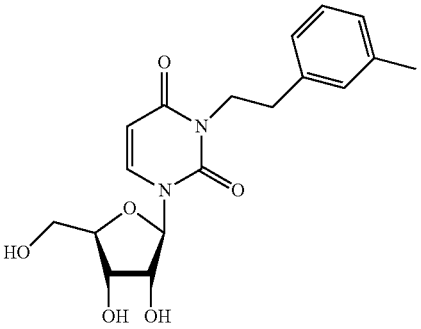
16
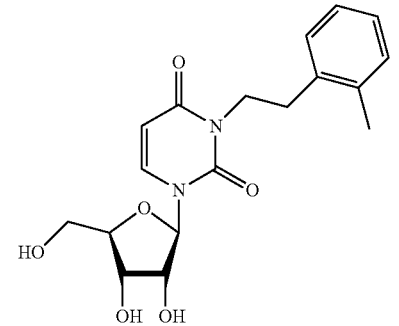
17
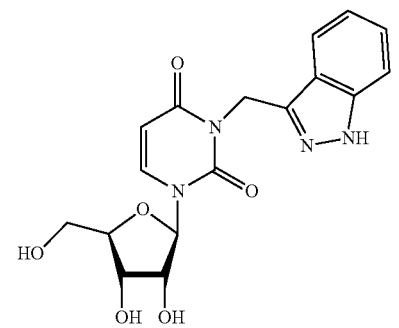
18
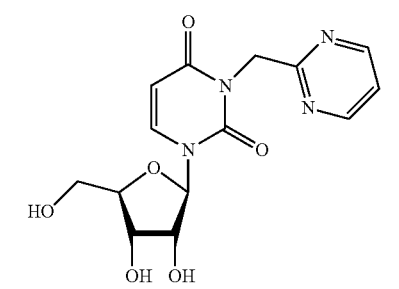
19

20
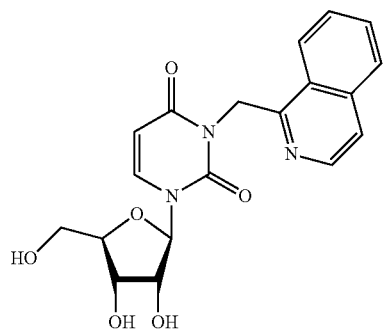
21
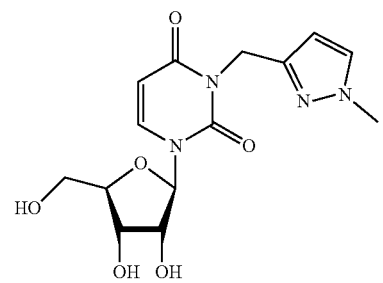
22
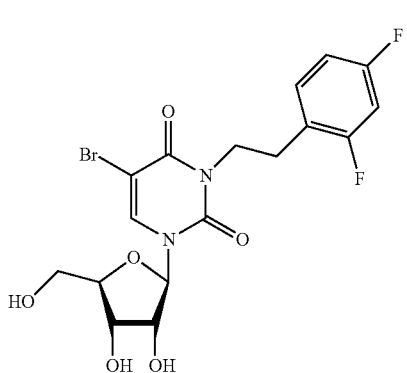
23
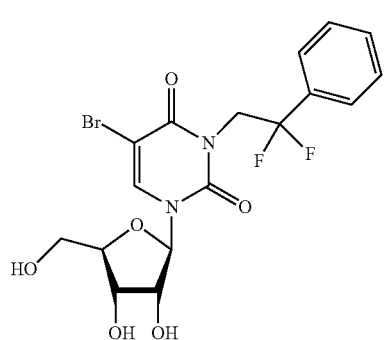
24
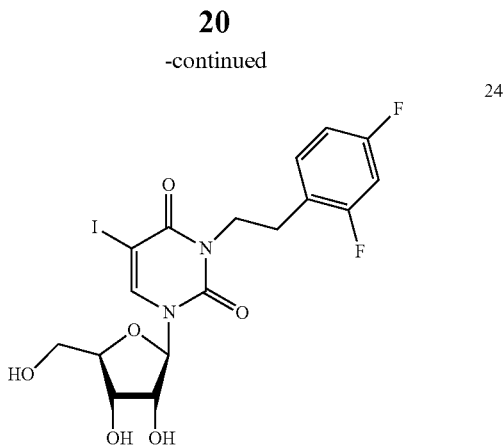
25
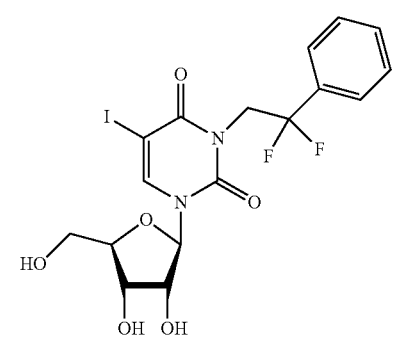
26
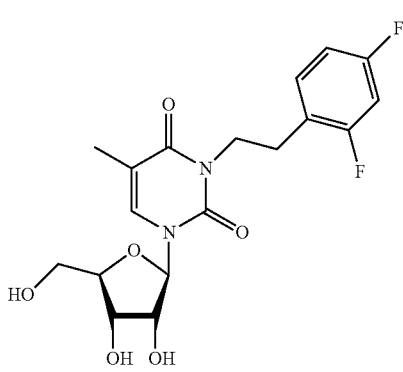
27
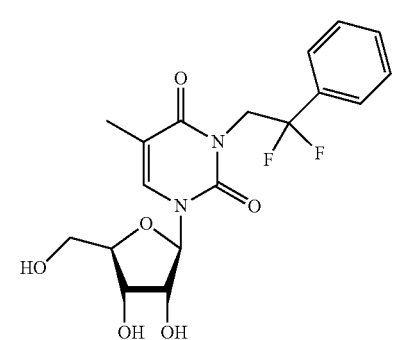

28
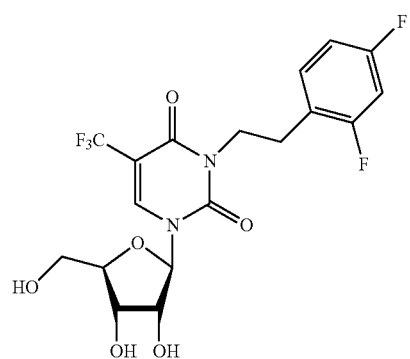
29
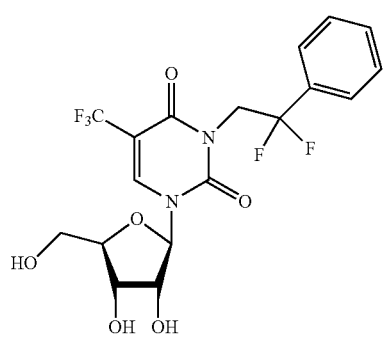
30
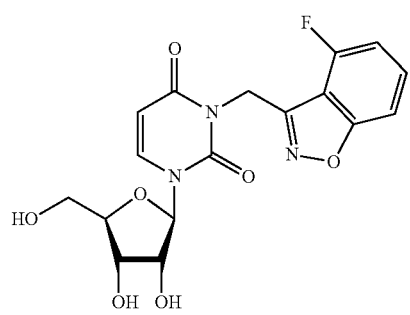
31
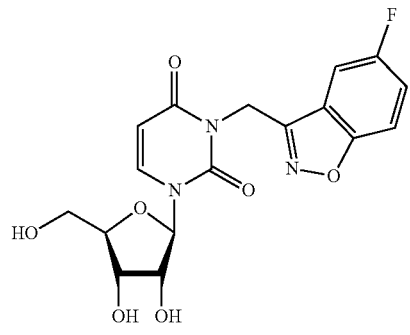
32
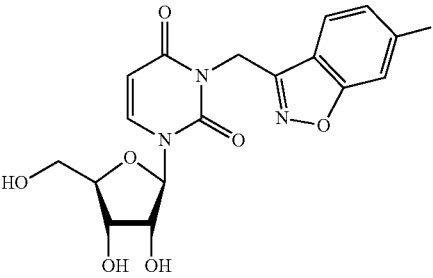
33
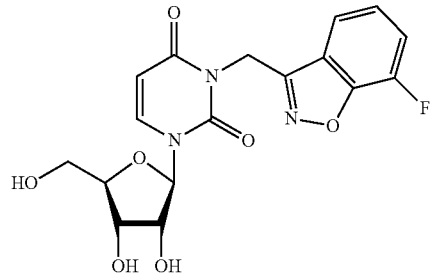
34
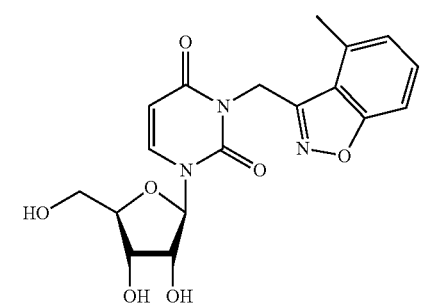
35
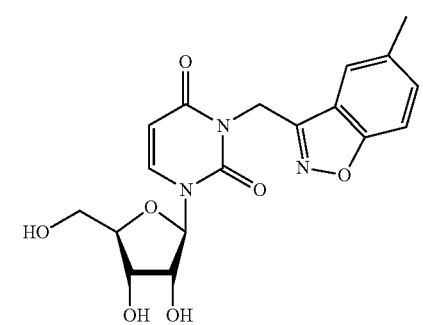
36
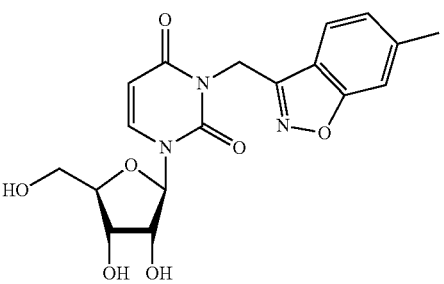
37
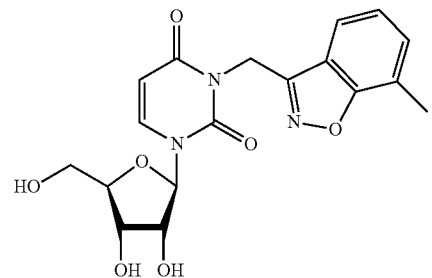

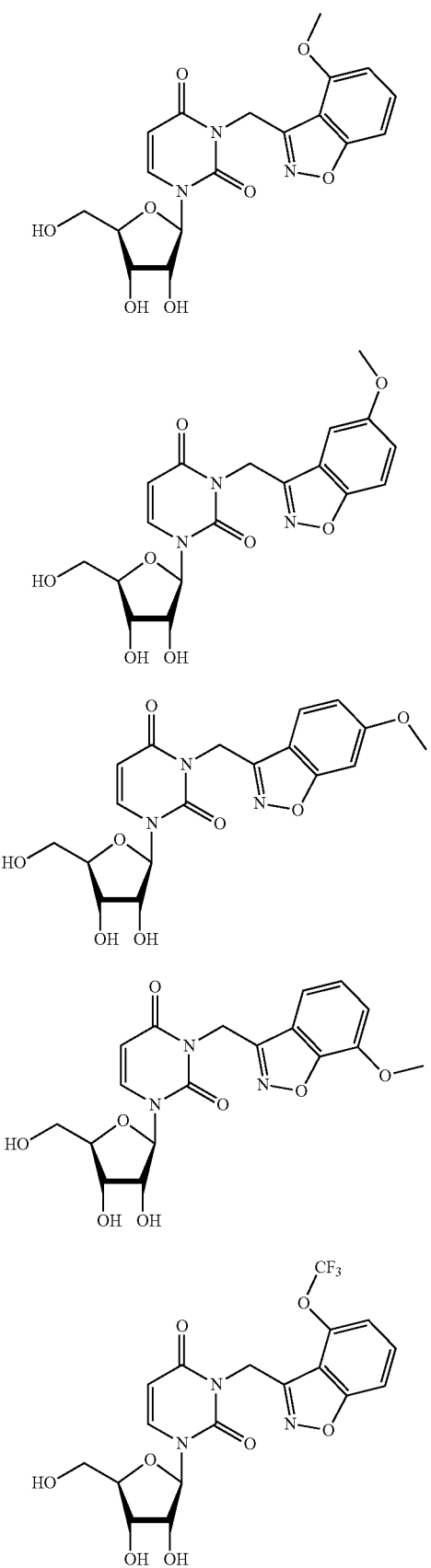
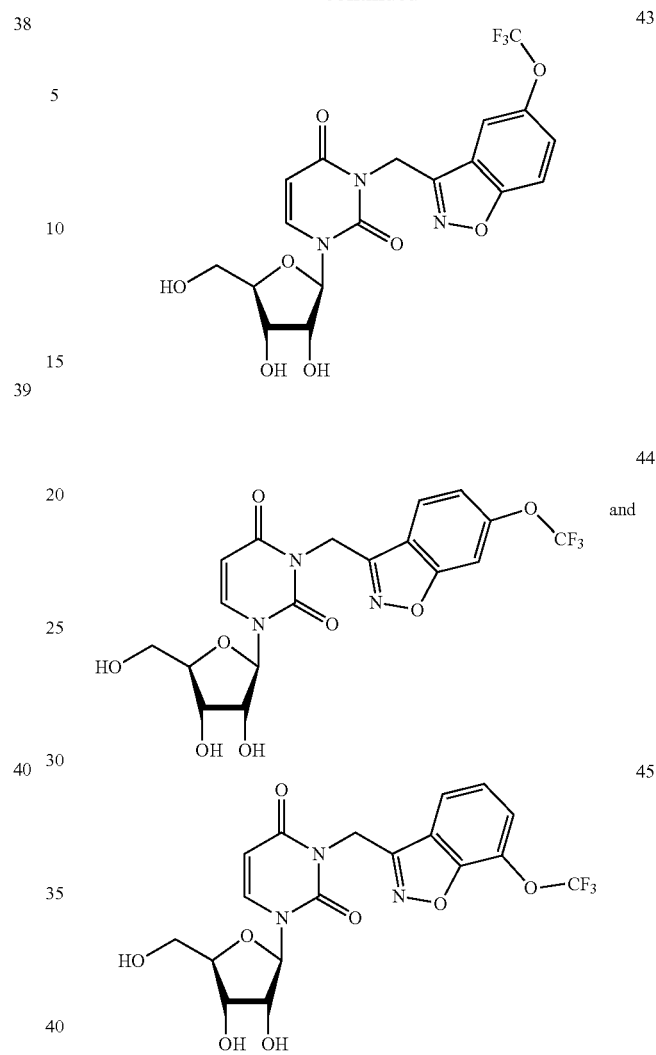
or a phosphorylated analog thereof; or a pharmaceutically acceptable salt thereof.
In some embodiments, the compound is selected from:
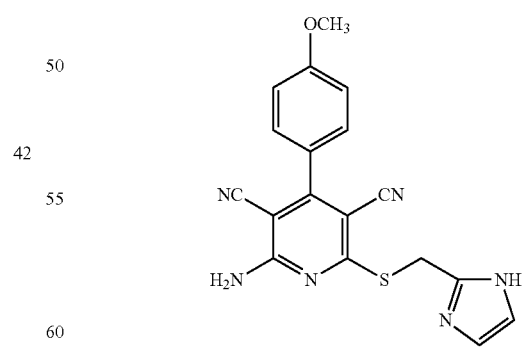
(see Beukers M W et al., (2004) "New, non-adenosine, high-potency agonists for the human adenosine A2B receptor with an improved selectivity profile compared to the reference agonist N-ethylcarboxamidoadenosine," *J. Med. Chem.*

Devine 2010 #7b

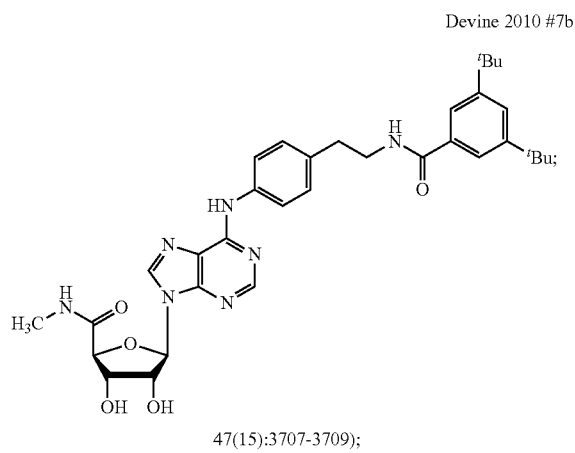

47(15):3707-3709);

Devine 2010

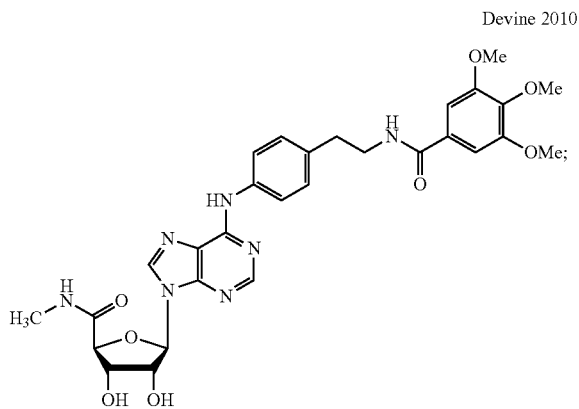

Devine 2010 #9a

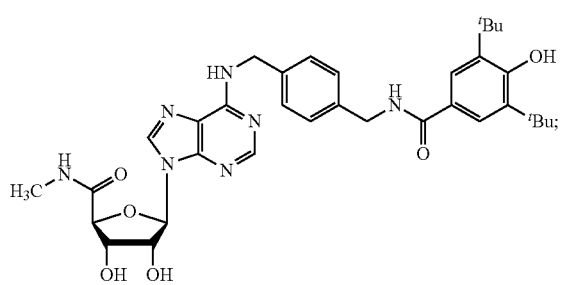

Devine 2010 #9b

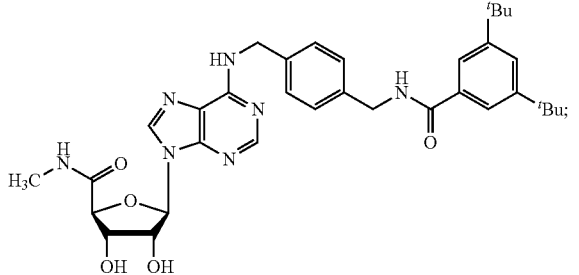

Devine 2010 #9c

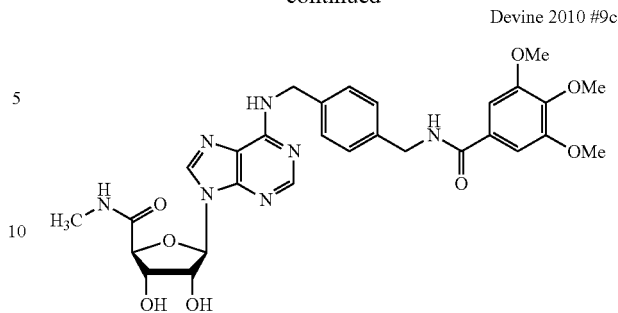

(see Devine S M et al. "Synthesis and Evaluation of new A3R agonists," Bioorg Med Chem 18, 3078-3087. 2010; and Muller C E, Jacobson K A. "Recent Developments in adenosine receptor ligands and their potential for novel drugs." Biochimica et Bionhysica Acta 1808. 1290-1308. 20111:

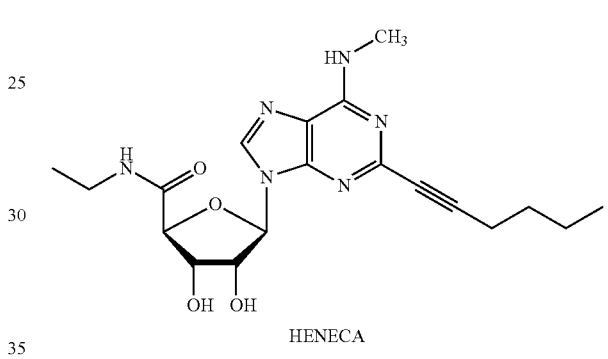

HENECA (see Ben D D et al. "Different efficacy of adenosine and NECA derivatives at the human A3 receptor: Insight into the receptor activation switch," Biochem Pharm 87, 321-331. 2014; and Camaioni E, Di Francesco E, Vittori S, Volpini R, Cristalli G. "Adenosine receptor agonists: synthesis and biological evaluation of the diastereoisomers of 2-(3-hydroxy-3-phenyl-1-propyn-1-yl)NECA," Bioorg Med Chem 1997; 5:2267-75);

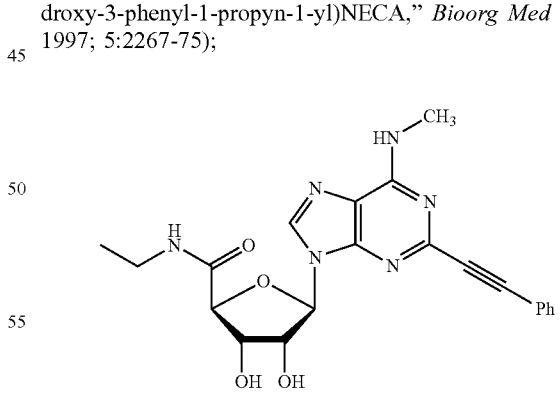

PENECA (see Klotz, K. N. "2-Substituted N-ethylcarboxamidoadenosine derivatives as high-affinity agonists at human A3 adenosine receptors," Naunyn Schmiedebergs Arch Pharmacol. 1999 August; 360(2):103-8; and Cristalli G et al. (1995) "2-Aralkynyl and 2-heteroalkynyl derivatives of adenosine-5'-N-ethyluronamide as selective A2a adenosine receptor agonists," J Med Chem 38:1462-1472);

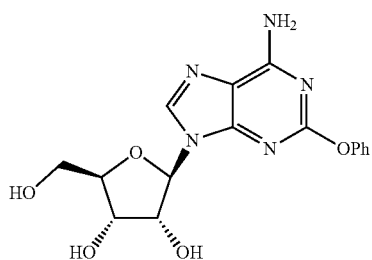 [SMILES: Nc1nc(Oc2ccccc2)nc2c1ncn2[C@@H]1O[C@H](CO)[C@@H](O)[C@H]1O]

(see Kim S et al. "3D quantitative SAR at A3R," *J Chem Inf Model* 47, 1225-1233 2007);

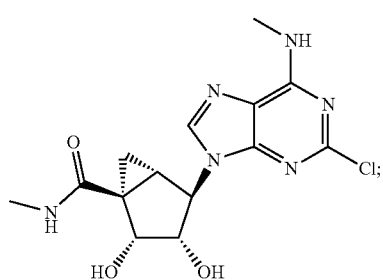

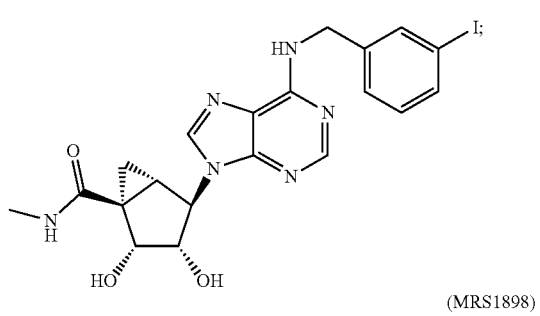

(MRS1898)

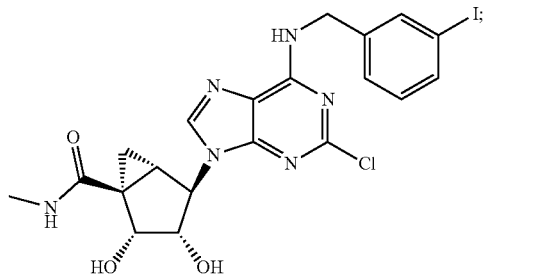

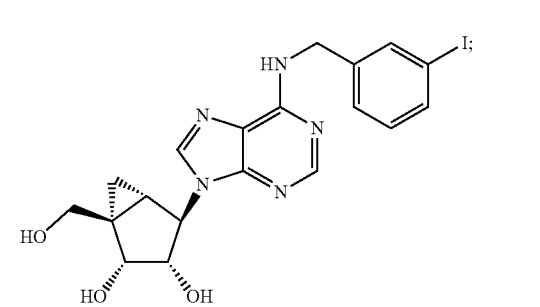

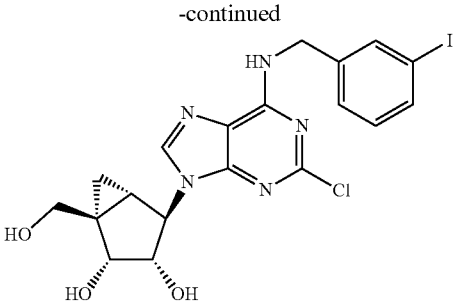

(see Lee, K. et al. "Ring-Constrained (N)-Methanocarba Nucleosides as Adenosine Receptor Agonists," *Bioorg Med Chem Lett* 2001, 1, 1333-1337);

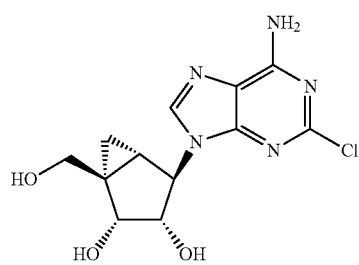 [SMILES: Nc1nc(Cl)nc2c1ncn2[C@H]1[C@H](O)[C@H](O)[C@]2(CO)C[C@H]12]

(see Kenneth A. Jacobson et al. Chapter 6. A3 Adenosine Receptor Agonists: History and Future Perspectives pp 96-97. Book—Springer: A3 Adenosine Receptors from Cell Biology to Pharmacology and Therapeutics, 2009);

(see Lee K et al. "Ring-Constrained (N)-Methanocarba Nucleosides as Adenosine Receptor Agonists," *Bioorg Med Chem Lett* 2001, 11, 1333-1337; and Gao et al. "Structural Determinants of A3R Activation: Nucleoside Ligands at the Agonist/Antagonist Boundary," *J Med. Chem.*, 2002, 45, 4471-4484);

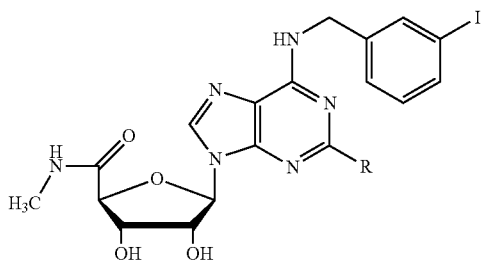

R = H: IB-MECA (CF101)
R = Cl: Cl-IB-MECA (CF102)

(see Muller C E, Jacobson K A, "Recent Developments in adenosine receptor ligands and their potential for novel drugs," Biochimica et Biophysica Acta 2011, 1808, 1290-1308);

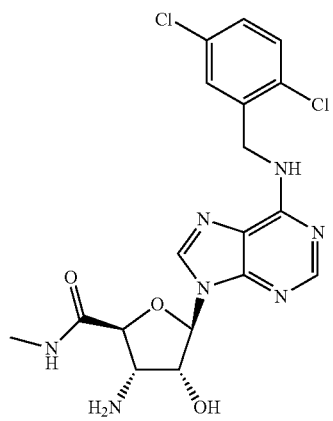

CP532,903 (see Tracey W R et al. "Novel n6-substituted adenosine 5'-N-methyluronamides with high selectivity for human A3R reduce ischemic myochardial injury," Am J Physiol Heart Circ Physiol 285. 2003; Muller C E, Jacobson K A, "Recent Developments in adenosine receptor ligands and their potential for novel drugs," Biochimica et Biophysica Acta 1808, 1290-1308. 2011; and Wan T C et al. "The A3R Agonist CP-532,903 Protects against Myocardial Ischemia/Reperfusion Injury," J. of Pharmacology and Exptl Therapies 324, 1. 2008);

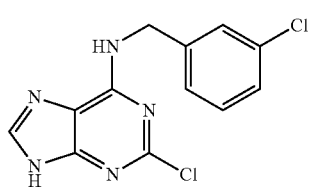 [SMILES: Clc1cccc(CNc2nc(Cl)nc3[nH]cnc23)c1]

(MRS5930; see Jacobson K A et al. "John Daly Lecture: Structure-guided Drug Design for Adenosine and P2Y Receptors," Comp. and Struct. Biotechnology Jour 13. 286-298. 2015);

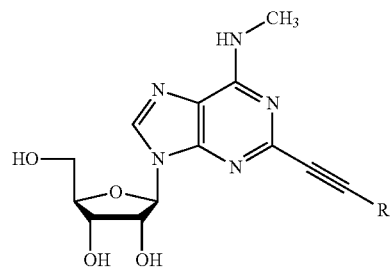

R = nC$_4$H$_9$: HEMADO
R = Ph: PEMADO (see Volpini R et al. "HEMADO as Potent and Selective Agonists of hA3R," J Med Chem 45, 3271-3279. 2002; Muller C E et al. "Recent Developments in adenosine receptor ligands and their potential for novel drugs," Biochimica et Biophysica Acta 1808, 1290-1308. 2011; and Volpini R et al. "Synthesis and Evaluation of Potent and Highly Selective Agonists for hA3R," J of Med Chem 52, 7897-7900. 2009);

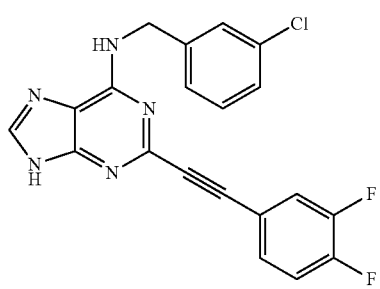 [SMILES: Fc1ccc(C#Cc2nc(NCc3cccc(Cl)c3)c3nc[nH]c3n2)cc1F]

(MRS5923; see Jacobson K A et al. "John Daly Lecture: Structure-guided Drug Design for Adenosine and P2Y Receptors," Comp. and Struct. Biotechnology Jour 13. 286-298. 2015);

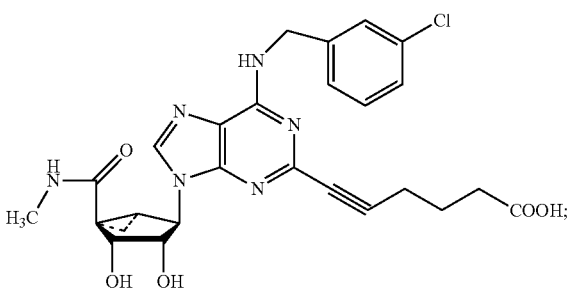

MRS5151

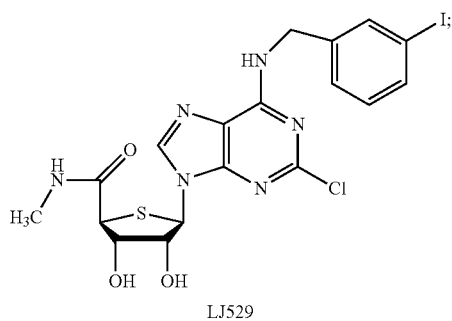

LJ529

(see Muller C E, Jacobson K A. "Recent Developments in adenosine receptor ligands and their potential for novel drugs," Biochimica et Biophysica Acta 1808, 1290-1308. 2011);

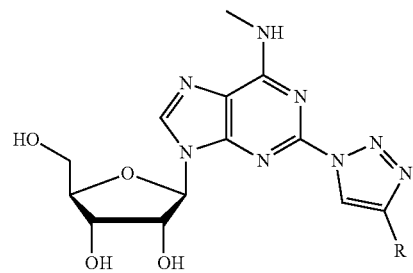

wherein R is H or cyclopentylmethyl;

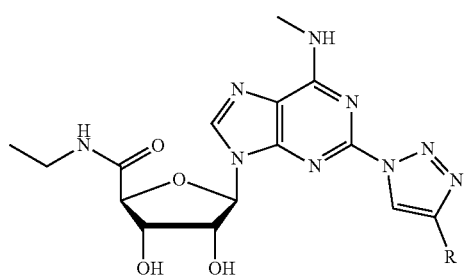

wherein R is H, butyl, or pyridin-2-yl (see Cosyn L. et al. "2-triazole-substituted adenosines," J Med Chem 2006. 49. 7373-7383);

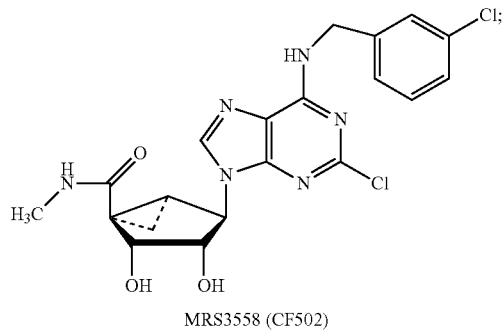

MRS3558 (CF502)

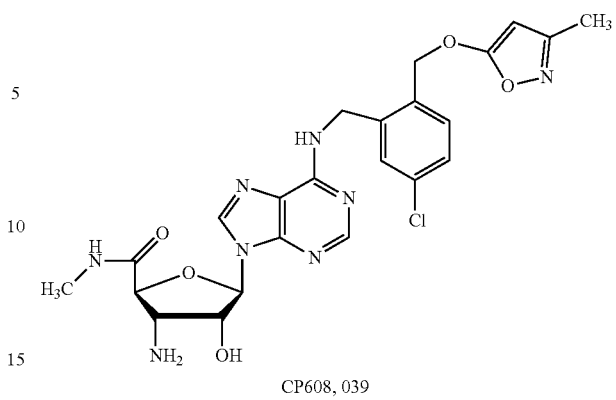

CP608, 039

(see Muller C E, Jacobson K A. "Recent Developments in adenosine receptor ligands and their potential for novel drugs," Biochimica et Biophysica Acta 1808, 1290-1308. 2011);

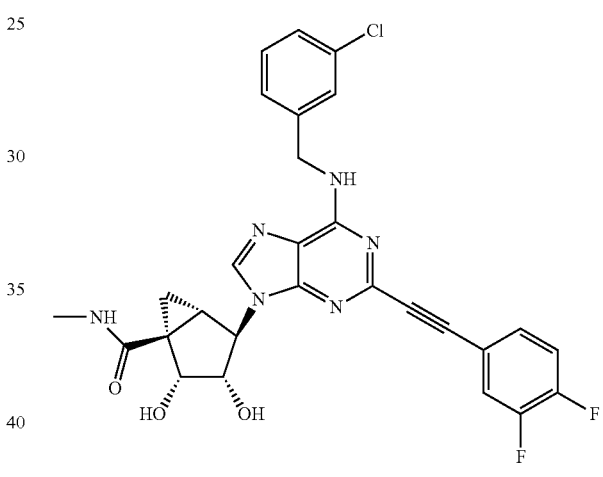

MRS5698

(see Jacobson K A et al. "John Daly Lecture: Structure-guided Drug Design for Adenosine and P2Y Receptors," Comp. and Struct. Biotechnology Jour 13. 286-298. 2015);

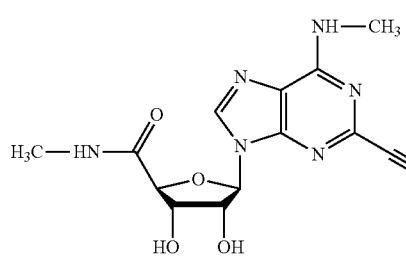

wherein Ar is selected from phenyl, p-$CH_3$CO-phenyl, p-fluorophenyl, or 2-pyridyl (see Volpini R et al. "Synthesis and Evaluation of Potent and Highly Selective Agonists for hA3R," J Med Chem 52, 7897-7900. 2009);

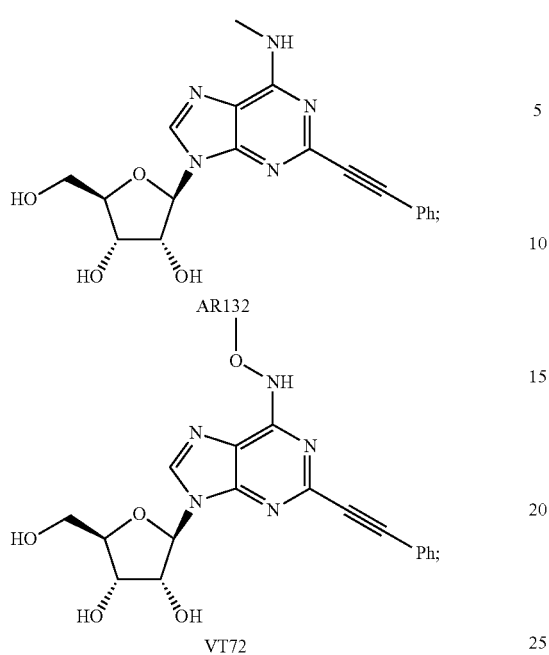
AR132
VT72
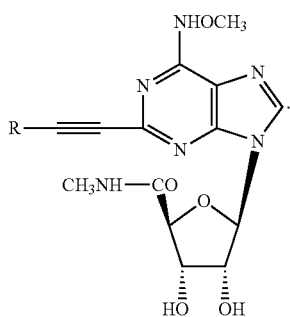
R = C6H5, VT158
R = 2-pyridinyl, VT160
R = p-C6H4COCH3, VT163
(see Pugliese A M et al., "Role of A3R on CA1 hippocampal neurotransmission during OGD," Biochem Pharmacology 74. 2007);
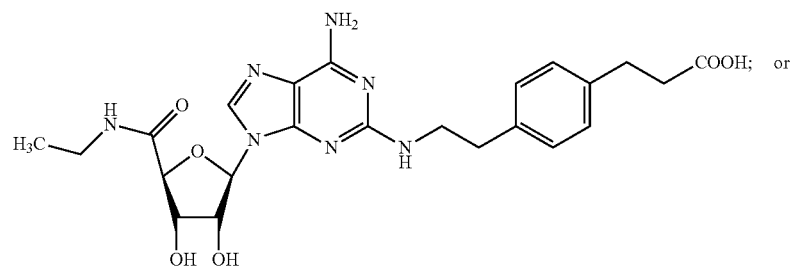
CGS21680
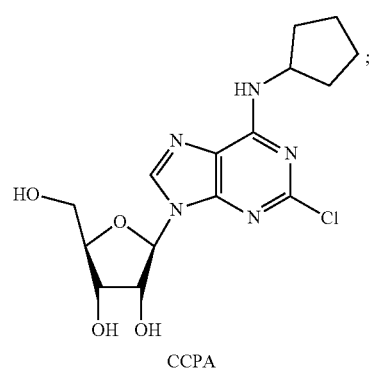
CCPA (see Klotz K N "Adenosine receptors and their ligands NS's," Arch Pharmacol. 362. 382-391. 2000); or a pharmaceutically acceptable salt thereof. In some embodiments, the compound is selected from a (N)-methanocarba nucleoside such as those disclosed above; or a pharmaceutically acceptable salt thereof.

In some embodiments, the compound is selected from:

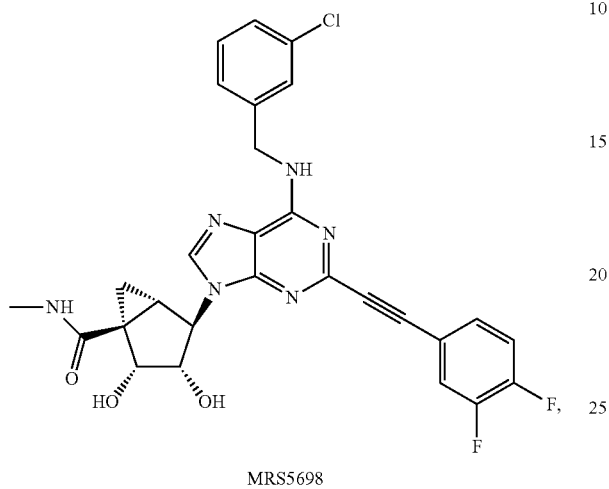

MRS5698

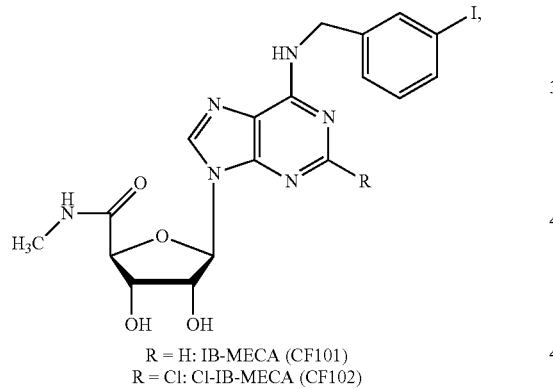

R = H: IB-MECA (CF101)
R = Cl: Cl-IB-MECA (CF102)

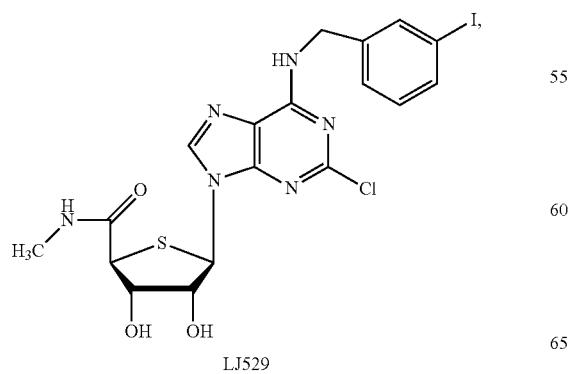

LJ529

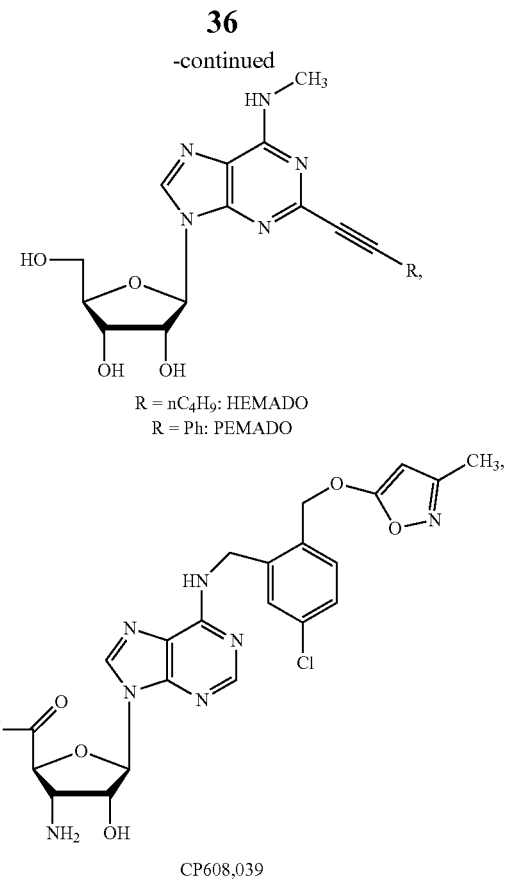

R = nC₄H₉: HEMADO
R = Ph: PEMADO

CP608,039

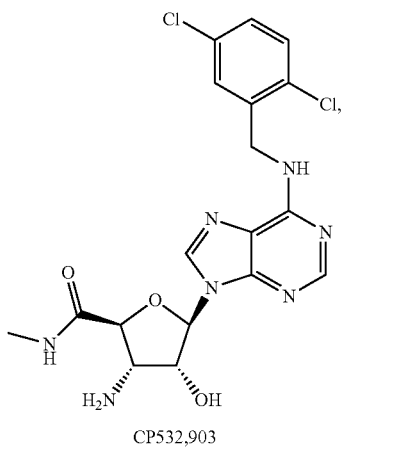

CP532,903

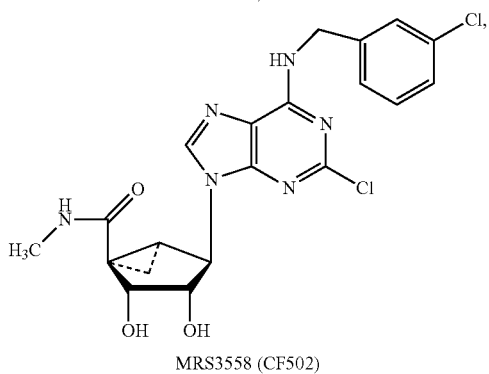

MRS3558 (CF502)

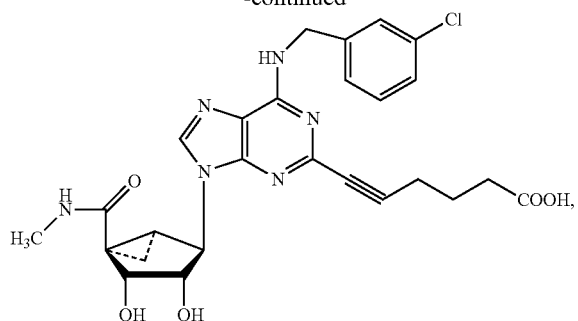
MRS5151
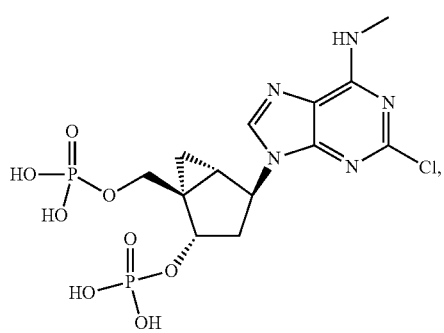
MRS2279
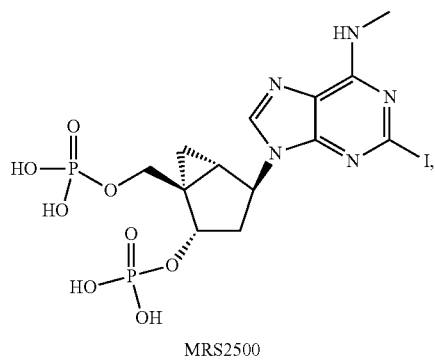
MRS2500
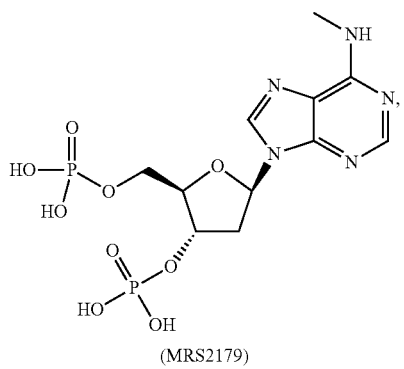
(MRS2179)
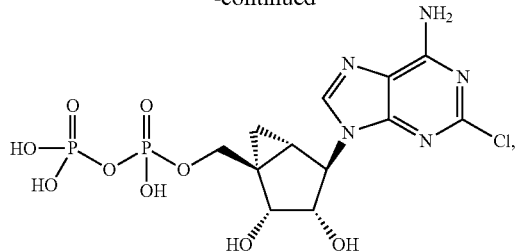
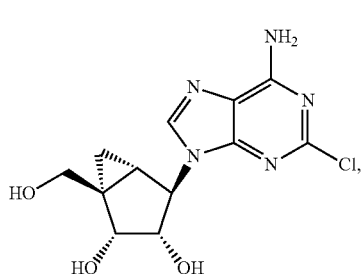
(MRS1873 or AST-008)
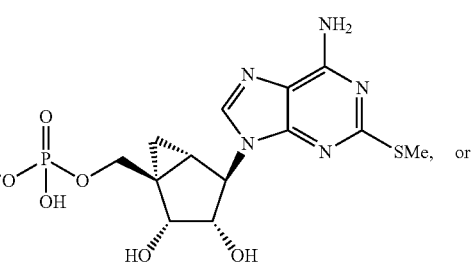
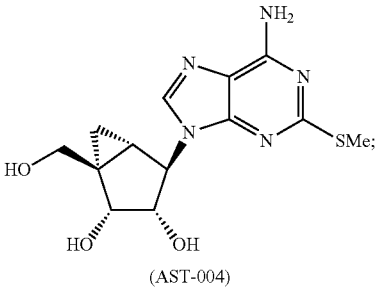
(AST-004)
or a pharmaceutically acceptable salt thereof. In some embodiments, the compound is selected from a (N)-methanocarba nucleoside such as those disclosed above; or a pharmaceutically acceptable salt thereof.
In some embodiments, the compound is selected from
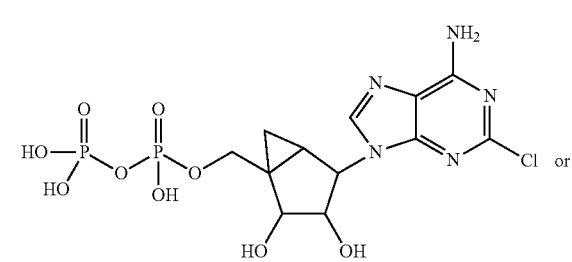

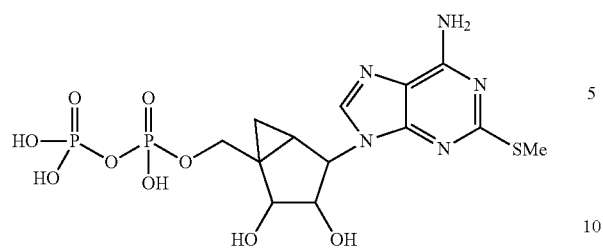
or a pharmaceutically acceptable salt thereof. In some embodiments, the compound is selected from the group consisting of:
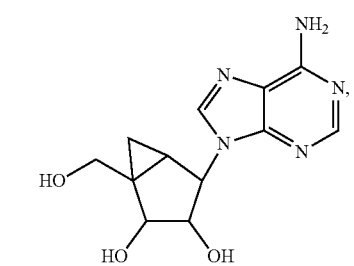
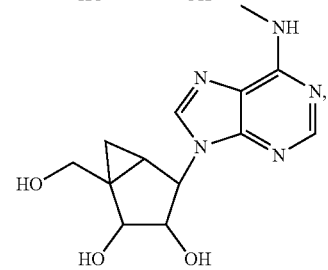
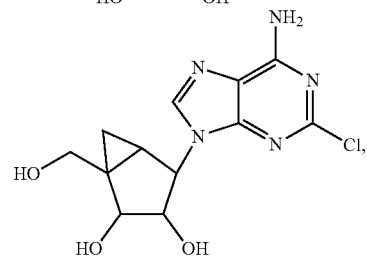
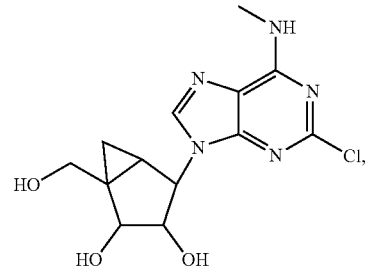
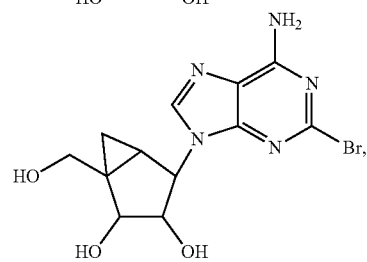
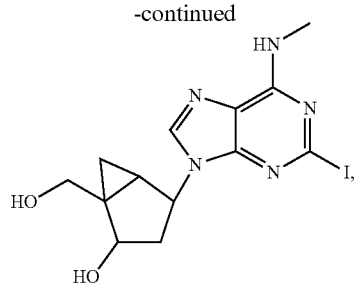
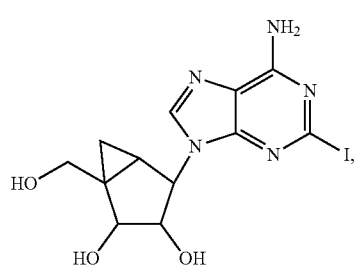
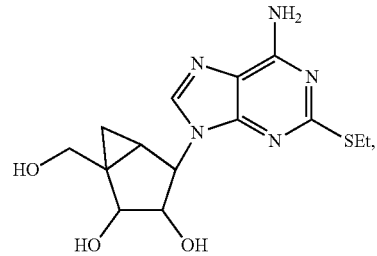
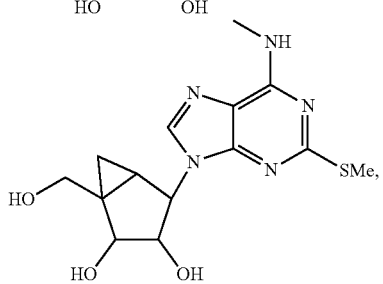
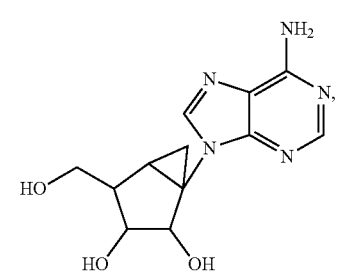
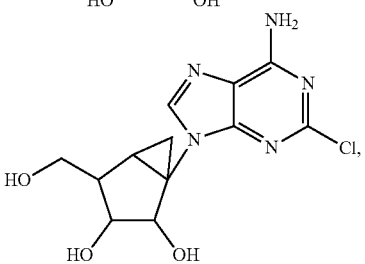

-continued

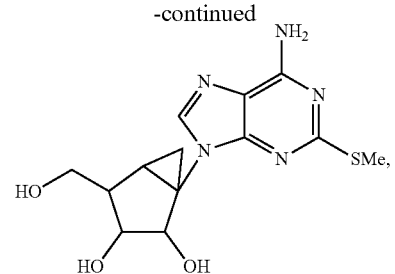

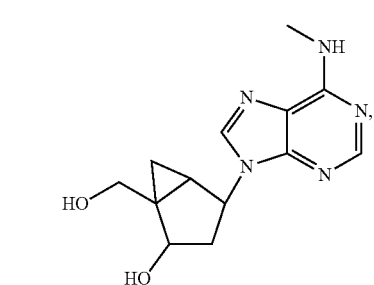

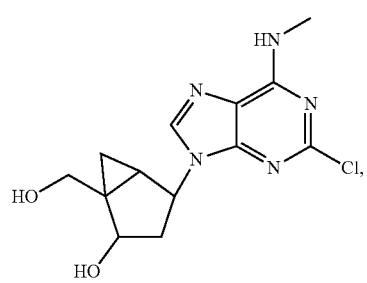

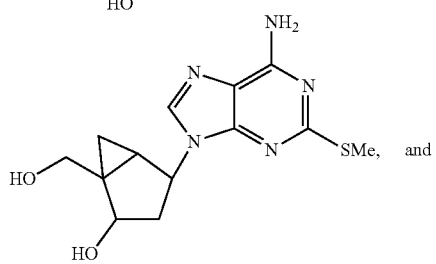

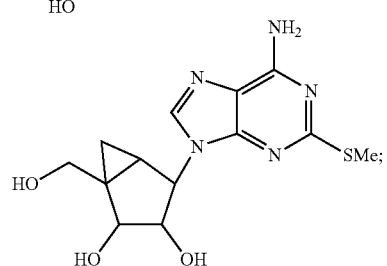

wherein each compound may be in the North or South conformation or the methanocarba sugar may be replaced with a D-ribosugar; or a pharmaceutically acceptable salt thereof, or a mono-, di-, or triphosphate thereof or pharmaceutically acceptable salt of the mono-, di-, or triphosphate. In some embodiments, the methanocarba sugar is a D-(N)-methanocarba sugar. In some embodiments, the methanocarba sugar is a D-(S)-methanocarba sugar.

In some embodiments, the compound is selected from:

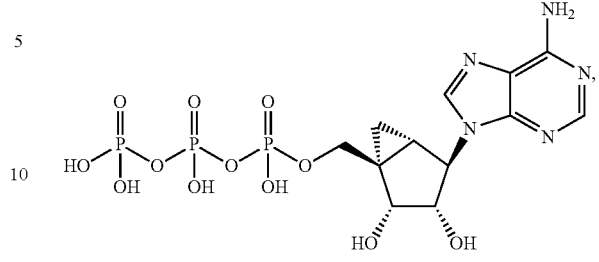
(MRS2340)

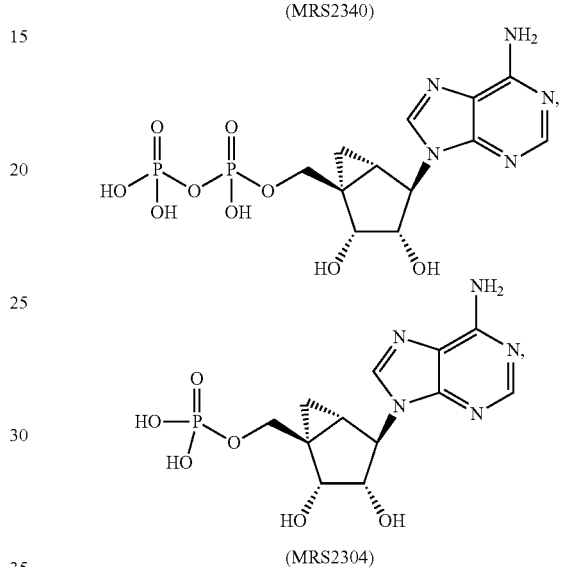
(MRS2304)

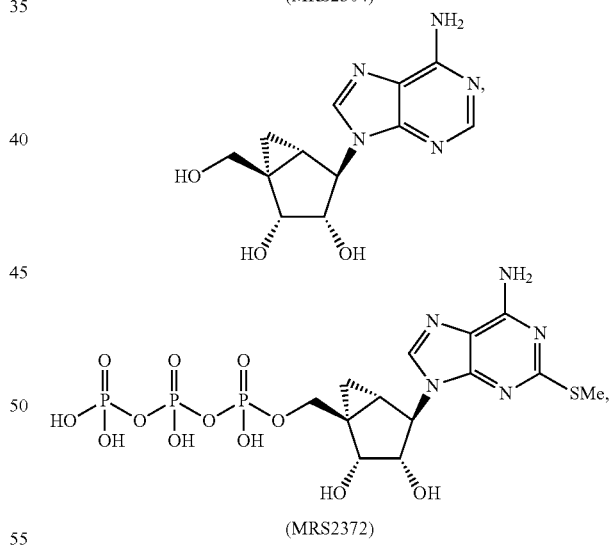
(MRS2372)

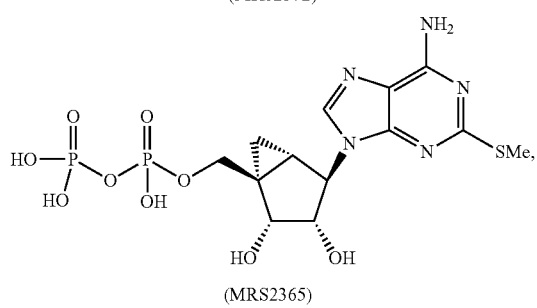
(MRS2365)

-continued
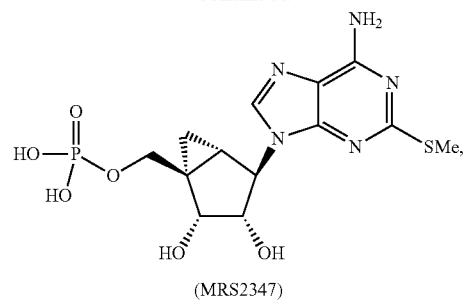
(MRS2347)
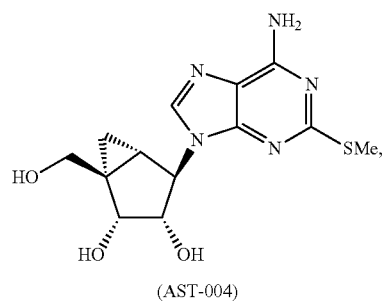
(AST-004)
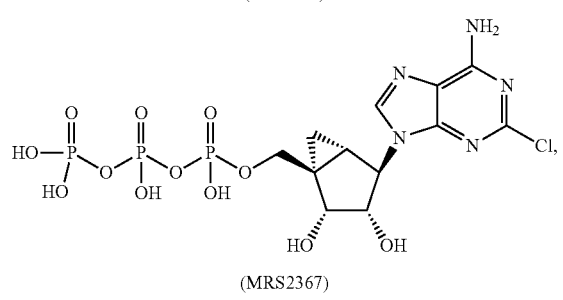
(MRS2367)
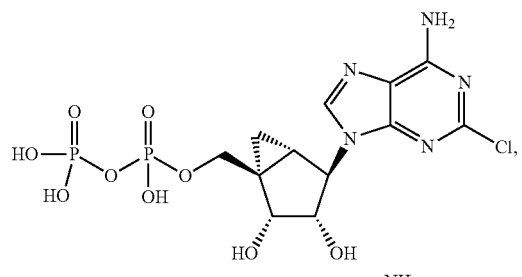
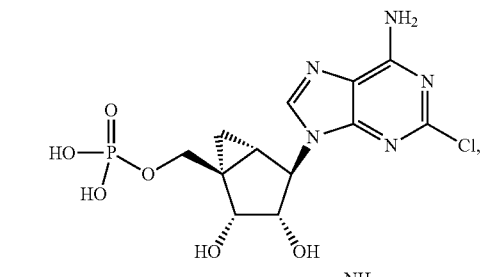
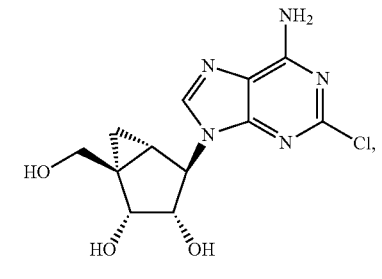
(MRS1873 or AST-008)
-continued
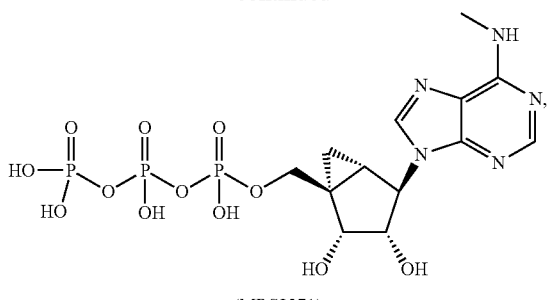
(MRS2371)
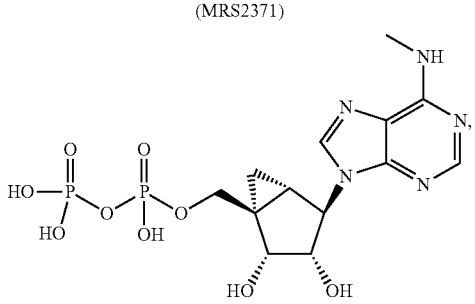
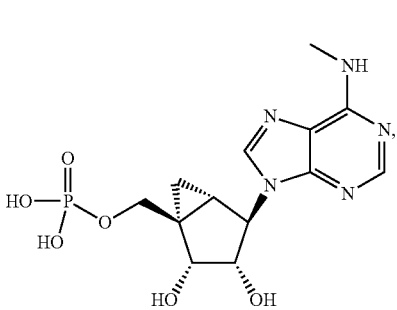
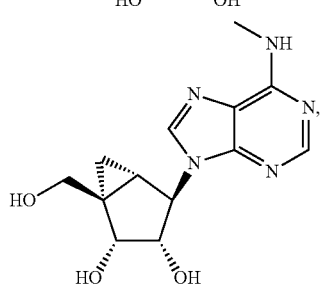
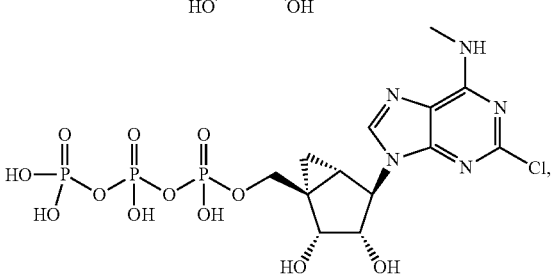
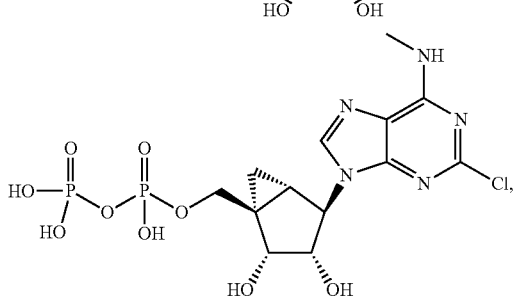

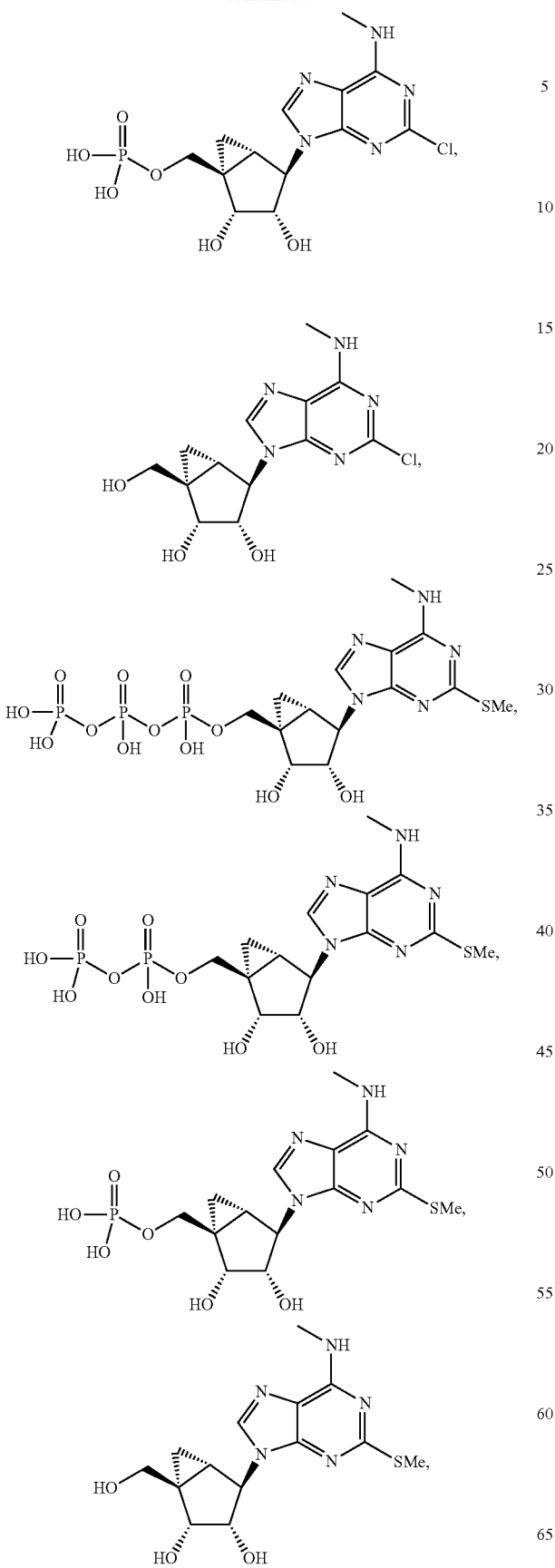
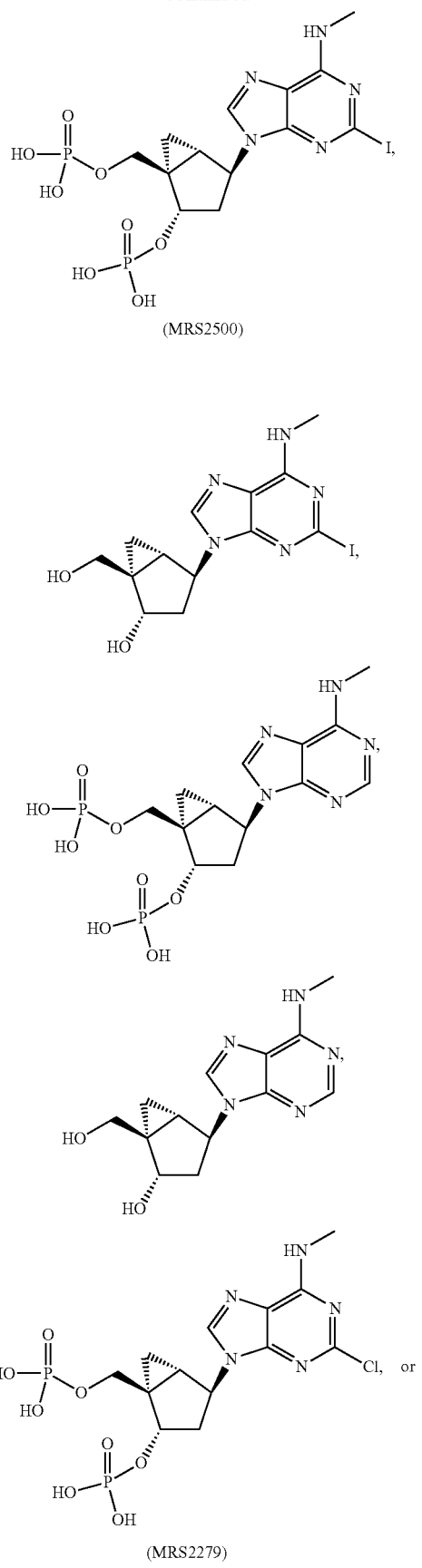

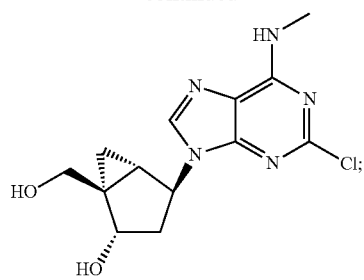

or a pharmaceutically acceptable salt thereof. In some embodiments, the compound is selected from a (N)-methanocarba nucleoside such as those disclosed above; or a pharmaceutically acceptable salt thereof.

In some embodiments, the compound is selected from

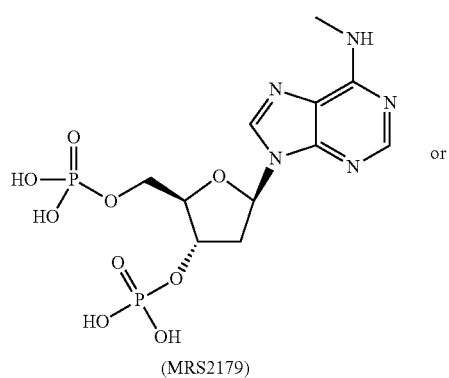

(MRS2179)

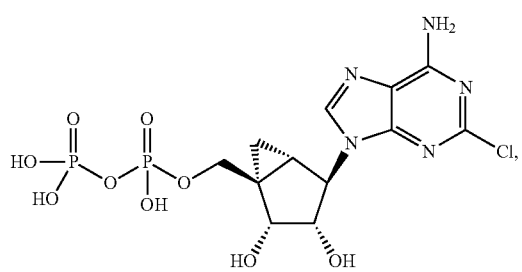

or a pharmaceutically acceptable salt thereof.

In some embodiments, the compound is selected from

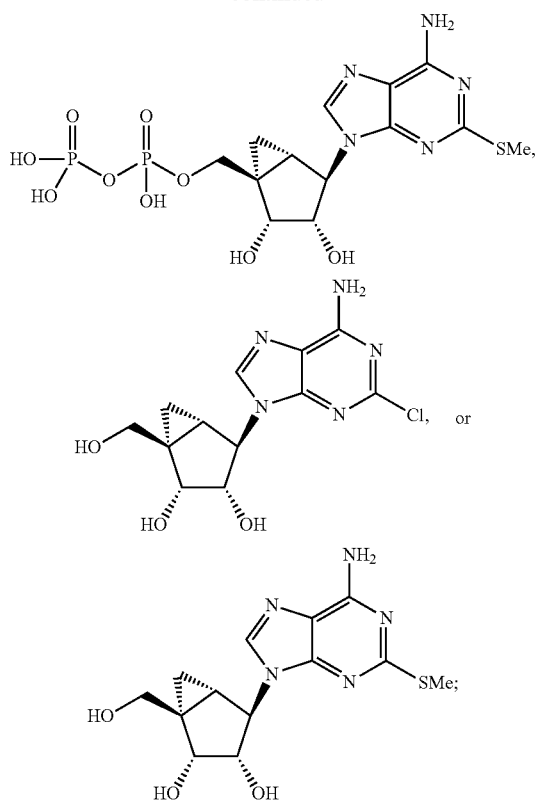

or a pharmaceutically acceptable salt thereof.

In some embodiments, the compound is

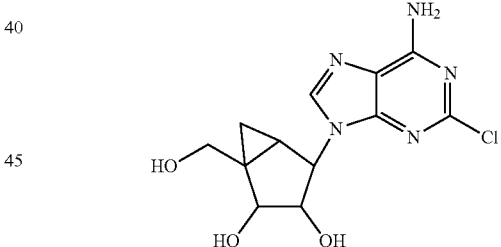

or a pharmaceutically acceptable salt thereof. In some embodiments, the compound is

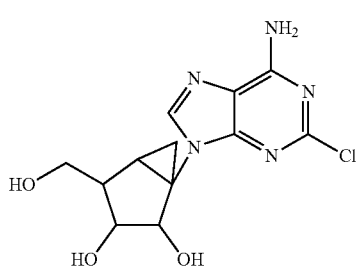 [SMILES: Nc1nc(Cl)nc2c1ncn2C12CC1C(CO)C(O)C2O]

or a pharmaceutically acceptable salt thereof. In some embodiments, the compound is

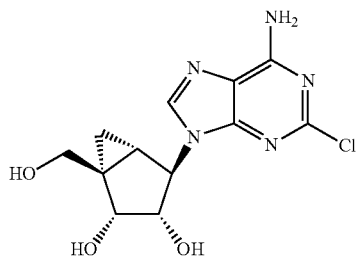 [SMILES: Nc1nc(Cl)nc2c1ncn2[C@H]1[C@H](O)[C@H](O)[C@]2(CO)C[C@H]12]

or a pharmaceutically acceptable salt thereof.

In some embodiments, the compound is

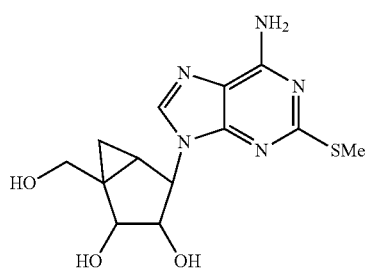 [SMILES: CSc1nc(N)c2ncn(C3C(O)C(O)C4(CO)CC34)c2n1]

or a pharmaceutically acceptable salt thereof. In some embodiments, the compound is

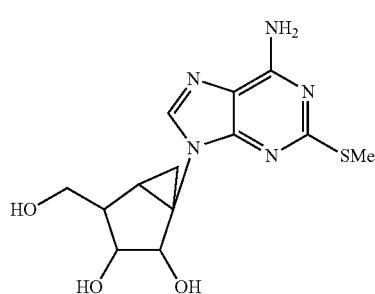 [SMILES: CSc1nc(N)c2ncn(C34CC3C(CO)C(O)C4O)c2n1]

or a pharmaceutically acceptable salt thereof. In some embodiments, the compound is

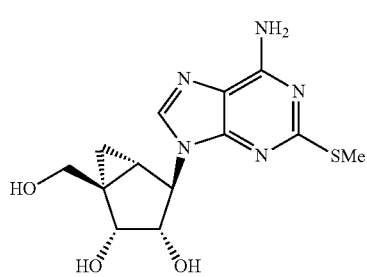 [SMILES: CSc1nc(N)c2ncn([C@H]3[C@H](O)[C@H](O)[C@]4(CO)C[C@H]34)c2n1]

or a pharmaceutically acceptable salt thereof. In some embodiments, the compound is

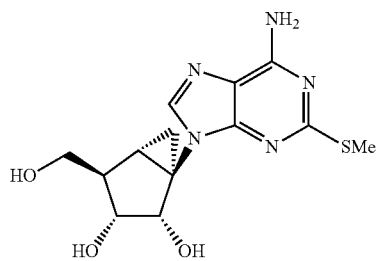 [SMILES: CSc1nc(N)c2ncn([C@]34C[C@H]3[C@H](CO)[C@@H](O)[C@H]4O)c2n1]

or a pharmaceutically acceptable salt thereof. In some embodiments, the compound is

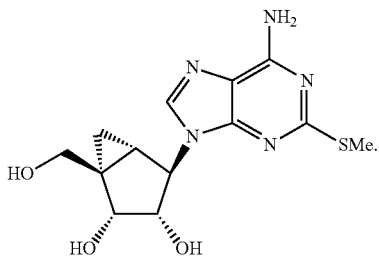 [SMILES: CSc1nc(N)c2ncn([C@H]3[C@H](O)[C@H](O)[C@]4(CO)C[C@H]34)c2n1]

In one aspect, the present invention provides a pharmaceutical composition comprising a disclosed compound or a pharmaceutically acceptable salt thereof and a pharmaceutically acceptable excipient. In some embodiments, the compound is

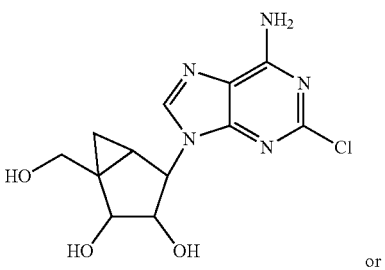

or

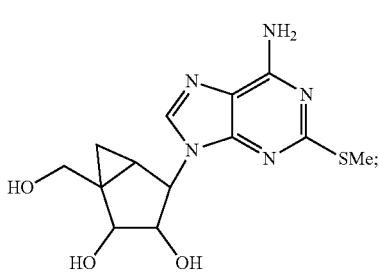

or a pharmaceutically acceptable salt thereof. In some embodiments, the compound is

Figure 9:
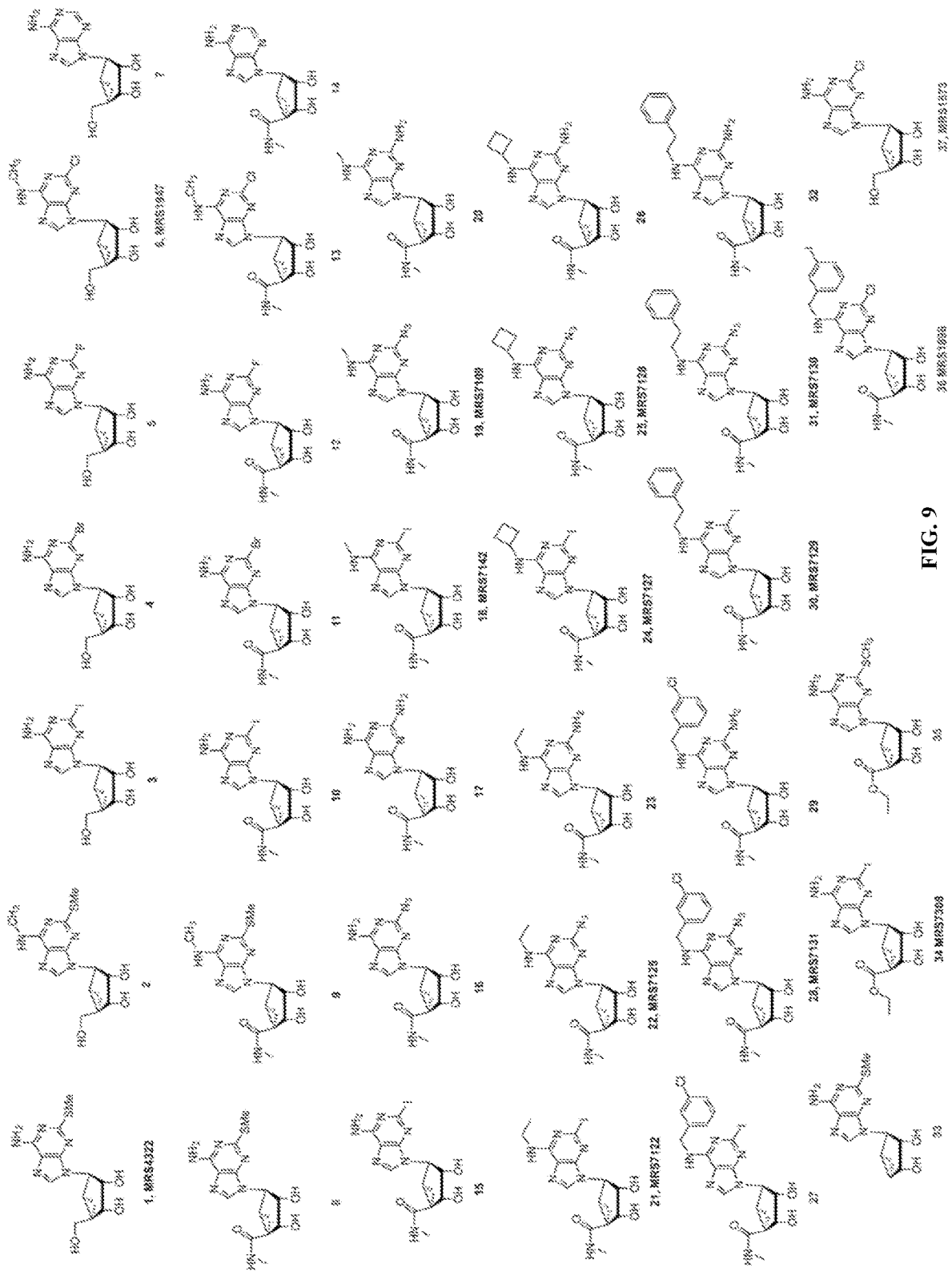
FIG. 9: Structures of certain compounds useful in the present invention. Such compounds may be used in any of the methods described herein.

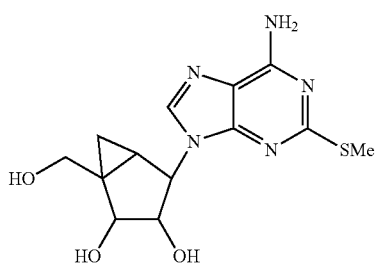 [SMILES: CSc1nc(N)c2ncn(C3C(O)C(O)C4(CO)CC34)c2n1]
or a pharmaceutically acceptable salt thereof. In some embodiments the compound is
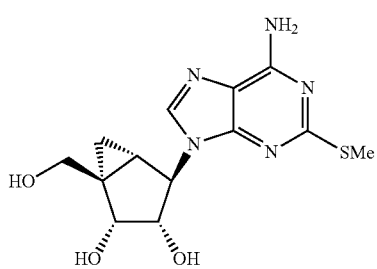 [SMILES: CSc1nc(N)c2ncn([C@H]3[C@H](O)[C@H](O)[C@]4(CO)C[C@H]34)c2n1]
or a pharmaceutically acceptable salt thereof. In some embodiments, the compound is
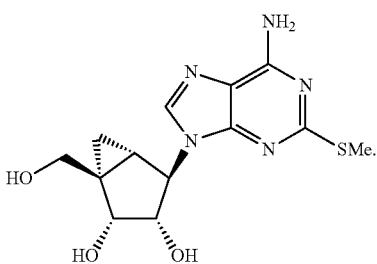 [SMILES: CSc1nc(N)c2ncn([C@H]3[C@H](O)[C@H](O)[C@]4(CO)C[C@H]34)c2n1]
In some embodiments, the compound is selected from those in FIG. 9, or a pharmaceutically acceptable salt thereof. In some embodiments, the compound is selected from
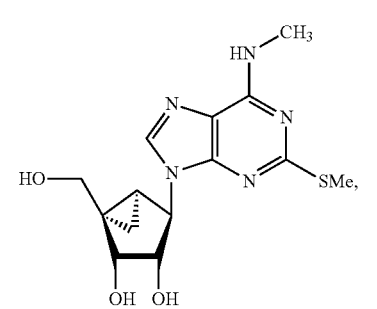
2
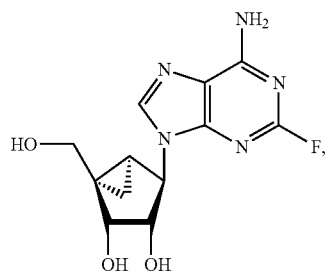
5
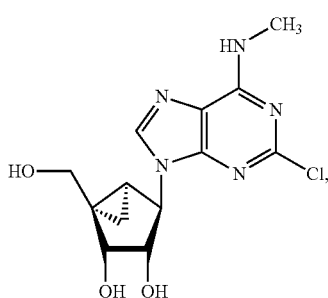
MRS1947
6
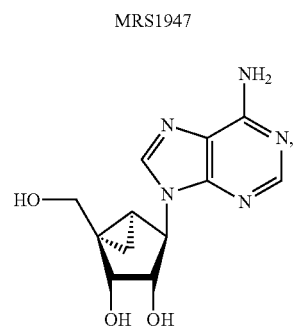
7
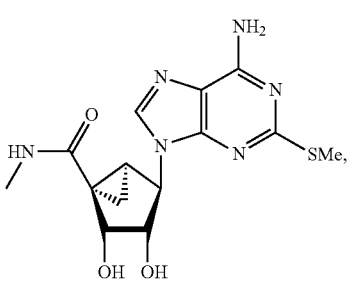
8
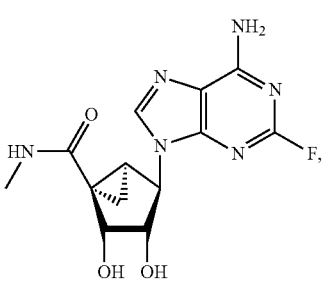
12

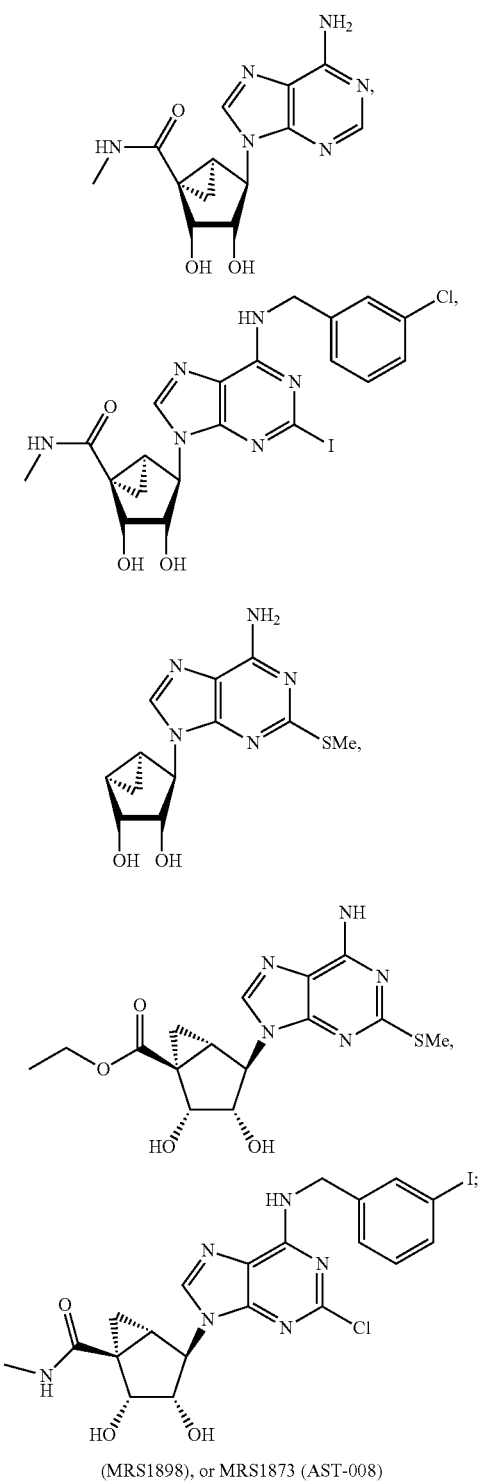

(MRS1898), or MRS1873 (AST-008)

or a pharmaceutically acceptable salt thereof.

In one aspect, the present invention provides a method of treating or promoting recovery from an addiction, addictive behavior, behavioral addiction, brain reward system disorder, compulsive disorder, or related condition, comprising administering to a patient in need thereof an effective amount of a compound selected from:

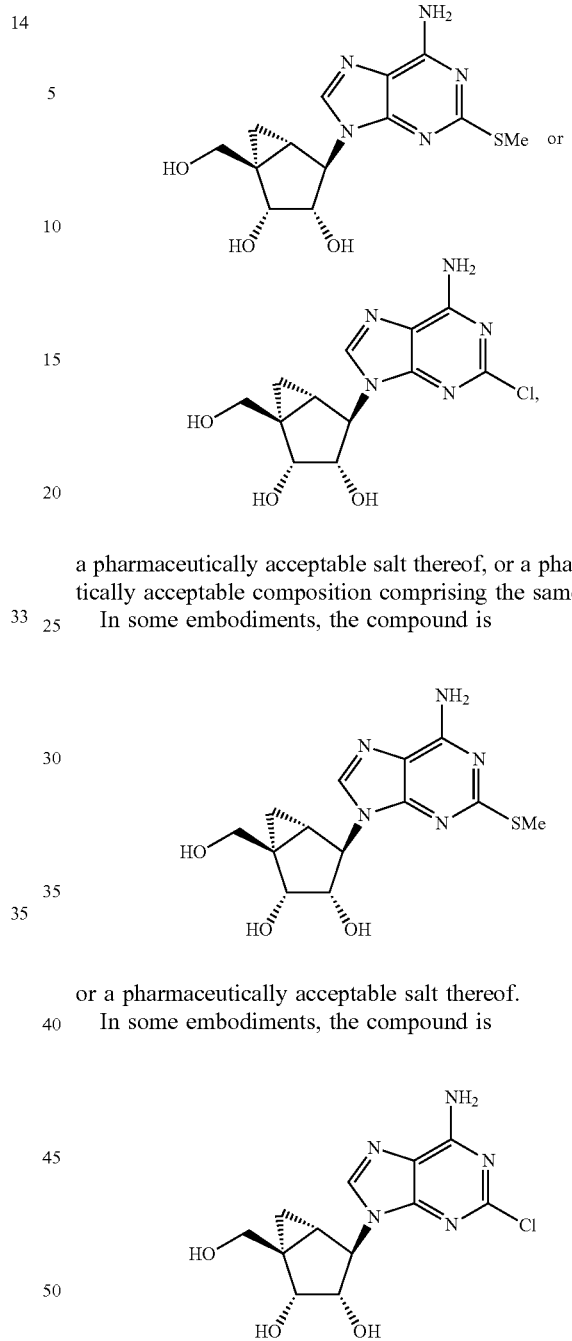

a pharmaceutically acceptable salt thereof, or a pharmaceutically acceptable composition comprising the same.

In some embodiments, the compound is or a pharmaceutically acceptable salt thereof.

In some embodiments, the compound is or a pharmaceutically acceptable salt thereof.

In some embodiments, the compound is a biased partial agonist at a human $A_3$ adenosine receptor ($A_3R$).

In some embodiments, the $A_3R$ is partially agonized in a manner biased toward neuroprotective functions of the $A_3R$ receptor.

In some embodiments, the compound is administered orally, intravenously, or parenterally.

In some embodiments, the compound or pharmaceutically acceptable salt thereof has an unbound fraction in plasma of at least 0.7 or at least 0.08 unbound fraction in brain, or both.

In some embodiments, the compound or pharmaceutically acceptable salt thereof has an unbound fraction in plasma of at least 0.7 or at least 0.08 unbound fraction in brain, or both.

In some embodiments, the $A_3R$ is agonized in a biased manner toward neuroprotective functions of the $A_3R$ receptor via preferential activation of intracellular calcium mobilization with less, or no, activation of other $A_3R$-mediated pathways, or via preferential activation of Gq11-mediated intracellular calcium mobilization, Gi-mediated modulation of cAMP production, or Gi-mediated phosphorylation of ERK1/2 and Akt.

In some embodiments, the compound is administered orally.

The amount of a disclosed compound (i.e., active agent) that should be present in a composition for use a disclosed method or a disclosed pharmaceutical composition will generally be a therapeutically effective amount. A "therapeutically effective amount" or dose (or "effective amount") refers to that amount of the active agent sufficient to result in a desired therapeutic result. Toxicity and therapeutic efficacy of compositions of active agents can be determined by procedures known in the art in cell cultures or experimental animals, e.g., for determining the $LD_{50}$ (the dose lethal to 50% of the test group) and the $ED_{50}$ (the dose therapeutically effective in 50% of the test group). The dose ratio between toxic and therapeutic effects is the therapeutic index and it can be expressed as the ratio $LD_{50}/ED_{50}$. Compositions which exhibit large therapeutic indices are advantageous. Data obtained from cell culture assays and animal studies can be used in formulating a range of dosages for use in humans. In some embodiments, the dosage of such compositions lies within a range of circulating concentrations that include the $ED_{50}$ with little or no toxicity. The dosage may vary within this range depending upon the dosage form employed and the route of administration utilized.

Disclosed methods of treatment may encompass administration of a disclosed compound as needed to obtain the desired therapeutic effect. The composition can be administered as long as necessary to maintain the desired therapeutic effect, such as a preventative effect, e.g. to prevent relapses into addiction or risky behaviors. In some embodiments, the compound is administered between about one and 12 months. In some embodiments, the compound is administered between one and six months. In some embodiments, the compound is administered between one and three months.

In one aspect of the invention, a disclosed compound is administered in an amount between about 5 mg/day and 10 g/day. In some embodiments, each dose of the compound is in an amount between about 5 mg/dose and 10 g/dose. For example, satisfactory results are obtained by oral administration of a disclosed compound of the invention at dosages between about 0.05 and 10 mg/kg/day, between about 0.1 and 7.5 mg/kg/day, between about 0.1 and 2 mg/kg/day, or 0.5 mg/kg/day administered once or, in divided doses, 2 to 4 times per day. For parenteral administration, for example by i.v. drip or infusion, dosages between about 0.01 and 5 mg/kg/day, between about 0.05 and 1.0 mg/kg/day and between about 0.1 and 1.0 mg/kg/day can be used. Suitable daily dosages for patients are thus between about 2.5 and 500 mg p.o., between about 5 and 250 mg p.o., between about 5 and 100 mg p.o., or between about 0.5 and 250 mg i.v., between about 2.5 and 125 mg i.v. and between about 2.5 and 50 mg i.v.

4. Uses, Formulation and Administration

Pharmaceutically Acceptable Compositions

According to another embodiment, the invention provides a composition comprising a disclosed compound and a pharmaceutically acceptable carrier, adjuvant, or vehicle. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

In other embodiments, pharmaceutically acceptable compositions of this invention are formulated for intravenous (IV) administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the treatment of various diseases and conditions, such as brain injuries and neurodegenerative conditions, and the various methods disclosed herein.

The activity of a compound utilized in the present invention may be assayed in vitro, in vivo or in a cell line. In vitro assays include assays that determine modulation or binding to a protein. Detailed conditions for assaying a compound are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a disclosed disease or condition, or associated condition or symptom. The exact amount required will vary from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, in some embodiments a mammal, or in certain other embodiments a human.

Pharmaceutically acceptable compositions of this invention can be administered to humans and other animals orally, sublingually, rectally, parenterally, intracisternally, intravaginally, intraperitoneally, topically (as by powders, ointments, or drops), intraocularly (such as eye drops), bucally, as an oral or nasal spray, or the like, depending on the severity of the disease or condition being treated. In certain embodiments, the compounds of the invention may be administered orally or parenterally at dosage levels of about 0.01 mg/kg to about 50 mg/kg or from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

As depicted in the Examples below, in certain exemplary embodiments, compounds are prepared and used according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The contents of each document cited in the specification are herein incorporated by reference in their entireties.

EXEMPLIFICATION

Example 1: Effect of AST-004 on Cocaine Self-Administering Mice

This study is believed to be the first to examine the connection between energy metabolism and drug addiction.

Published work indicates cocaine self-administering mice exhibit significantly higher glutamate levels in the VTA. This appears to be due, at least in part, to loss of glutamate uptake into astrocytes. Our data focuses on the impact of reduced availability of glutamate on astrocyte function and on how this loss of function affects neuronal activity and drug-seeking behavior.

Our data show that mitochondrial metabolism in astrocytes can be increased by treatment with G-protein coupled agonists that stimulate $IP_3$ Ca2+ signaling (Reference 1 below).

We found that AST-004 is an $A_3R$ agonist that stimulates intracellular Ca2+ (FIG. 1). The low level stimulation of Ca2+ release persisted throughout the recording (FIG. 1A,B). It was not blocked by pertussis toxin treatment, consistent with Gq-coupling. The integrated $Ca^{2+}$ response was also dose-dependent (FIG. 1C) and present in astrocytes cultured from mouse, rat, pig and human brain tissue.

Figure 2:
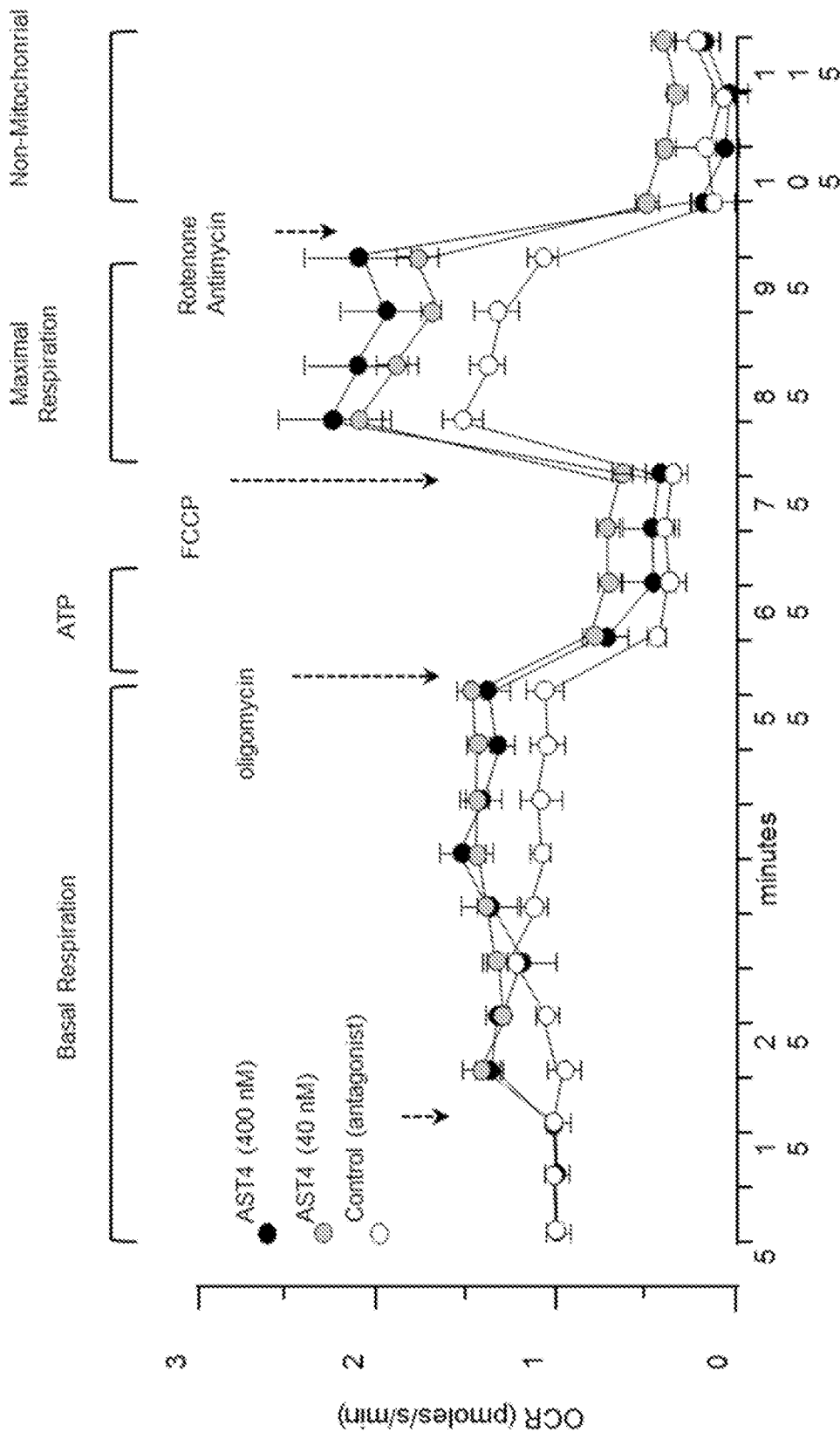
FIG. 2: Oxygen Consumption Rate (OCR) is increased by purinergic agonist AST-004. Cultured astrocytes were plated on a standard Seahorse dish (24 well). After establishing basal OCR, purinergic agonist AST-004 or control (antagonist) was added at first arrow. Basal respiration was significantly increased in AST-004-treated wells. Oligomycin was added at second arrow, revealing the amount of OCR that could be attributed to ATP production. As revealed with the addition of uncoupler FCCP ($3^{rd}$ arrow), maximal respiration was significantly higher in AST-004 treated astrocytes. The final addition of mitochondrial inhibitors uncovered non-mitochondrial OCR sources.

We previously reported that any agonist stimulating $IP_3$-mediated $Ca^{2+}$ increases in astrocytes increased ATP production in astrocytes (1). To confirm AST-004-induced $Ca^{2+}$ release also increased metabolism, we cultured astrocytes (C8-D1A, available from ATCC) and measured oxygen consumption rates (OCR) using a standard Seahorse chamber (24 wells). As shown in FIG. 2, basal respiration was initially comparable in all three experiments, but increased when AST-004 was added to the bath (15 minutes, first arrow). Minimal change was observed under control injections. Oligomycin injection revealed ATP production was significantly greater for astrocytes treated with AST-004 (400 nM). Uncoupling of the cells by addition of FCCP (p-trifluoromethoxy carbonyl cyanide phenyl hydrazone) revealed that maximal respiration was also significantly higher for the astrocytes treated with AST-004. Addition of rotenone and antimycin uncovered non-mitochondrial sources of oxygen consumption, which was subtracted off from all measurements prior to calculations.

Figure 3:
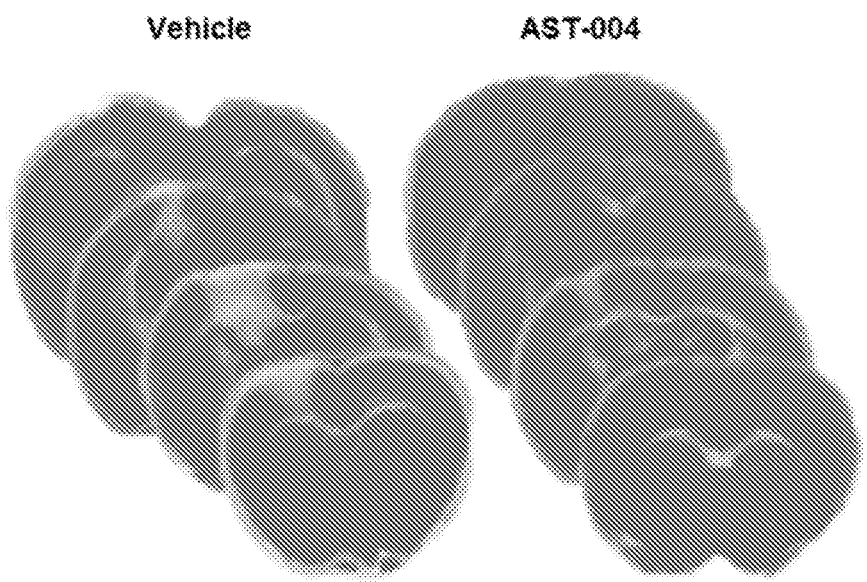
FIG. 3: Photothrombosis-induced stroke infarctions that are reduced by AST-004 and are blocked by $A_3R$ Antagonist (MRS1523). A) Sequential coronal sections of brains stroked with photothrombosis in vehicle (saline injected) and in treated mice, AST-004 (0.2 mg/kg). Mice were sacrificed at 24 hours post-stroke, their brains removed, sectioned and stained with TTC. B) Average TTC-stained stroke volumes. C) Stroke volumes in mice pretreated with the $A_3R$ antagonist MRS1523. Data were pooled from 2 experiments (mean+/−SEM).
Figure 3:
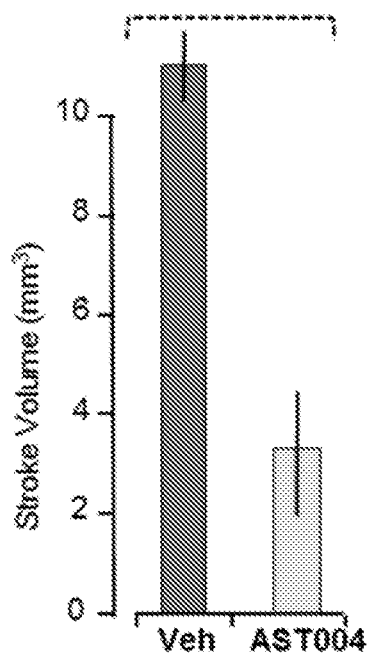
Figure 3:
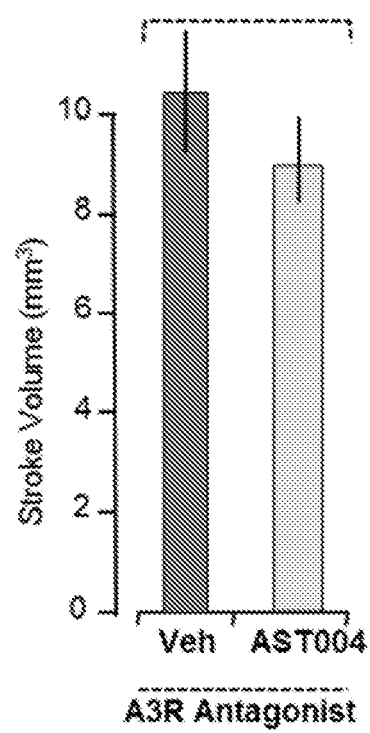
Figure 4:
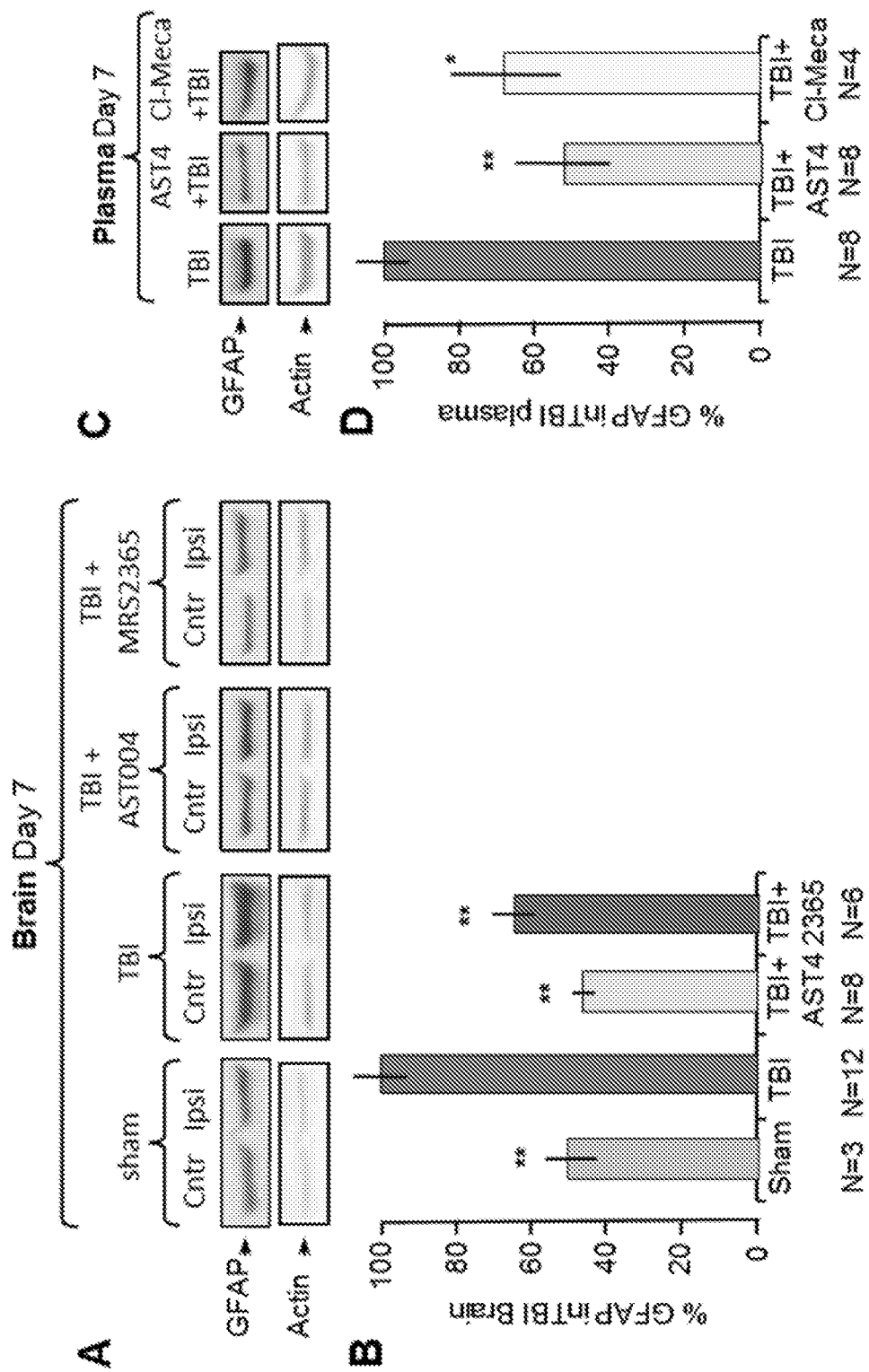
FIG. 4: TBI induced increases in GFAP expression are reduced by AST-004 (AST-004) and MRS2365 treatments. Mice underwent sham or TBI (on Ipsilateral side of brain) and received treatments as labeled 30 min post-TBI. Plasma was obtained from mice at 7 days post-injury, then sacrificed to obtain brain homogenates from the ipsilateral and contralateral hemispheres (middle third). Western blot analysis were normalized to actin. (A and C) Representative blots are shown for Ipsilateral brain homogenates and the plasma at day 7. (B and D) Data were pooled from 3 distinct experiments (N=number of mice per treatment) and plotted as bar histograms, shown as mean of control+/−SEM. *$p<0.05$ and ** $p<0.01$ from TBI untreated (dark gray bar).

We next tested the predicted neuroprotective efficacy of AST-004 using our well-established photothrombotic induced model of stroke (2, 3). As expected, we found that AST-004 treatment significantly reduced stroke infarction volume (FIG. 3A,B), which was blocked by pretreatment with the A3R antagonist MRS1523 (FIG. 3C). AST-004 was also neuroprotective after traumatic brain injury (TBI) (FIG. 4) in mice.

Figure 5:
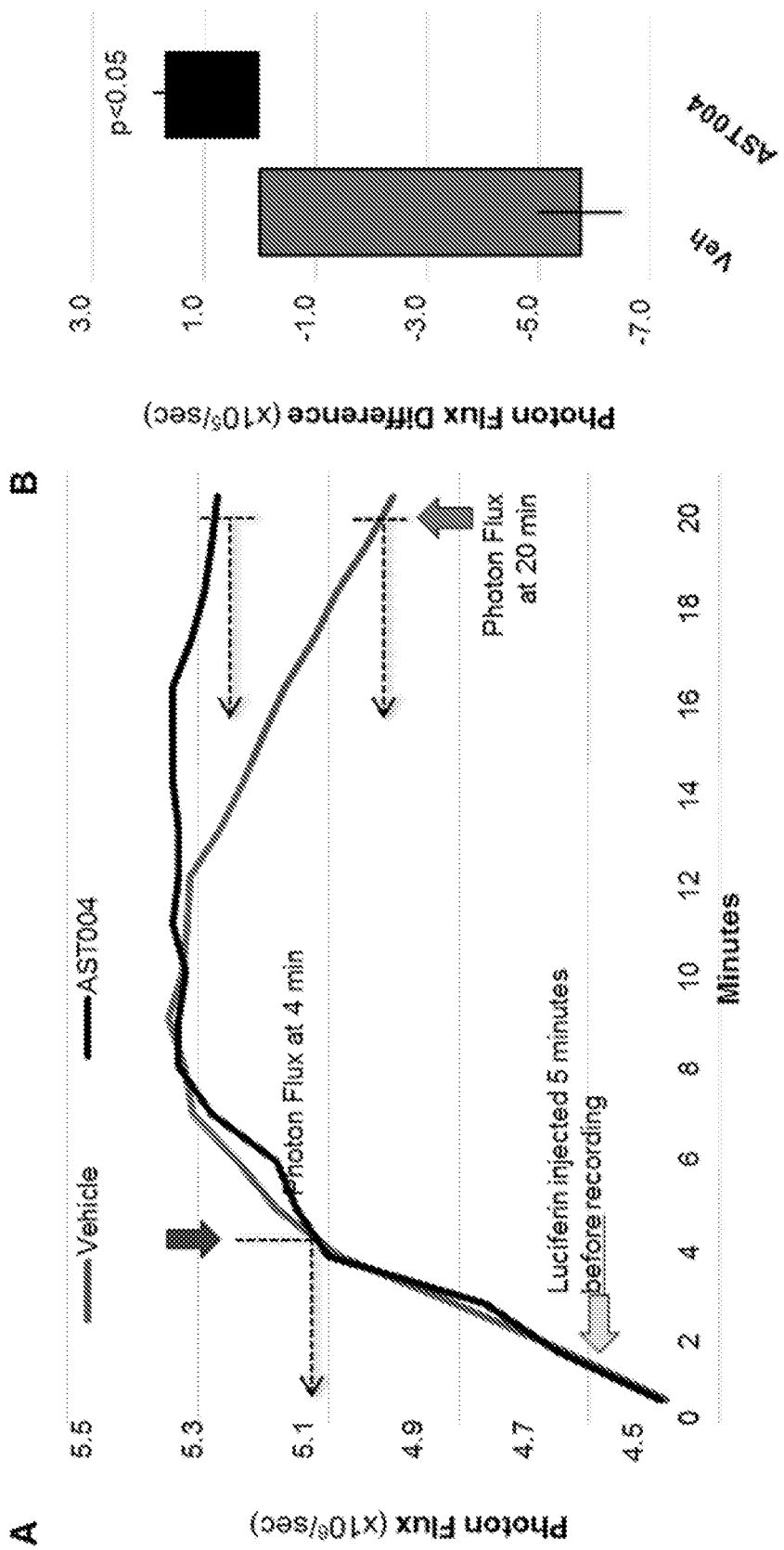
FIG. 5: In Vivo Bioluminescent Imaging indicates AST-004 increases ATP. A) Transgenic mice expressing the Luciferase-reporter gene in astrocytes (GFAP promoter) were subjected to blunt TBI (Closed Cortical Impact). Two to 4 days after the initial trauma, mice were IP injected with a synthetic D-luciferin analogue (Cytluc1, 100 ul). Bioluminescent signals were recorded with an IVIS Spectrum Imager, 5 min after Cycluc1 injection (green arrow). Mice were then IP injected with either vehicle or AST-004 at 4 minutes (blue arrow), the photon flux immediately measured and then compared to the photon flux at 20 minutes (red arrow). B) Histogram plot showing mice injected with AST-004 exhibited higher photon flux levels compared to vehicle, consistent with higher ATP-production in astrocytes.

In Vivo Bioluminescent Imaging indicated that $A_3R$ agonist AST-004 increases ATP in astrocytes (FIG. 5). Transgenic mice expressing the Luciferase-reporter gene in astrocytes (GFAP promoter, Dual-Glo mice, Jackson laboratories) were subjected to blunt TBI (Closed Cortical Impact). Two to 4 days after the initial trauma, mice were IP injected with a synthetic D-luciferin analogue (Cycluc 1) and bioluminescent signals recorded on an IVIS Spectrum Imager (FIG. 5A). Mice injected with AST-004 exhibited significantly higher photon flux levels compared to mice injected with vehicle, consistent with higher ATP-production in astrocytes (FIG. 5B).

Figure 6:
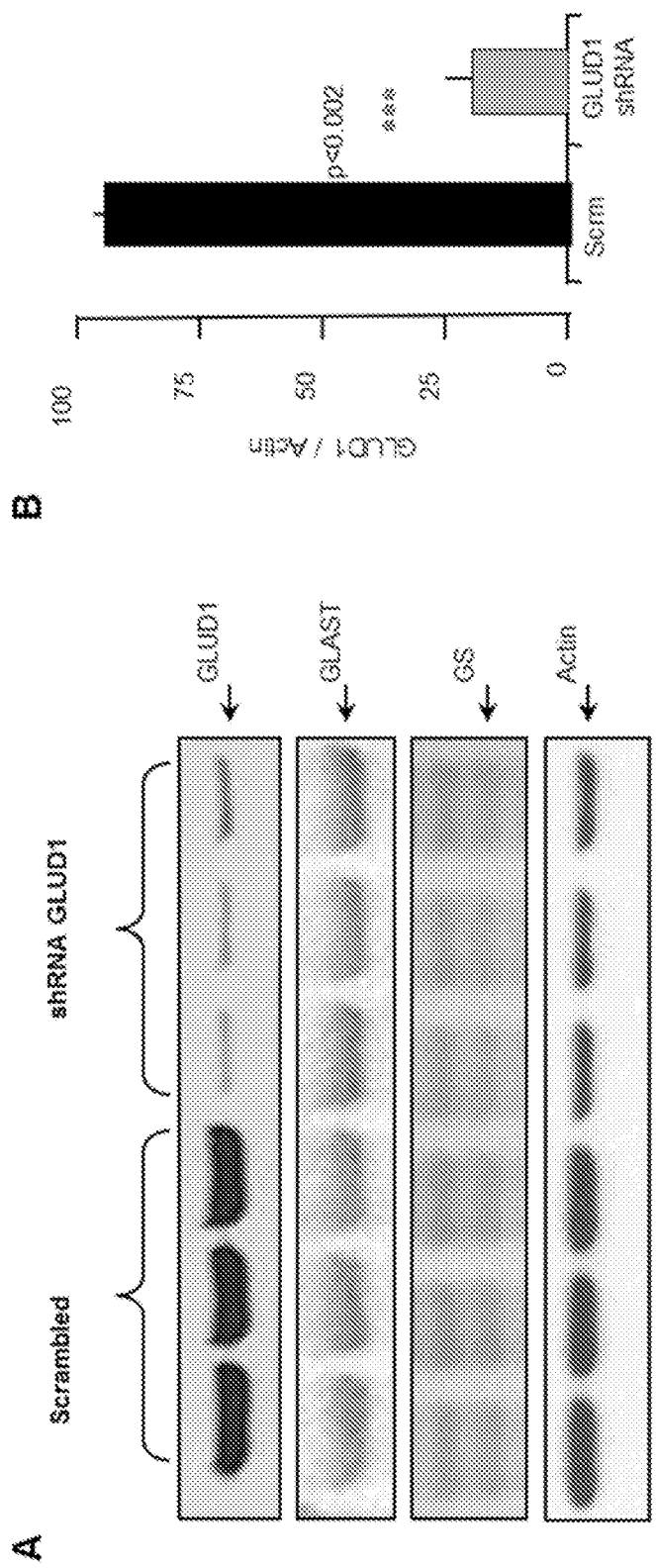
FIG. 6: GLUD1 expression is reduced by 80% in cultured astrocytes treated with shRNA. A) Western blots analysis of cell extracts obtained from astrocyte cell line (C8D1A) that were subjected to control (Scram) or GLUD1 shRNA. GLUD1 levels are significantly reduced. For comparison, westerns blots of GLAST, Glutathione Synthetase (GS) and actin are also presented. B) Histogram plot of expression levels normalized to actin. GLUD1 is reduced by approximately 80% reduced.
Figure 7:
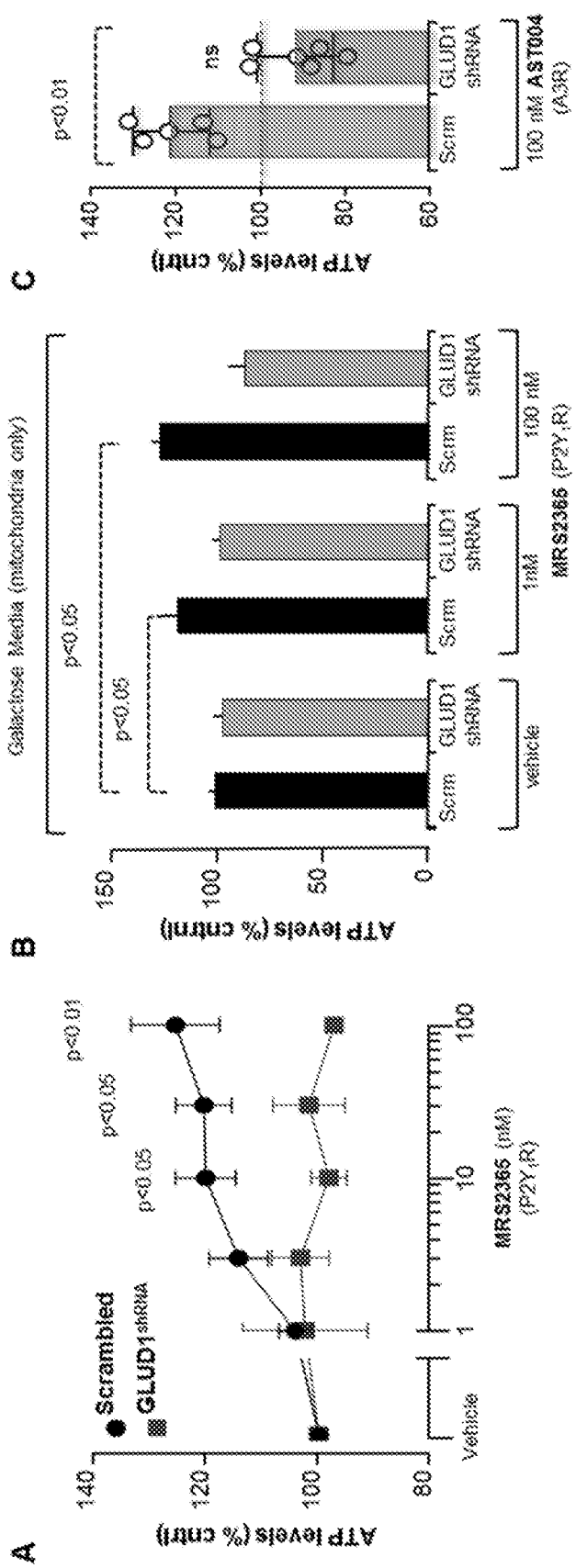
FIG. 7: GLUD1 Knockdown (KD) in astrocytes blocks $P2Y_1R$ and A3R-stimulated increases in ATP. A, B) Cells were treated with $P2Y_1R$ agonist MRS2365 for 20 mins in either normal glucose medium (A) or a glucose-free, galactose (B) supplemented media. Galactose forces cells to use oxidative phosphorylation for energy metabolism. ATP levels are significantly increased following $P2Y_1R$ stimulation at the indicated concentrations of MRS2365, but only in control cells (scrambled shRNA). Those treated with shRNA for GLUD1 were not responsive. C) ATP levels were also increased with A3R agonist AST-004, but not in cells treated with GLUD1 shRNA. Intracellular ATP levels were measured with a luciferin-luciferase kit.

$P2Y_1R$ and $A_3R$ agonists increased mitochondrial ATP production in astrocytes in a manner that was dependent on GLUD1 expression. One possible hypothesis is that glutamate catabolism into α-KG is mediated by GLUD1, which is enhanced by $Ca^{2+}$ dependent stimulation of the ICDH and α-KGDH in the TCA cycle. To test this hypothesis, GLUD1 expression levels were reduced in astrocyte cultures by incubating cells with specific shRNA. Western blot analysis showed reduction in GLUD1 levels by 80% (FIG. 6A,B). When these cells were treated for 20 minutes with MRS2365 ($P2Y_1R$ agonist), ATP levels were significantly increased, but only in control cells (scrambled shRNA). Astrocytes with reduced levels of GLUD1 were not responsive (FIG. 7A). These data are in agreement with earlier work in our laboratory using a different $P2Y_1R$ agonist, 2-MeSADP. We repeated these experiments in the presence of galactose, a carbon source that forces cells to generate ATP though oxidative phosphorylation, since glycolysis of galactose is ATP neutral. We found that astrocytes with reduced GLUD1 levels were similarly non-responsive to $P2Y_1R$ stimulation (FIG. 7B). AST-004 also increased ATP levels in a GLUD1-dependent manner (FIG. 7C).

Figure 8:
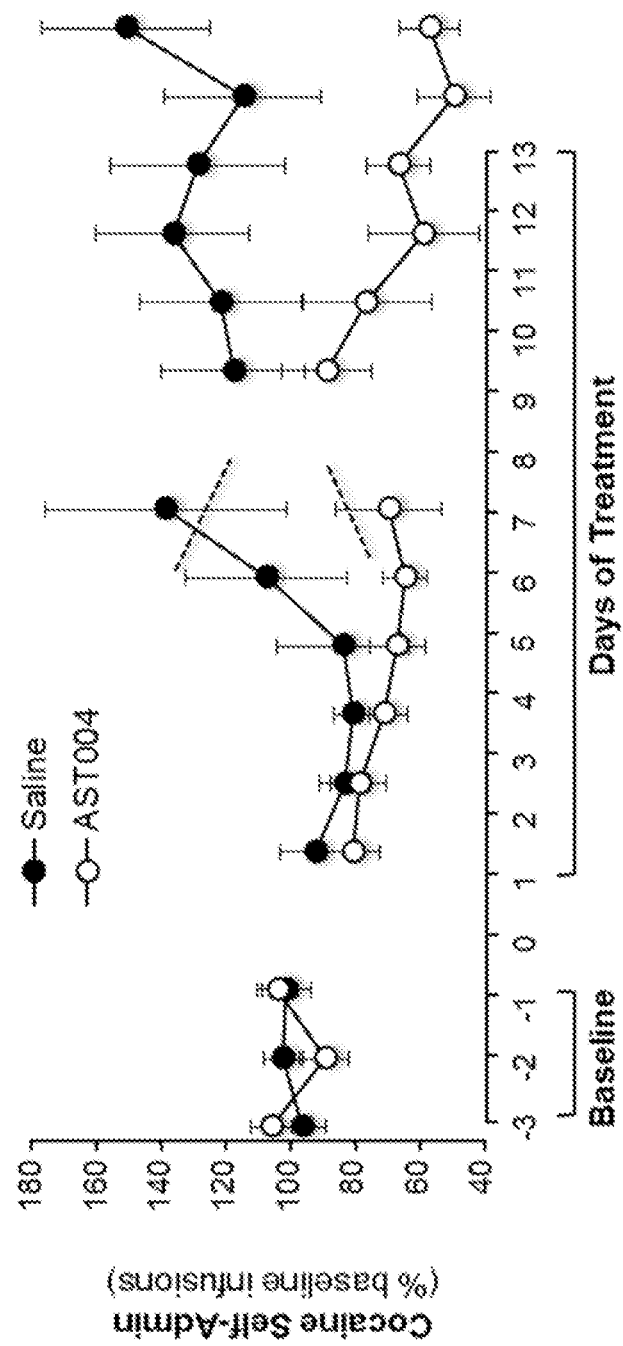
FIG. 8: AST-004 Treatments Significantly Reduce Cocaine Self-Administration in Mice. Data that are normalized to each mouse's individual cocaine intake at baseline. Mice were trained to self-administer cocaine (0.5 mg/kg/ infusion) on a fixed ratio 3 schedule in 2-hr daily sessions. After their intake stabilized (baseline) mice were implanted with osmotic minipumps on day 0 either containing saline (filled circles) or the drug AST-004 (open circles), n=5 mice in each group. Mice were given a day off (day 7), then returned to self-administration in daily sessions. Note the number of infusions goes down in the AST-004 treated mice, while saline treated mice increased infusions.

Behavioral experiments showed that the AST-004, significantly reduces cocaine self-administration in mice (FIG. 8). This discovery has the potential to lead to an inherently robust therapeutic strategy, since all ATP-dependent protective processes in astrocytes are enhanced and limitations associated with targeting a single process are avoided. Increased mitochondrial ATP production via stimulation of either $P2Y_1Rs$ or $A_3R$ promises to be an effective, biological therapy for ameliorating altered brain activity in humans during drug addiction and behaviors associated with drug seeking.

Protocols and Methods:

Primary Cell Cultures

Protocol was modified from McCarthy et al., 1980 (4). Briefly, mice were anesthetized with isoflurane then cervically dislocated. Brains were quickly removed and chopped in trypsin, and allowed to incubate at 37° C. for 30 mins. DMEM/F-12 Media with 10% FCS and primocin was added and brains were triturated to homogenization and filtered through 100 uM mesh, and seeded into culture flasks. The next day, homogenates were transferred to a new flask, and previous flasks had new media added. Cells were grown for 3-4 weeks, with DMEM/F-12 media changes every 3-4 days until cells were 70% confluent.

For Ventral tegmental area (VTA) astrocytes, VTA brain regions were extracted, pooled and astrocytes cultured for at least 2 weeks prior to conducting experiments.

shRNA Knockdown

Cells were transduced with shRNA lentivirus constructs obtained from Santa Cruz (glud1 #145446-V, for Scrambled #108080). Cells were then seeded at single cell/well densities in a 96-well dish and selected for with puromycin. Clones were grown and tested for knockdown by western blot.

Western Blot on Cultured Cells

Cultured cells were washed two times with phosphate-buffered Saline (PBS), and RIPA buffer with PIs (Roche) was added. Cells were scraped using a cell lifter and placed in a 1.7 ml Eppendorf tube. Cells were briefly sonicated and spun on a prechilled tabletop centrifuge for 20 minutes (min) at max speed. To determine protein concentrations, BCA assays were used (Thermo Fisher). Protein was loaded on a 10% SDS-polyacrylamide gel and transferred to nitrocellulose. Blots were blocked in either 5% milk/TBST or 3% BSA/TBST. Blots were probed for GDH (Proteintech, 1:1000), GFAP (Abcam, 1:500), GLAST (1:500), Actin (Sigma, 1:1000), and Glutamine synthetase (1:250). Densitometry was determined using ImageJ software, and statistics were analyzed using GraphPad Prism software.

Determination of ATP Levels

Astrocytes were plated at a density of 3000-5000 cells/well in a white, opaque-bottom 96-well dish (Corning). If cells were tested in galactose medium, they were seeded in galactose medium, and left for a minimum of 16 hours before subjected to treatment. Galactose medium was made with glucose-, pyruvate-, phenol-, and glutamine-free DMEM (Gibco) which was then supplemented with 0.9 mg/ml galactose (Sigma), pyruvate (Quality biological, Inc), and 10% dialyzed FBS (Gibco). Treatments were performed for 20 min unless otherwise stated and concentrations of drugs described elsewhere. Drugs used: MRS2365, MRS2500, AST-004, 3-Propyl-6-ethyl-5-[(ethylthio)carbonyl]-2 phenyl-4-propyl-3-pyridine carboxylate (MRS1523) (Tocris Bioscience), sodium dichloroacetate (DCA) (Sigma Aldrich), Oligomycin (Sigma Aldrich), 1-(2-(2-tert-Butylphenoxy)pyridin-3-yl)-3-(4-(trifluoromethoxy)phenyl)urea (BPTU) (Millipore), and Ruthenium 360 (Cal Biochem). Next, media was removed from cells, and 100 μl fresh media immediately added. Then, 95 μl of mixed luminescence substrate from the ATPlite 1-Step kit were added (Perkin-Elmer). Plates were wrapped in aluminum foil and shaken for 3 min on a plate rotator before reading on a luminometer. Readings were normalized to protein as determined by Coomassie Plus Bradford assay (Thermo Fisher). All statistics were analyzed using GraphPad Prism software.

$Ca^{2+}$ Measurements $Ca^{2+}$ activity was imaged as previously described (5). In brief, astrocytes were seeded on glass cover slips 3 and 4 nights before each experiment. Culture dishes were incubated with a fluorescent $Ca^{2+}$ sensitive dye (10 μM, Cal520, cell permeant, Abcam) 30 min prior to the experiment. Images were acquired with a confocal laser-scanning microscope at the rate of 1.5 images/s. Data were obtained in recording buffer (120 mM NaCl, 4.5 mM KCl, 1 mm $CaCl_2$), 2 mM MgCl2, 10 mM HEPES, pH 7.4) at room temperature. Images were analyzed with Image J and NIS Elements.

Oxygen Consumption Rate (OCR)

OCR was measured to calculate mitochondrial respiration and performed with a Seahorse XF96 extracellular flux analyzer. A 96-well system measures OCR from a monolayer of cultured intact cells, at intervals of ~5 minutes. Astrocytes were plated on Seahorse microplates at least 2 days prior to OCR measurements. All of the major aspects of mitochondrial respiratory control were measured with this instrument by sequentially adding the ATP Synthetase inhibitor oligomycin, which corresponds to the OCR attributed to ATP synthetase (the remaining OCR is proton leak), followed by FCCP, which is a proton ionophore that uncouples mitochondria and reveals maximal respiration. Injection of rotenone and antimycin, inhibitors of complex I and III respectively, uncover non-mitochondrial oxygen consumption.

Photothrombotic Induction of Stroke and Determination of Lesion Volume

Strokes were performed as described previously (2, 3) with the exception that a high speed electric drill (Fine Science Tools) was used to perform a craniotomy and a Nikon Eclipse TE200 was used to illuminate vessels with a 561 nm laser until a clot was visualized. Animals were then injected with 100 ul drug at concentrations stated or with vehicle intraperitoneally within 30 min post stroke formation.

To quantify lesion volume, mice were anesthetized with isoflurane, and were sacrificed via cervical dislocation followed by decapitation. Brains were quickly removed and briefly placed in ice-cold PBS, followed by sectioning into 1 mm slices using a brain matrix (Braintree Scientific). Sections were placed in 0.5% 2,3,5 Triphenyltetrazolium Chloride (TTC, Sigma Aldrich) and incubated for 8 min at 37° C., flipped and incubated another 8 min. TTC was removed, and brains incubated overnight in 8% Paraformaldehyde (PFA) before being scanned using a flatbed scanner and lesion area (as denoted by white, unstained tissue) calculated using ImageJ. For some brains, the ipsilateral hemisphere was taken for TTC staining, and contralateral tissue snap frozen in liquid nitrogen and stored at −80° C. until use for western blot analysis. Statistics were analyzed using GraphPad Prism software.

Cocaine Self-Administration

We used procedures adapted from our recently published work that describes i.v. cocaine self-administration in fully fed mice (6, 7). Male C57BL/6J mice (6 to 7-week-old) purchased from Jackson labs and were kept on a 12/12-hour reverse light-dark cycle (lights off at 0900 h) with ad libitum access to food and water. Cocaine hydrochloride (generously provided by the NIDA drug supply program, Bethesda, MD) was dissolved in sterile physiological saline (NaCl 0.9%). Cocaine was prepared at a concentration that delivers 0.5 mg/kg/12 µL per infusion, based on a typical weight of a young adult mouse (28 g). Mice were implanted with an indwelling catheter in the right jugular vein. One week after surgery mice were trained in operant chambers to nose poke for cocaine intravenous infusions in two-hour daily sessions. Each operant chamber contained both a "correct" hole where a nose poke would result in an infusion and an inactive "incorrect" hole. Training occurred on a fixed ratio of 1 (FR1) reinforcement schedule and "learning" was defined as three consecutive days of at least 8 infusions and a 70% correct/incorrect nose poke ratio. Once self-administration was acquired, mice advanced to an FR3 schedule for at least seven days, with baseline defined as the final three days of stable intake. Mice (n=5 per group) were counterbalanced by cocaine intake and assigned to receive saline or AST-004 via osmotic minipump. Osmotic minipumps (Alzet, model 1004) containing either saline (pink, 100 µL) or AST 004 (purple, 100 µL at 2.78 mM) were implanted subcutaneously in a dorsal pocket between the scapulae. Daily cocaine self-administration sessions (at FR3) were resumed after 1-2 days of recovery from pump implantation, and continued for an additional two weeks. The data presented are normalized to each mouse's individual cocaine intake at baseline. Our data show that mice treated with AST-004 showed a decline in intake over two weeks compared to saline treated mice. The difference in intake between the groups was pronounced after 5 days of self-administration and persisted for the full 2 weeks, with intake stably declining to approximately 60% of baseline in the AST-004 treated group (while the saline treated mice showed an increase in intake over the same time period).

REFERENCES

1 Wu, J. et al. Purinergic receptor-stimulated IP3-mediated Ca2+ release enhances neuroprotection by increasing astrocyte mitochondrial metabolism during aging. *J Neurosci* 27, 6510-6520, doi:10.1523/JNEUROSCI.1256-07.2007 (2007).
2 Zheng, W., Talley Watts, L., Holstein, D. M., Wewer, J. & Lechleiter, J. D. P2Y1R-initiated, IP3R-dependent stimulation of astrocyte mitochondrial metabolism reduces and partially reverses ischemic neuronal damage in mouse. *J Cereb Blood Flow Metab* 33, 600-611, doi:10.1038/jcbfm.2012.214 (2013).
3 Zheng, W. et al. Purinergic receptor stimulation reduces cytotoxic edema and brain infarcts in mouse induced by photothrombosis by energizing glial mitochondria. *PLoS One* 5, e14401, doi:10.1371/journal.pone.0014401 (2010).
4 McCarthy, K. D. & de Vellis, J. Preparation of separate astroglial and oligodendroglial cell cultures from rat cerebral tissue. *J Cell Biol* 85, 890-902 (1980).
5 Lin, D. T. et al. Ca2+ signaling, mitochondria and sensitivity to oxidative stress in aging astrocytes. *Neurobiol Aging* 28, 99-111, doi:10.1016/j.neurobiolaging.2005.11.004 (2007).
6 McCall, N. M. et al. Selective Ablation of GRK Channels in Dopamine Neurons Alters Behavioral Effects of Cocaine in Mice. *Neuropsychopharmacology: official publication of the American College of Neuropsychopharmacology* 42, 707-715, doi:10.1038/npp.2016.138 (2017).
7 Sharpe, A. L., Varela, E., Bettinger, L. & Beckstead, M. J. Methamphetamine self-administration in mice decreases GIRK channel-mediated currents in midbrain dopamine neurons. *Int J Neuropsychopharmacol* 18, doi:10.1093/ijnp/pyu073 (2014).

Example 2: Experimental Protocol for Determining Biased Agonism of Compounds at A3 Adenosine Receptor (A3R)

The following assay may be used to determine whether a disclosed compound, such as AST-004 or MRS1873 (AST-008), exhibits biased agonism (also known as functional selectivity or agonist trafficking) at the $A_3$ receptor.

Materials.

Fluo-4, Dulbecco's modified Eagle's medium (DMEM), and penicillin-streptomycin may be purchased from Invitrogen (Carlsbad, CA). Adenosine deaminase (ADA) and hygromycin-B may be purchased from Roche (Basel, Switzerland). Fetal bovine serum (FBS) may be purchased from ThermoTrace (Melbourne, Australia). AlphaScreen SureFire extracellular signal-regulated kinases 1 and 2 (ERK1/2), Akt 1/2/3, and cAMP kits may be obtained from PerkinElmer (Boston, MA). All compounds prefixed with MRS may be synthesized as described previously (Tosh et al., 2012a,b). All other reagents were purchased from Sigma-Aldrich (St. Louis, MO).

Cell Culture.

The sequence of the human $A_3R$ may be cloned into the Gateway entry vector, pDONR201, and then transferred in the Gateway destination vector, pEF5/FRT/V5-dest, using methods described previously (Stewart et al., 2009). $A_3$-FlpIn-CHO cells may be generated using methods described previously (May et al., 2007) and maintained at 37° C. in a humidified incubator containing 5% $CO_2$ in DMEM supplemented with 10% FBS and the selection antibiotic hygromycin-B (500 µg/ml). For cell survival, ERK1/2 phosphorylation, Akt 1/2/3 phosphorylation, and calcium mobilization assays, cells may be seeded into 96-well culture plates at a density of 4×104 cells/well. After 6 hours, cells are washed with serum-free DMEM and maintained in serum-free DMEM for 12-18 hours at 37° C. in 5% $CO_2$ before assaying. For cAMP assays, cells may be seeded into 96-well culture plates at a density of 2×104 cells/well and incubated overnight at 37° C. in 5% $CO_2$ prior to assay.

Cell Survival Assays.

Media is removed and replaced with HEPES-buffered saline solution (10 mM 4-(2-hydroxyethyl)-1-piperazineethanesulfonic acid (HEPES), 146 mM NaCl, 10 mM D-glucose, 5 mM KCl, 1 mM $MgSO_4$, 1.3 mM $CaCl_2$, and 1.5 mM $NaHCO_3$, pH 7.45) containing ADA (1 U/ml) and penicillin-streptomycin (0.05 U/ml) in the absence and presence of $A_3R$ ligands. Plates are then maintained at 37° C. in a humidified incubator for 24 hours, after which 5 mg/ml propidium iodide is added to cells. Plates may be then read on an EnVision plate reader (PerkinElmer), with excitation and emission set to 320 nm and 615 nm, respectively. Data will be normalized to 100% cell survival and 0% cell survival, determined at t=0 hours in HEPES buffer and t=24 hours in Milli-Q water, respectively.

ERK1/2 and Akt 1/2/3 Phosphorylation Assays.

A concentration-response curve of ERK1/2 and Akt 1/2/3 phosphorylation for each ligand may be performed in serum-free DMEM containing 1 U/ml ADA (5-minute exposure at 37° C.). Agonist stimulation may be terminated by removal of media and the addition of 100 ml of SureFire lysis buffer to each well. Plates are then agitated for 5 minutes. Detection of pERK1/2 may involve an 80:20:120:1:1 v/v/v/v/v dilution of lysate: activation buffer: reaction buffer: AlphaScreen acceptor beads: AlphaScreen donor beads in a total volume of 11 ml in a 384-well ProxiPlate. Plates may be incubated in the dark at 37° C. for 1 hour followed by measurement of fluorescence by an EnVision plate reader (PerkinElmer) with excitation and emission set to 630 nm and 520-620 nm, respectively. Detection of Akt 1/2/3 phosphorylation may employ a 40:9.8:39.2:1 v/v/v/v dilution of lysate: activation buffer: reaction buffer: AlphaScreen acceptor beads in a total volume of 9 l in a 384-well Proxiplate. Plates may be incubated in the dark at room temperature for 2 hours, after which a 19:1 v/v dilution of dilution buffer: AlphaScreen donor beads may be added in a total volume of 11 µl. Plates may be incubated at room temperature for a further 2 hours, followed by measurement of fluorescence by an EnVision plate reader (PerkinElmer) with excitation and emission set to 630 nm and 520-620 nm, respectively. Agonist concentration-response curves are normalized to the phosphorylation mediated by 10% FBS (5-minute stimulation).

Calcium Mobilization Assays.

Media may be removed from 96-well plates and replaced with HEPES-buffered saline solution containing 1 U/ml ADA, 2.5 mM probenecid, 0.5% bovine serum albumin (BSA), and 1 M Fluo4. Plates may be incubated in the dark for 1 hour at 37° C. in a humidified incubator. A FlexStation plate reader (Molecular Devices, Sunnyvale, CA) may perform the addition of HEPES-buffered saline solution in the absence and presence of agonist and measured fluorescence (excitation, 485 nm; emission, 520 nm) every 1.52 seconds for 75 seconds. The difference between the peak and baseline fluorescence may be measured as a marker for intracellular $Ca^{21}$ mobilization. $A_3R$ agonist concentration-response curves may be normalized to the response mediated by 100 µM ATP to account for differences in cell number and loading efficiency.

Inhibition of cAMP Accumulation Assays.

Media may be replaced with a stimulation buffer (140 mM NaCl, 5 mM KCl, 0.8 M $MgSO_4$, 0.2 mM $Na_2HPO_4$, 0.44 mM $KH_2PO_4$, 1.3 mM $CaCl_2$, 5.6 mM D-glucose, 5 mM HEPES, 0.1% BSA, 1 U/ml ADA, and 10 µM rolipram, pH 7.45) and incubated at 37° C. for 1 hour. Inhibition of cAMP accumulation may be assessed by preincubation of $A_3$-Fl-pIn-CHO cells with $A_3R$ agonists for 10 minutes, after which 3 µM forskolin was added for a further 30 minutes. The reaction may be terminated by rapid removal of buffer and addition of 50 µl ice-cold 100% ethanol. Ethanol is allowed to evaporate before the addition of 50 µl detection buffer (0.1% BSA, 0.3% Tween-20, 5 mM HEPES, pH 7.45). Plates are agitated for 10 minutes, after which 10 µl lysate was transferred to a 384-well Optiplate. Detection may employ addition of a 5 µl 1:49 v/v dilution of AlphaScreen acceptor beads: stimulation buffer. Following this, a 15 µl 1:146:3 v/v/v dilution of AlphaScreen donor beads: detection buffer: 3.3 U/µl biotinylated cAMP to form a total volume of 30 µl. The donor bead/biotinylated cAMP mixture may be equilibrated for 30 minutes prior to addition. Plates may be incubated overnight in the dark at room temperature, followed by measurement of fluorescence by an EnVision plate reader (PerkinElmer) with excitation and emission set to 630 nm and 520-620 nm, respectively. Agonist concentration-response curves may be normalized to the response mediated by 3 µM forskolin (0%) or buffer (100%) alone.

Molecular Modeling.

Docking simulations can be performed for all the compounds investigated in this study using homology models of the human $A_3R$. In particular, three previously reported models can be used: a model entirely based on an agonist-bound $hA_{2A}AR$ crystal structure (PDB ID: 3QAK), a model based on a hybrid A2AAR-β2 adrenergic receptor template, and a model based on a hybrid $A_{2A}AR$-opsin template (β2 adrenoceptor X-ray structure PDB ID: 3SN6; opsin crystal X-ray crystal structure PDB ID: 3DQB) (Tosh et al., 2012a). Models based on hybrid templates will show an outward movement of TM2 compared with the $A_{2A}AR$-based model. Structures of $A_3R$ ligands may be built and prepared for docking using the Builder and the LigPrep tools implemented in the Schrödinger suite (Schrödinger Release 2013-3, Schrödinger, LLC, New York, NY, 2013). Molecular docking of the ligands at the $A_3R$ models may be performed by means of the Glide package part of the Schrödinger suite. In particular, a Glide Grid may be centered on the centroid of some key residues of the binding pocket of adenosine receptors, namely, Phe (EL2), Asn (6.55), Trp (6.48), and His (7.43). The Glide Grid may be built using an inner box (ligand diameter midpoint box) of 14 Å×14 Å×14 Å and an outer box (box within which all the ligand atoms must be contained) that extends 25 Å in each direction from the inner one. Docking of ligands may be performed in the rigid binding site using the XP (extra precision) procedure. The top scoring docking conformations for each ligand may be subjected to visual inspection and analysis of protein-ligand interactions to select the proposed binding conformations in agreement with the experimental data.

Data Analysis.

Statistical analyses and curve fitting may be performed using Prism 6 (GraphPad Software, San Diego, CA). To quantify signaling bias, agonist concentration-response curves may be analyzed by nonlinear regression using a derivation of the Black-Leff operational model of agonism, as described previously (Kenakin et al., 2012; Wootten et al., 2013; van der Westhuizen et al., 2014). The transduction coefficient, τ/KA [expressed as a logarithm, Log (τ/KA)], may be used to quantify biased agonism. To account for cell-dependent effects on agonist response, the transduction ratio may be normalized to the values obtained for the reference agonist, IB-MECA, to generate A Log(τ/KA). To determine the bias for each agonist at different signaling pathways, the A Log(τ/KA) will be normalized to a reference pathway, pERK1/2, to generate AA Log(τ/KA). Bias may be defined as $10^{AA\ log(\tau/KA)}$ where a lack of bias will result in values that are not statistically different from 1, or 0 when expressed as a logarithm. All results may be expressed as the mean 6 S.E.M. Statistical analyses would involve an F test or a one-way analysis of variance with a Tukey or Dunnett's post hoc test, with statistical significance determined as P, 0.05.

Example 3: Synthetic Route for AST-004

AST-004 and similar compounds such as MRS1873 (AST-008) may be prepared according to methods known in the art. For example, AST-004 may be prepared from D-ribose by following routes described in Choi, W. J. et al. J. Org. Chem. 2004, 69, 2634-2636, Tosh, D. K. et al.

Purinergic Signalling 2015, 11, 371-387; and Chem. Eur. J., 2009, 15, 6244-6257. Schemes 1 and 2 below show the synthetic route.
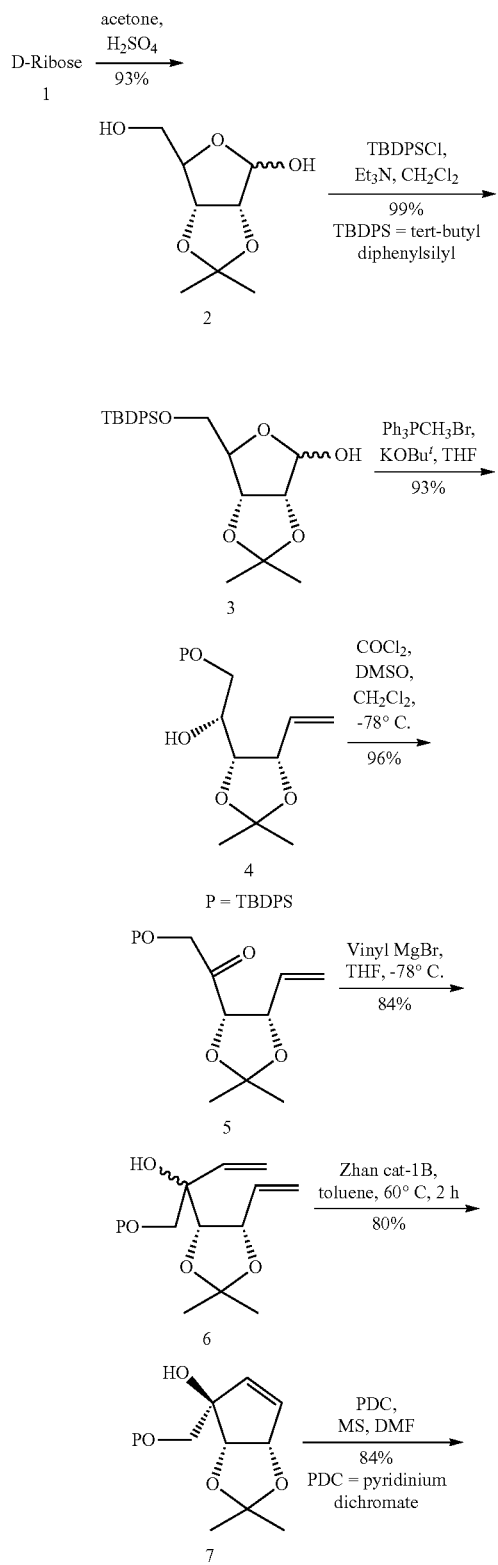
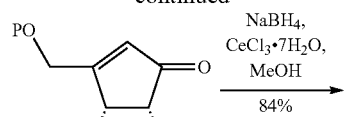
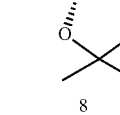
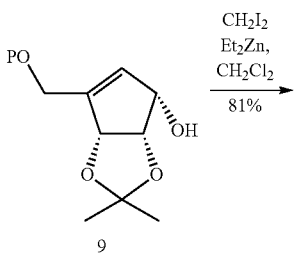
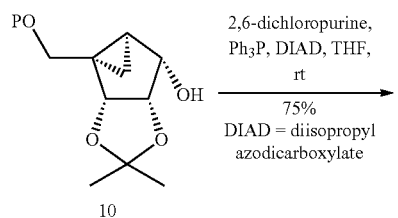
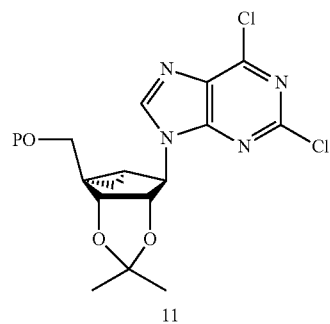
Zhan cat-1B has the following structure:
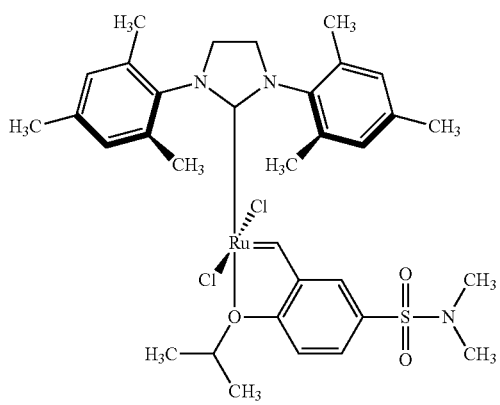
Scheme 2 shows the remainder of the synthesis.

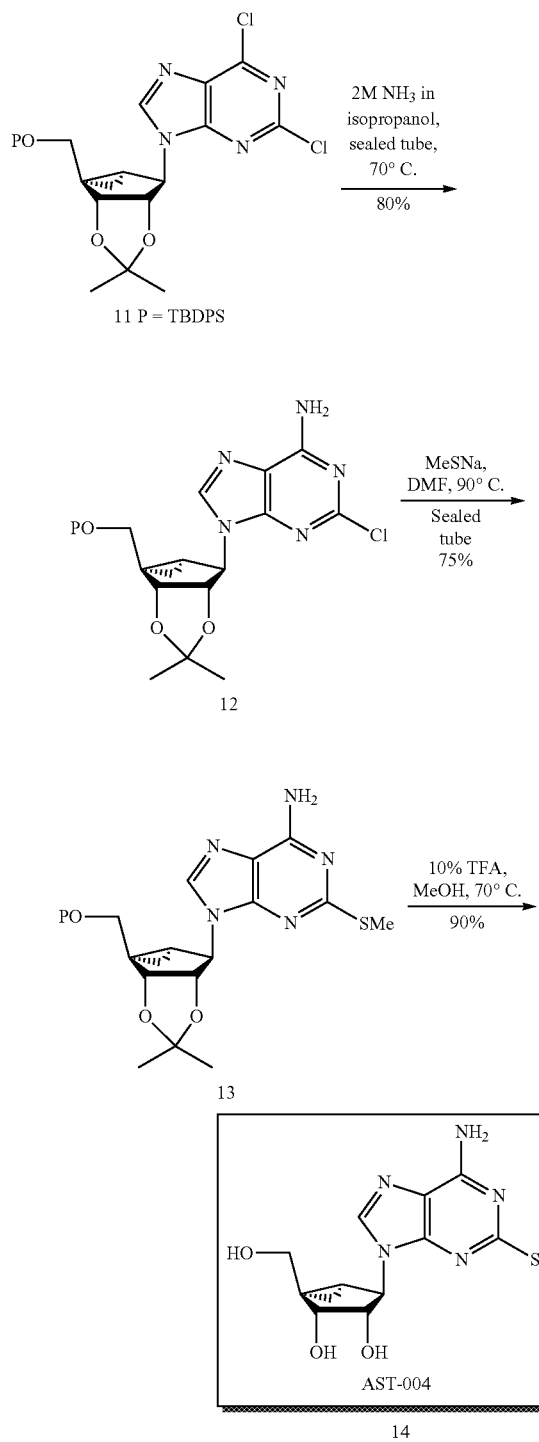

While a number of embodiments of this invention are described, it is understood that the particular examples described above may be altered using routine experimentation to provide other embodiments that utilize the compounds and methods of this invention. Therefore, it will be appreciated that the scope of this invention is to be defined only by the following claims rather than by the specific embodiments that have been provided.

We claim:

1. A method of treating or promoting recovery from an addiction, addictive behavior, behavioral addiction, brain reward system disorder, compulsive disorder, or related condition, or treating relapse of an addiction or addictive behavior, comprising administering to a subject in need thereof an effective amount of a compound selected from:

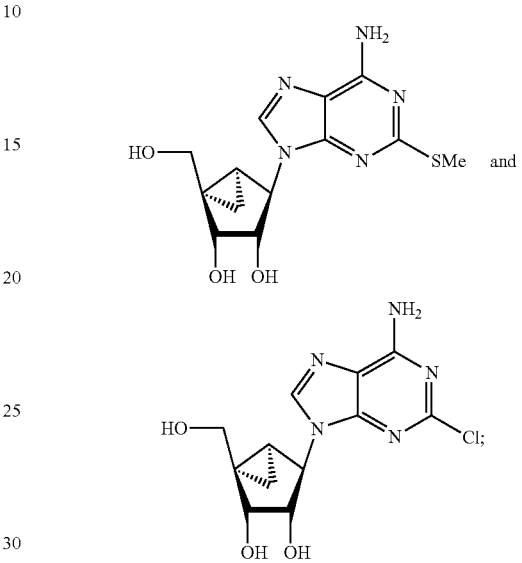

or a pharmaceutically acceptable salt thereof.

2. A method of treating or promoting recovery from withdrawal caused by addiction to a substance or drug having abuse potential, comprising administering to a subject in need thereof an effective amount of a compound selected from:

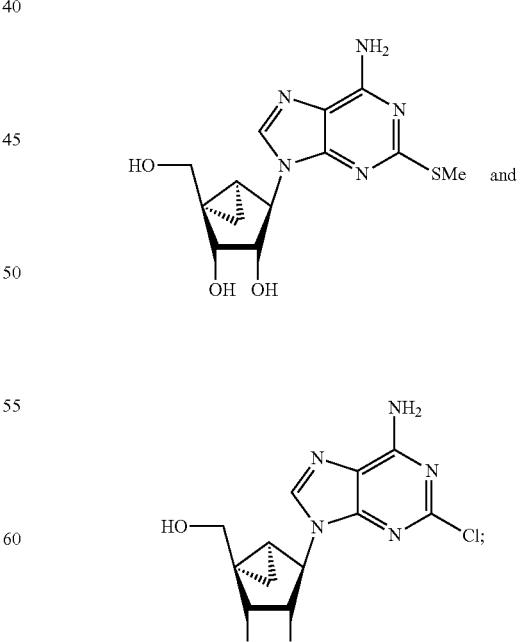

or a pharmaceutically acceptable salt thereof.

3. The method of claim 1, wherein the compound is

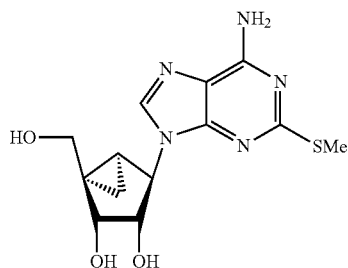

or a pharmaceutically acceptable salt thereof.

4. The method of claim 1, wherein the compound is

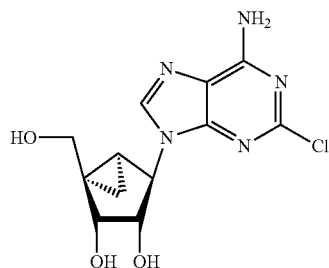

or a pharmaceutically acceptable salt thereof.

5. The method of claim 2, wherein the addiction is to a substance or drug having abuse potential selected from alcohol, nicotine, a narcotic, a prescription drug, and a recreational drug.

6. The method of claim 2, wherein the substance or drug having abuse potential is selected from a stimulant, a depressant, a cannabinoid agonist, and an opioid agonist.

7. The method of claim 2, wherein the substance or drug having abuse potential is selected from heroin, cocaine, alcohol, nicotine, an inhalant, a barbiturate, a benzodiazepine, a prescription opioid agonist analgesic, and an amphetamine; or an analogue, salt, composition, or a combination thereof.

8. The method of claim 2, wherein the substance or drug having abuse potential is selected from alcohol, nicotine, heroin, cocaine, tetrahydrocannabinol (THC), amobarbital, allobarbital, aprobarbital, alphenal, barbital, brallobarbital, pentobarbital, phenobarbital, secobarbital, mephobarbital, butabarbital, tuinal, diazepam (Valium), alprazolam, lorazepam, clonazepam, zolpidem, bupropion, cathinone, MDMA, amphetamine, methamphetamine, dextroamphetamine, methylphenidate, opium, morphine, oxycodone, codeine, methadone, meperidine, oxymorphone, hydrocodone, tramadol, carfentanil, hydromorphone, and fentanyl; or a pharmaceutically acceptable salt or analogue thereof; or a combination thereof.

9. The method of claim 1, wherein the subject has an alcohol or nicotine addiction.

10. The method of claim 1, wherein the subject is a polydrug abuser.

11. The method of claim 1, wherein the method at least partially reverses loss of glutamate uptake into astrocytes caused by the addiction.

12. The method of claim 1, wherein the method increases energy metabolism mediated by astrocytes, glia, microglia, neurons, endothelium cells, or other cells of the brain and/or central nervous system (CNS).

13. The method of claim 1, wherein the method treats a relapse of an addiction or addictive behavior in the subject.

14. The method of claim 1, wherein the method decreases withdrawal symptoms in an addicted individual in withdrawal.

15. A method of ameliorating, treating, or promoting recovery from an addictive behavior, behavioral addiction, brain reward system disorder, compulsive disorder, or related condition, comprising administering to a subject in need thereof an effective amount of a compound selected from:

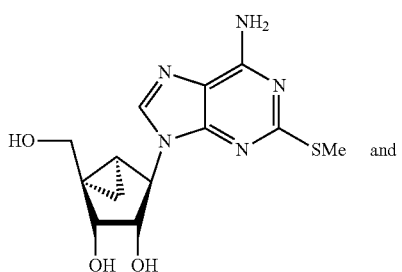 and

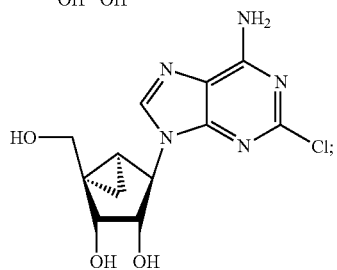

or a pharmaceutically acceptable salt thereof.

16. The method of claim 15, further comprising co-administering a second drug for treating withdrawal.

17. The method of claim 15, wherein the addictive behavior, behavioral addiction, brain reward system disorder, compulsive disorder, or related condition is obsessive-compulsive disorder (OCD), Tourette syndrome, trichotillomania, anorexia, bulimia, anxiety disorder, psychosis, or post-traumatic stress disorder.

18. The method of claim 15, wherein the addictive behavior, behavioral addiction, brain reward system disorder, compulsive disorder, or related condition is selected from gambling addiction, sex addiction, pornography addiction, an eating disorder, spending addiction, rage/anger, workaholism, exercise addiction, a risk-taking addiction, perfectionism, internet or video game addiction, or compulsive use of an electronic device.

* * * * *